(12) United States Patent
Alenfalk et al.

(10) Patent No.: US 7,906,502 B2
(45) Date of Patent: Mar. 15, 2011

(54) 2-AZETIDINONE DERIVATIVES AS CHOLESTEROL ABSORPTION INHIBITORS FOR THE TREATMENT OF HYPERLIPIDAEMIC CONDITIONS

(75) Inventors: Susanne Alenfalk, Molndal (SE); Mikael Dahlstrom, Molndal (SE); Fana Hunegnaw, Molndal (SE); Staffan Karlsson, Molndal (SE); Ingemar Starke, Molndal (SE)

(73) Assignee: AstraZeneca AB, Sodertalje (SE)

( * ) Notice: Subject to any disclaimer, the term of this patent is extended or adjusted under 35 U.S.C. 154(b) by 495 days.

(21) Appl. No.: 11/993,463

(22) PCT Filed: Jun. 21, 2006

(86) PCT No.: PCT/SE2006/000766
§ 371 (c)(1),
(2), (4) Date: Dec. 21, 2007

(87) PCT Pub. No.: WO2006/137797
PCT Pub. Date: Dec. 28, 2006

(65) Prior Publication Data
US 2010/0168039 A1    Jul. 1, 2010

(30) Foreign Application Priority Data

Jun. 22, 2005  (SE) .................. 0501464

(51) Int. Cl.
| | | |
|---|---|---|
| C07D 205/08 | (2006.01) | |
| C07D 405/12 | (2006.01) | |
| A61K 31/397 | (2006.01) | |
| A61P 3/06 | (2006.01) | |
| A61P 9/10 | (2006.01) | |
| C07D 319/06 | (2006.01) | |
| C07D 413/14 | (2006.01) | |

(52) U.S. Cl. ............... 514/210.02; 540/354; 540/358; 540/360; 548/230; 549/436; 549/375

(58) Field of Classification Search ............ 540/360; 514/210.02
See application file for complete search history.

(56) References Cited

U.S. PATENT DOCUMENTS

| | | | |
|---|---|---|---|
| 5,633,246 A | 5/1997 | McKittrick et al. | |
| 5,661,145 A | 8/1997 | Davis | |
| 7,235,543 B2 | 6/2007 | Burnett et al. | |
| 7,368,562 B2 | 5/2008 | Burnett et al. | |
| 7,470,678 B2 * | 12/2008 | Starke et al. ............. | 514/210.09 |
| 2003/0119428 A1 | 6/2003 | Davis et al. | |
| 2003/0119757 A1 | 6/2003 | Davis | |
| 2004/0018060 A1 | 1/2004 | Knezek et al. | |
| 2004/0018061 A1 | 1/2004 | Jansson | |
| 2004/0254369 A1 | 12/2004 | Framroze | |
| 2005/0096307 A1 | 5/2005 | Graziano | |
| 2005/0267049 A1 | 12/2005 | Goulet et al. | |
| 2006/0046996 A1 | 3/2006 | Aoki et al. | |
| 2006/0069080 A1 | 3/2006 | Veltri | |
| 2007/0049748 A1 | 3/2007 | Uppala | |
| 2007/0078098 A1 | 4/2007 | DeVita et al. | |
| 2007/0129540 A1 | 6/2007 | Framroze | |
| 2007/0142304 A1 * | 6/2007 | Alenfalk et al. ............... | 514/19 |
| 2007/0155674 A1 | 7/2007 | Burnett et al. | |
| 2007/0155675 A1 | 7/2007 | Burnett et al. | |
| 2008/0064676 A1 * | 3/2008 | Alenfalk et al. ......... | 514/210.02 |
| 2008/0070890 A1 * | 3/2008 | Burnett et al. ............ | 514/210.05 |
| 2009/0069285 A1 * | 3/2009 | Lemurell et al. ......... | 514/210.02 |
| 2010/0048529 A1 * | 2/2010 | Dahlstrom et al. ...... | 514/210.02 |
| 2010/0048530 A1 * | 2/2010 | Dahlstrom et al. ...... | 514/210.15 |
| 2010/0099657 A2 * | 4/2010 | Alenfalk et al. ......... | 514/210.02 |
| 2010/0125059 A1 * | 5/2010 | Nakano et al. ........... | 514/210.02 |
| 2010/0137273 A1 * | 6/2010 | Alenfalk et al. ......... | 514/210.02 |

(Continued)

FOREIGN PATENT DOCUMENTS

EP            1413331           9/2001

(Continued)

OTHER PUBLICATIONS

Notice of allowance dated Jul. 31, 2008 for U.S. Appl. No. 10/519,897.

(Continued)

*Primary Examiner* — Mark L Berch
(74) *Attorney, Agent, or Firm* — Pepper Hamilton LLP

(57) ABSTRACT

Compounds of formula (I) (wherein variable groups are as defined within) pharmaceutically acceptable salts, solvates, solvates of such salts and prodrugs thereof and their use as cholesterol absorption inhibitors for the treatment of hyperlipidaemia are described. Processes for their manufacture and pharmaceutical compositions containing them are also described.

31 Claims, No Drawings

U.S. PATENT DOCUMENTS

| | | |
|---|---|---|
| 2010/0152156 A1 | 6/2010 | Dahlstrom et al. |
| 2010/0168075 A1 | 7/2010 | Dahlstrom et al. |
| 2010/0216759 A1 | 8/2010 | Alenfalk et al. |

FOREIGN PATENT DOCUMENTS

| | | |
|---|---|---|
| EP | 0792264 | 2/2002 |
| EP | 1362855 | 11/2003 |
| WO | 03026643 | 4/2003 |
| WO | 2004043456 | 5/2004 |
| WO | 2004043457 | 5/2004 |
| WO | 2004099132 | 11/2004 |
| WO | 2004107958 | 12/2004 |
| WO | 2005000353 | 1/2005 |
| WO | 2005021495 | 3/2005 |
| WO | 2005021497 | 3/2005 |
| WO | 2005042692 | 5/2005 |
| WO | 2005044256 | 5/2005 |
| WO | 2005047248 | 5/2005 |
| WO | 2005049592 | 6/2005 |
| WO | 2005058316 | 6/2005 |
| WO | 2005033100 | 7/2005 |
| WO | 2005061451 | 7/2005 |
| WO | 2005061452 | 7/2005 |
| WO | 2005062824 | 7/2005 |
| WO | 2005062897 | 7/2005 |
| WO | 2005066120 | 7/2005 |
| WO | 2005067903 | 7/2005 |
| WO | 2005069900 | 8/2005 |
| WO | 2005113495 | 12/2005 |
| WO | 2005113496 | 12/2005 |
| WO | 2006017257 | 2/2006 |
| WO | 2006060808 | 6/2006 |
| WO | 2006068990 | 6/2006 |
| WO | 2006072957 | 7/2006 |
| WO | 2006086562 | 8/2006 |
| WO | 2006102674 | 9/2006 |
| WO | 2006107936 | 10/2006 |
| WO | 2006107936 | 10/2006 |
| WO | 2006116499 | 11/2006 |
| WO | 2006121861 | 11/2006 |
| WO | 2006122186 | 11/2006 |
| WO | 2006122216 | 11/2006 |
| WO | 2006124713 | 11/2006 |
| WO | 2006127893 | 11/2006 |
| WO | 2006134604 | 12/2006 |
| WO | 2006137080 | 12/2006 |
| WO | 2006137782 | 12/2006 |
| WO | 2006137792 | 12/2006 |
| WO | 2006137793 | 12/2006 |
| WO | 2006137794 | 12/2006 |
| WO | 2006137795 | 12/2006 |
| WO | 2006137796 | 12/2006 |
| WO | 2006137797 | 12/2006 |
| WO | 2006138163 | 12/2006 |
| WO | 2007003365 | 1/2007 |
| WO | 2007008529 | 1/2007 |
| WO | 2007008541 | 1/2007 |
| WO | 2007015161 | 2/2007 |
| WO | 2007016643 | 2/2007 |
| WO | 2007017705 | 2/2007 |
| WO | 2007030721 | 3/2007 |
| WO | 2007058335 | 5/2007 |
| WO | 2007059871 | 5/2007 |
| WO | 2007072088 | 6/2007 |
| WO | 2007075702 | 7/2007 |

OTHER PUBLICATIONS

Office Action dated Feb. 28, 2008 for U.S. Appl. No. 10/519,897.
Notice of allowance dated Aug. 28, 2007 for U.S. Appl. No. 10/519,897.
Office Action dated May 1, 2007 for U.S. Appl. No. 10/519,897.
Ritter et al., "Heterocyclic ring scaffolds as small-molecule cholesterol absorption inhibitors," Org Biomol Chem (2005) 3:3514-3523.
Clader et al., "2-Azetidinone Cholesterol Absorption Inhibitors: Structure-Activity Relationships on the HeterocyclicNucleus," J. Med Chem (1996) 39:3684-3693.
McKittrick et al., Stereoselective synthesis and biological activity of cis azetidinones as cholesterol absorptioninhibitors, Bioorganic & Medicinal Chemistry Letters (1996) 6(16):1947-1950.
Burnett et al., "2-Azetidinones as Inhibitors of Cholesterol Absorption," J. Med Chem (1994) 12:1733-1736.
Castaner et al., "Ezetimibe Hypolipidemic, Cholesterol absorption inhibitor," Drugs of the Future (2000) 25(7):679-685.
Vaccaro et al., "Sugar-substituted 2-azetidinone cholesterol absorption inhibitors: Enhanced potency by modification ofthe sugar," Bioorganic & Medicinal Chemistry Letters (1998) 8:313-318.
Fu et al., "Process for preparing Ezetimibe intermediate by an acid enhanced chemo- and enantioselective CBScatalyzed ketone reduction," Tetrahedron Letters (2003) 44:801-804.
Kirkup et al., "(i)-SCH 57939: synthesis and pharmacological properties of a potent, metabolically stable cholesterolabsorption inhibitor," Bioorganic & Medicinal Chemistry Letters (1996) 6(17):2069-2072.
Rosenblum et al., "Discovery of 1-(4-fluorophenyl)-(3R)-[3-(4-fluorophenyl)-(3S)-hydroxypropyl]-(4S)-(4-hydroxyphenyl)-2-azetidinone (SCH 58235): A designed, potent, orally active inhibitor of cholesterol absorption.," J. Med Chem (1998) 41:973-980.
Wu et al., "A Novel One-Step Diastereo- and Enantioselective Formation of trans-Azetidinones and Its Application tothe Total Synthesis of Cholesterol Absorption Inhibitors," J. Org. Chem (1999) 64:3714-3718.
Dugar et al., "Gamma-lactams and related compounds as cholesterol absorption inhibitors: homologs of the beta-lactam cholesterol absorption inhibitor SCH 48461," Bioorganic & Medicinal Letters (1995) 5(24):2947-2952.
Mounsey et al., "Diet may slow progression of diabetic nephropathy," The Journal of Family Practice (2003) 52 (9):672-673.
Sobieszczyk et al., "Acute pulmonary embolism: don't ignore the platelet," Circulation (2002) 106(14):1748-1749.
van Heek et al., "Comparison of the activity and disposition of the novel cholesterol absorption inhibitor, SCH58235, and its glucuronide, SCH60663," Br. J. Pharmacol (2000) 129(8):1748-1754.
Yang et al., "Allelic Variants in Long-QT Disease Genes in Patients With Drug-Associated Torsades de Pointes," Circulation (2002) 105(16):1943-1948.
Zaks et al., Enzymatic glucuronidation of a novel cholesterol absorption inhibitor, Sch 58235, Appl BiochemBiotechnol. (1998) 73(2-3):205-214.
Clader "The discovery of ezetimibe: a view from outside the receptor," J Med Chem (2004 47(1):1-9.
Altmann et al., "Niemann-pick C1 like 1 protein is critical for intestinal cholesterol absorption," Science(2004) 303:1201-1204.
Journal of the American College of Cardiology (2000) 35(1):252A.
Kvaerno et al., "Synthesis and in vitro evaluation of inhibitors of intestinal cholesterol absorption," J Med Chem (2005) 48(19):6035-6053.
Burnett "Beta-lactam cholesterol absorption inhibitors," Curr Med Chem (2004) 11:1873-1887.
Seedorf et al., "Cholesterol absorption inhibitor ezetimibe blocks uptake of oxidized LDL in human macrophages," Biochem Biophys Research Commun (2004) 320(4):1337-1341.
Kvaerno et al., "An in vitro assay for evaluation of small-molecule inhibitors of cholesterol absorption," (2004) 43 (35):4653-4656.
Clader "Ezetimibe and other azetidinone cholesterol absorption inhibitors," Curr Topics in Med Chem (2005) 5 (3):243-256.
Carcia-Calvo et al., "The target of ezetimibe is Niemann-Pick C1-Like 1 (NPC1L1)," PNAS (2005) 102(23):8132-8137.
Office Action dated May 3, 2010 received in copending U.S. Appl. No. 10/596,731.
Office Action dated Sep. 17, 2009 received in copending U.S. Appl. No. 10/593,731.
Office Action dated Jul. 15, 2009 received in copending U.S. Appl. No. 10/596,725.
Non Final Action received in copending U.S. Appl. No. 11/993,033 dated Jun. 10, 2010.
Notice of Allowance and Fee(s) Due received in copending U.S. Appl. No. 10/596,731 dated May 27, 2010.

Non Final Office Action received in copending U.S. Appl. No. 11/993,466 dated Jun. 9, 2010.
Office Action dated Jun. 4, 2010 received in copending U.S. Appl. No. 11/993,484.
Office Action dated Jun. 9, 2010 received in copending U.S. Appl. No. 11/993,479.
Office Action dated Jun. 9, 2010 received in copending U.S. Appl. No. 11/993,475.
Office Action dated Jun. 10, 2010 received in copending U.S. Appl. No. 11/993,470.
Notice of Allowance dated Sep. 8, 2010 received in copending U.S. Appl. No. 11/993,033.
Notice of allowance Oct. 12, 2010 received in copending U.S. Appl. No. 11/993,466.

* cited by examiner

2-AZETIDINONE DERIVATIVES AS CHOLESTEROL ABSORPTION INHIBITORS FOR THE TREATMENT OF HYPERLIPIDAEMIC CONDITIONS

CROSS-REFERENCE TO RELATED APPLICATIONS

This application is the U.S. National Stage filing of International Application Serial No. PCT/SE2006/000766 filed Jun. 21, 2006, which claims priority to Swedish Application Serial No. 0501464-2 filed Jun. 22, 2005, each of which is incorporated herein by reference in its entirety.

This invention relates to 2-azetidinone derivatives, or pharmaceutically acceptable salts, solvates, solvates of such salts and prodrugs thereof. These 2-azetidinones possess cholesterol absorption inhibitory activity and are accordingly of value in the treatment of disease states associated with hyperlipidaemic conditions. They are therefore useful in methods of treatment of a warm-blooded animal, such as man. The invention also relates to processes for the manufacture of said 2-azetidinone derivatives, to pharmaceutical compositions containing them and to their use in the manufacture of medicaments to inhibit cholesterol absorption in a warm-blooded animal, such as man. A further aspect of this invention relates to the use of the compounds of the invention in the treatment of dyslipidemic conditions.

Atherosclerotic coronary artery disease is a major cause of death and morbidity in the western world as well as a significant drain on healthcare resources. It is well-known that hyperlipidaemic conditions associated with elevated concentrations of total cholesterol and low density lipoprotein (LDL) cholesterol are major risk factors for cardiovascular atherosclerotic disease (for instance "Coronary Heart Disease: Reducing the Risk; a Worldwide View" Assman G., Carmena R. Cullen P. et al; Circulation 1999, 100, 1930-1938 and "Diabetes and Cardiovascular Disease: A Statement for Healthcare Professionals from the American Heart Association" Grundy S, Benjamin I., Burke G., et al; Circulation, 1999, 100, 1134-46).

Sitosterolemia is a lipid storage disorder characterised by increased levels of sitosterol and other plant sterols in the plasma and other tissues due to increased non-selective intestinal absorption of sterols and decreased hepatic removal. Sitosterolemia can result in accelerated atherosclerosis and other cardiovascular diseases. See WO 02/058696.

The concentration of plasma cholesterol depends on the integrated balance of endogenous and exogenous pathways of cholesterol metabolism. In the endogenous pathway, cholesterol is synthesized by the liver and extra hepatic tissues and enters the circulation as lipoproteins or is secreted into bile. In the exogenous pathway cholesterol from dietary and biliary sources is absorbed in the intestine and enters the circulation as component of chylomicrons. Alteration of either pathway will affect the plasma concentration of cholesterol.

The precise mechanism by which cholesterol is absorbed from the intestine is however not clear.

A clear association between reduction of total cholesterol and (LDL) cholesterol and decreased instance of coronary artery disease has been established, and several classes of pharmaceutical agents are used to control serum cholesterol. The major options to regulate plasma cholesterol include (i) blocking the synthesis of cholesterol by agents such as HMG-CoA reductase inhibitors, for example statins such as simvastatin and fluvastatin, which also by up-regulation of LDL-receptors will promote the cholesterol removal from the plasma; (ii) blocking the bile acid reabsorption by specific agents resulting in increased bile acid excretion and synthesis of bile acids from cholesterol with agents such as bile acid binders, such as resins e.g. cholestyramine and cholestipol; and (iii) by blocking the intestinal uptake of cholesterol by selective cholesterol absorption inhibitors. High density lipoprotein (HDL) elevating agents such as fibrates and nicotinic acid analogues have also been employed.

Compounds possessing such cholesterol absorption inhibitory activity have been described, see for instance the compounds described in WO 93/02048, WO 94/17038, WO 95/08532, WO 95/26334, WO 95/35277, WO 96/16037, WO 96/19450, WO 97/16455, WO 02/50027, WO 02/50060, WO 02/50068, WO 02/50090, WO 02/66464, WO 04/000803, WO 04/000804, WO04/000805, WO04/01993, WO04/010948, WO04/043456 WO 04/043457, WO 04/081002, WO05/000353, WO05/021495, WO05/021497, WO05/033100, U.S. Pat. No. 5,756,470, U.S. Pat. No. 5,767,115, US 20040180860, US20040180861 and US RE37721.

The present invention is based on the discovery that certain 2-azetidinone derivatives surprisingly inhibit cholesterol absorption. Such properties are expected to be of value in the treatment of disease states associated with hyperlipidaemic conditions. The compounds of the present invention are not disclosed in any of the above applications and we have surprisingly found that the compounds of the present invention possess beneficial efficacious, metabolic and toxicological profiles that make them particularly suitable for in vivo administration to a warm blooded animal, such as man. In particular certain compounds of the present invention have a low degree of absorption compared to compounds of the prior art whilst retaining their ability to inhibit cholesterol absorption.

Accordingly there is provided a compound of formula (I):
A compound of formula (I):

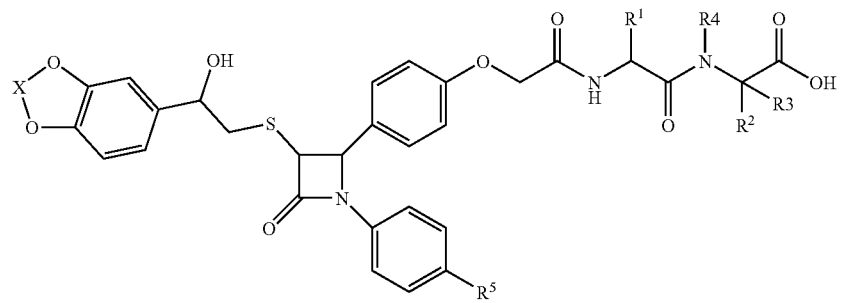

Wherein:

X=—CH$_2$—, —CH$_2$CH$_2$—, —CH$_2$CH$_2$CH$_2$—;

R$^1$=H, C$_{1-6}$ alkyl, C$_{3-6}$cycloalkyl or aryl;

R$^2$ and R$^3$ is hydrogen, a branched or unbranched C$_{1-6}$alkyl, C$_{3-6}$cycloalkyl or aryl; wherein said C$_{1-6}$alkyl may be optionally substituted by one or more hydroxy, amino, guanidino, carbamoyl, carboxy, C$_{1-6}$alkoxy, (C$_1$-C$_4$ alkyl)$_3$Si, N—(C$_{1-6}$ alkyl)amino, N,N—(C$_{1-6}$alkyl)$_2$-amino, C$_{1-6}$alkylS(O)$_a$ wherein a is 0-2, C$_{3-6}$cycloalkyl or aryl; and wherein any aryl group may be optionally substituted by one or two substituents selected from halo, hydroxy, cyano, C$_{1-6}$alkyl or C$_{1-6}$alkoxy;

R$^4$ is hydrogen, C$_{1-6}$ alkyl, or arylC$_{1-6}$ alkyl;

wherein R$^3$ and R$^2$ may form a ring with 3-7 carbon atoms and wherein R$^4$ and R$^2$ may form a ring with 2-6 carbon atoms;

R$^5$ is selected from hydrogen, halo, nitro, cyano, hydroxy, carboxy, carbamoyl, sulphamoyl, C$_{1-6}$alkyl, C$_{1-6}$alkoxy, C$_{1-6}$alkanoyl, C$_{1-6}$alkanoyloxy, N—(C$_{1-6}$alkyl)amino, N,N—(C$_{1-6}$alkyl)$_2$amino, C$_{1-6}$alkanoylamino, N—(C$_{1-6}$ alkyl)carbamoyl, N,N—(C$_{1-6}$alkyl)$_2$carbamoyl, C$_{1-6}$alkylS (O)$_a$ wherein a is 0 to 2, C$_{1-6}$alkoxycarbonyl, N—(C$_{1-6}$alkyl) sulphamoyl and N,N—(C$_{1-6}$alkyl)$_2$sulphamoyl; and wherein n is 0, 1, 2 or 3.

In this specification the term "alkyl" includes both straight and branched chain alkyl groups but references to individual alkyl groups such as "propyl" are specific for the straight chain version only. For example, "C$_{1-6}$alkyl" and "C$_{1-6}$alkyl" include propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "phenylC$_{1-6}$alkyl" would include benzyl, 1-phenylethyl and 2-phenylethyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

The term "aryl" refers to a 4-10 membered aromatic mono or bicyclic ring containing 0 to 5 heteroatoms independently selected from nitrogen, oxygen or sulphur. Examples of aryls include phenyl, pyrrolyl, furanyl, imidazolyl, triazolyl, tetrazolyl, pyrazinyl, pyrimidinyl, pyridazinyl, pyridyl, isoxazolyl, oxazolyl, 1,2,4 oxadiazolyl, isothiazolyl, thiazolyl, 1,2,4-triazolyl, thienyl, naphthyl, benzofuranyl, benzimidazayl, benzthienyl, benzthiazolyl, benzisothiazolyl, benzoxazolyl, benzisoxazolyl, 1,3-benzodioxolyl, indolyl, pyridoimidazolyl, pyrimidoimidazolyl, quinolyl, isoquinolyl, quinoxalinyl, quinazolinyl, phthalazinyl, cinnolinyl and naphthyridinyl. Particularly "aryl" refers to phenyl, thienyl, pyridyl, imidazolyl or indolyl. The term "aryl" includes both unsubstituted and substituted aromatic rings.

Examples of "C$_{1-6}$alkoxy" include methoxy, ethoxy and propoxy. Examples of "C$_{1-6}$alkylS(O)$_a$ wherein a is 0 to 2" include methylthio, ethylthio, methylsulphinyl, ethylsulphinyl, mesyl and ethylsulphonyl. Examples of "N—(C$_{1-6}$alkyl) amino" include methylamino and ethylamino. Examples of "N,N—(C$_{1-6}$alkyl)$_2$amino" include di-N-methylamino, di-(N-ethyl)amino and N-ethyl-N-methylamino. "C$_{3-6}$cycloalkyl" refers to cyclopropyl, cyclobutyl, cyclopentyl and cyclohexyl.

A suitable pharmaceutically acceptable salt of a compound of the invention, or other compounds disclosed herein, is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric, acetate or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds of the formula (I), or other compounds disclosed herein, may be administered in the form of a pro-drug which is broken down in the human or animal body to give a compound of the formula (I). Examples of pro-drugs include in vivo hydrolysable esters and in vivo hydrolysable amides of a compound of the formula (I).

An in vivo hydrolysable ester of a compound of the formula (I), or other compounds disclosed herein, containing carboxy or hydroxy group is, for example, a pharmaceutically acceptable ester which is hydrolysed in the human or animal body to produce the parent acid or alcohol. Suitable pharmaceutically acceptable esters for carboxy include C$_{1-6}$alkoxymethyl esters for example methoxymethyl, C$_{1-6}$alkanoyloxymethyl esters for example pivaloyloxymethyl, phthalidyl esters, C$_{3-8}$cycloalkoxycarbonyloxyC$_{1-6}$alkyl esters for example 1-cyclohexylcarbonyloxyethyl; 1,3-dioxolen-2-onylmethyl esters for example 5-methyl-1,3-dioxolen-2-onylmethyl; and C$_{1-6}$alkoxycarbonyloxyethyl esters for example 1-methoxycarbonyloxyethyl and may be formed at any carboxy group in the compounds of this invention.

An in vivo hydrolysable ester of a compound of the formula (I), or other compounds disclosed herein, containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

A suitable value for an in vivo hydrolysable amide of a compound of the formula (I), or other compounds disclosed herein, containing a carboxy group is, for example, a N—C$_{1-6}$ alkyl or N,N-di-C$_{1-6}$alkyl amide such as N-methyl, N-ethyl, N-propyl, N,N-dimethyl, N-ethyl-N-methyl or N,N-diethyl amide.

Some compounds of the formula (I) may have chiral centres and/or geometric isomeric centres (E- and Z-isomers), and it is to be understood that the invention encompasses all such optical, diastereoisomers and geometric isomers that possess cholesterol absorption inhibitory activity.

The invention relates to any and all tautomeric forms of the compounds of the formula (I) that possess cholesterol absorption inhibitory activity.

It is also to be understood that certain compounds of the formula (I) can exist in solvated as well as unsolvated forms such as, for example, hydrated forms. It is to be understood that the invention encompasses all such solvated forms which possess cholesterol absorption inhibitory activity.

Preferred aspects of the invention are those which relate to the compound of formula (I) or a pharmaceutically acceptable salt thereof.

Another aspect of the present invention provides a process for preparing a compound of formula (I) or a pharmaceutically acceptable salt, solvate, solvate of such a salt or a prodrug thereof which process (wherein variable groups are, unless otherwise specified, as defined in formula (I)) comprises of:

Process 1) Reacting a Compound of Formula (II):

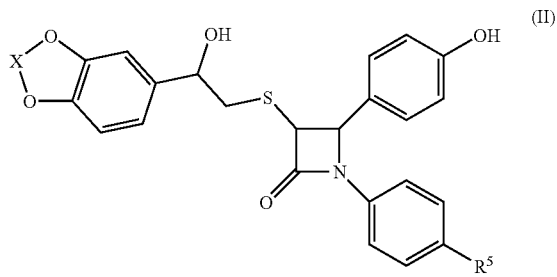

with a compound of formula (III):

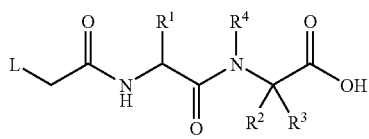

wherein L is a displaceable group;

Process 2) Reacting an Acid of Formula (IV):

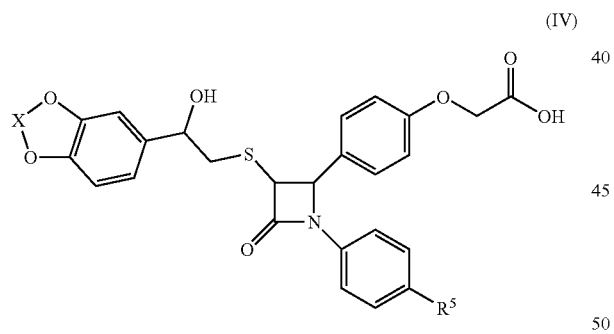

or an activated derivative thereof: with an amine of formula (V):

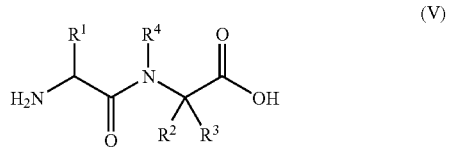

Process 3): Reacting an Acid of Formula (VI):

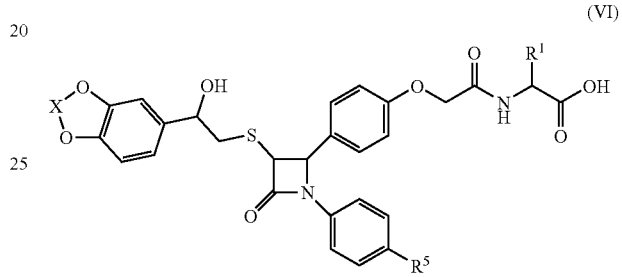

or an activated derivative thereof, with an amine of formula (VII):

Process 4): Reducing a Compound of Formula (VIII):

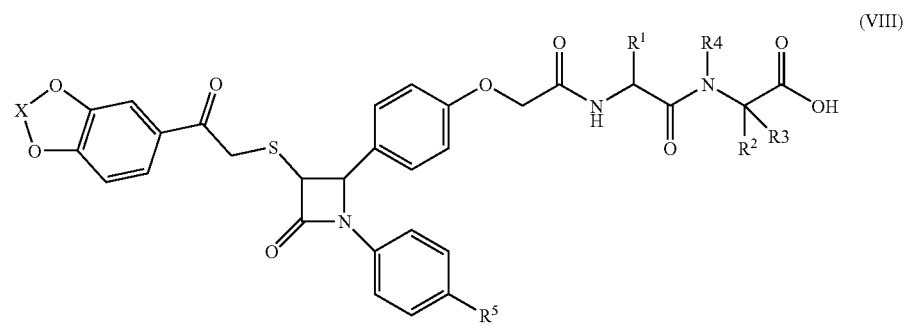

Process 5): Reacting a Compound of Formula (IX):

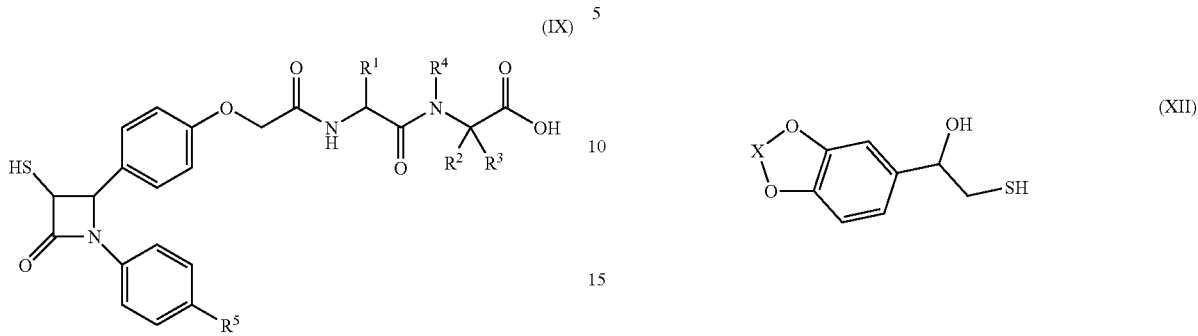

with a compound of formula (X):

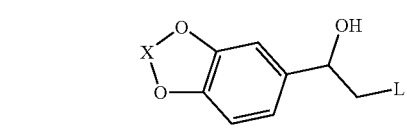

wherein L is a displaceable group;
Process 6): Reacting a Compound of Formula (XI):

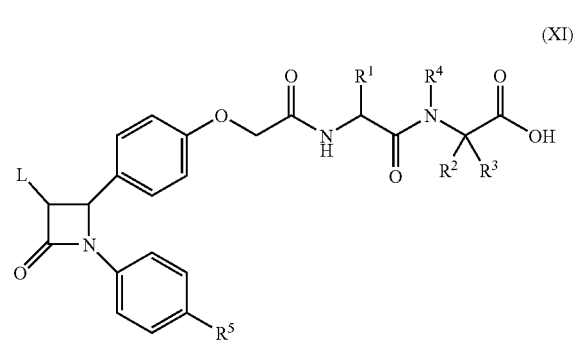

wherein L is a displaceable group; with a compound of formula (XII):

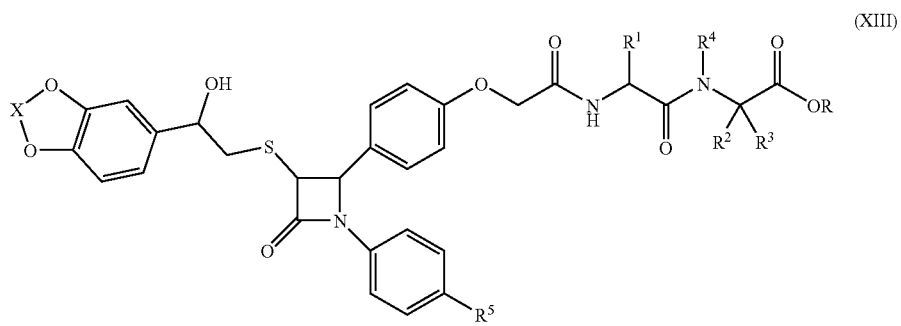

Process 7): De-Esterifying a Compound of Formula (XIII)

wherein the group C(O)OR is an ester group; and thereafter if necessary or desirable:

i) converting a compound of the formula (I) into another compound of the formula (I);

ii) removing any protecting groups;

iii) forming a pharmaceutically acceptable salt, solvate, solvate of such a salt or a prodrug; or iv) separating two or more enantiomers.

L is a displaceable group, suitable values for L are for example, a halogen or sulphonyloxy group, for example a chloro, bromo, methanesulphonyloxy or toluene-4-sulphonyloxy group.

C(O)OR is an ester group, suitable values for C(O)OR are methoxycarbonyl, ethoxycarbonyl, t-butoxycarbonyl and benzyloxycarbonyl.

The starting materials used in the present invention can be prepared by modifications of the routes described in EP 0 792 264 B1. Alternatively they can be prepared by the following reactions.

Process 1): Alcohols of formula (II) may be reacted with compounds of formula (III) in the presence of a base for example an inorganic base such as sodium carbonate, or an organic base such as Hunigs base, in the presence of a suitable solvent such as acetonitrile, dichloromethane or tetrahydrofuran at a temperature in the range of 0° C. to reflux, preferably at or near reflux.

Compounds of formula (II) may be prepared according to the following scheme:
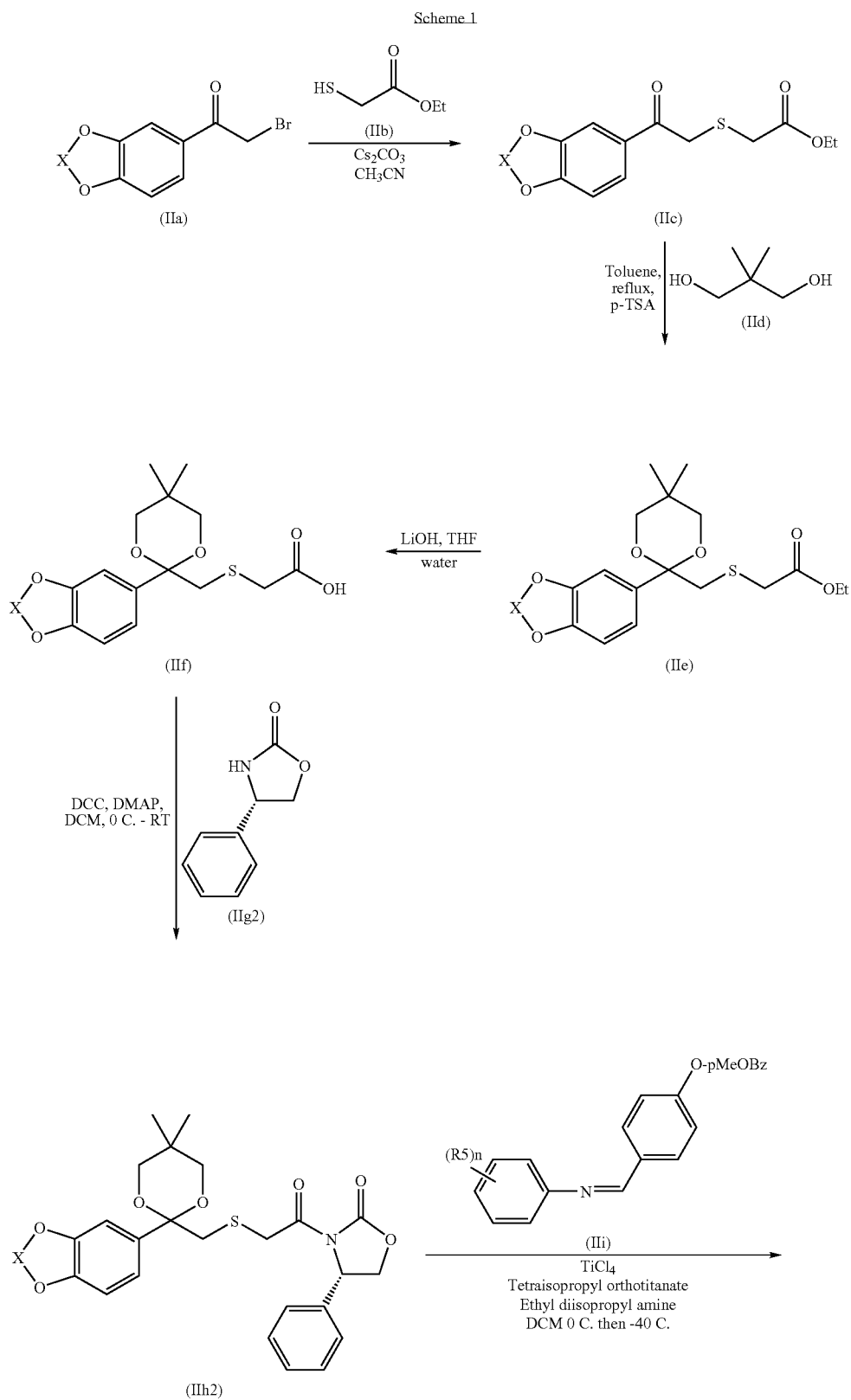

-continued

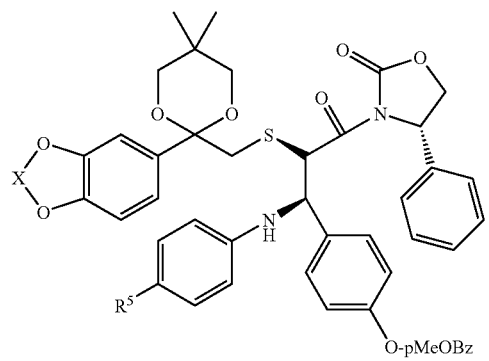
(IIj2)

N,O-bis trimethylsilyl acetamide
Toluene, 90 C. -45 C.
cat TBAF

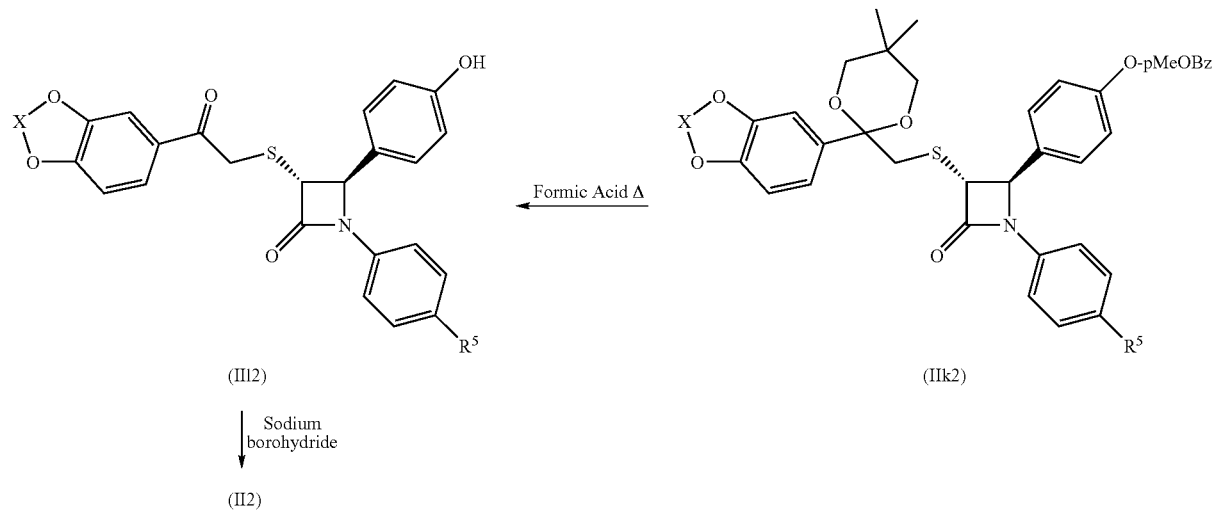

wherein pMeOBz is para methoxy benzyl.

Compounds of formula (IIb), (IId), (IIg) and (III) are commercially available compounds, or they are known in the literature, or they are prepared by standard processes known in the art.

Another aspect of the present invention provides a process for preparing a compound of formula (I2)

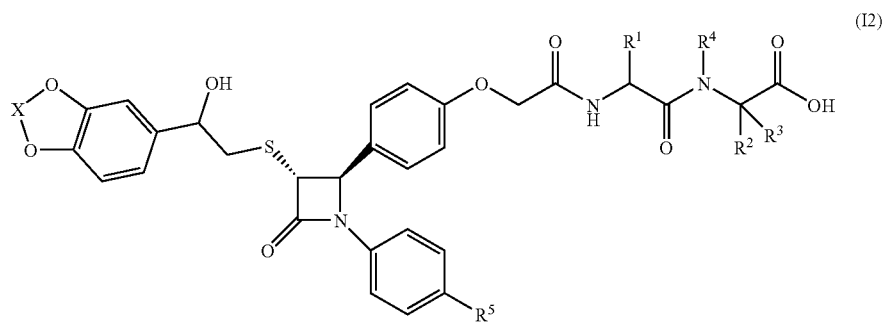
(I2)

or a pharmaceutically acceptable salt, solvate, solvate of such a salt or a prodrug thereof which process (wherein variable groups are, unless otherwise specified, as defined in formula (I)) comprises of:

Process 1) reacting a compound of formula (II2):

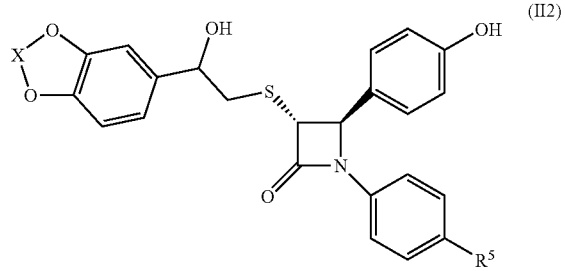

with a compound of formula (III):

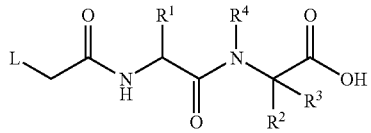

wherein L is a displaceable group;

Process 2) Reacting an Acid of Formula (IV2):

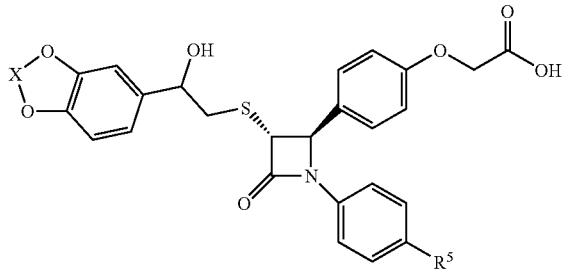

or an activated derivative thereof; with an amine of formula (V):

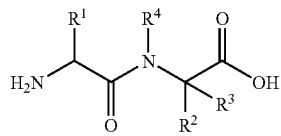

Process 3): Reacting an Acid of Formula (VI2):

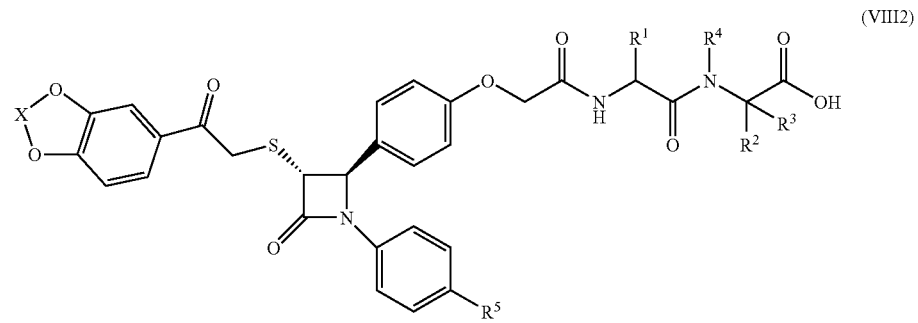

or an activated derivative thereof, with an amine of formula (VII):

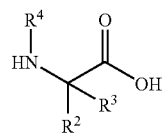

Process 4): Reducing a Compound of Formula (VIII2):

Process 5): Reacting a Compound of Formula (IX2):

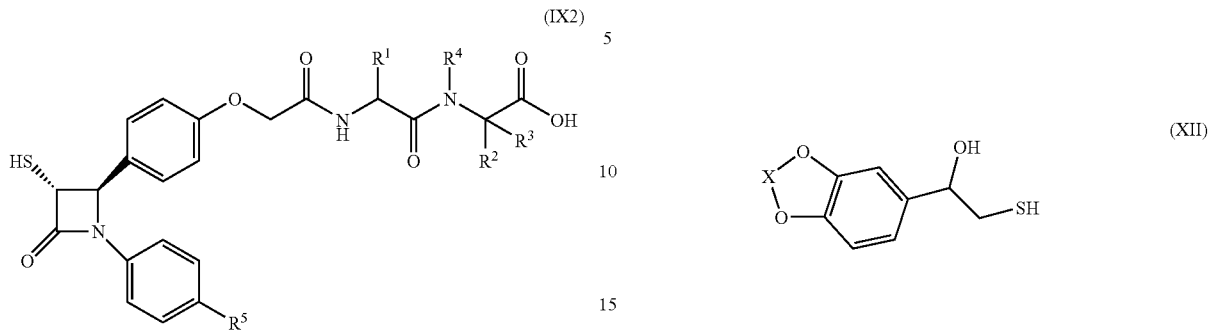

with a compound of formula (X):

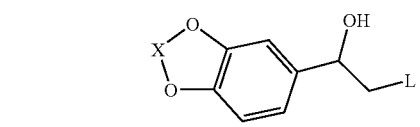

wherein L is a displaceable group;
Process 6): Reacting a Compound of Formula (XI2):

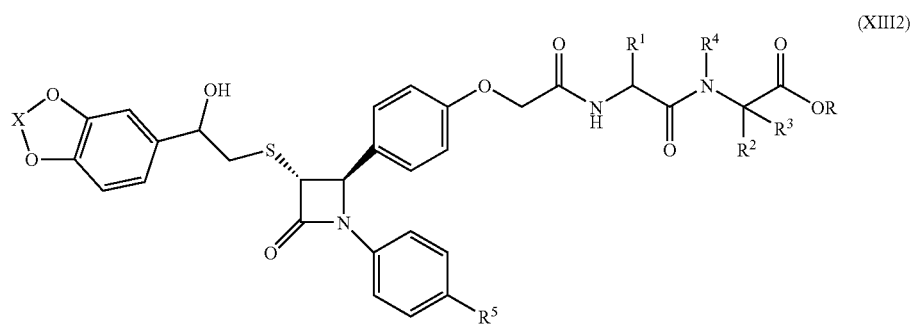

wherein L is a displaceable group; with a compound of formula (XII):

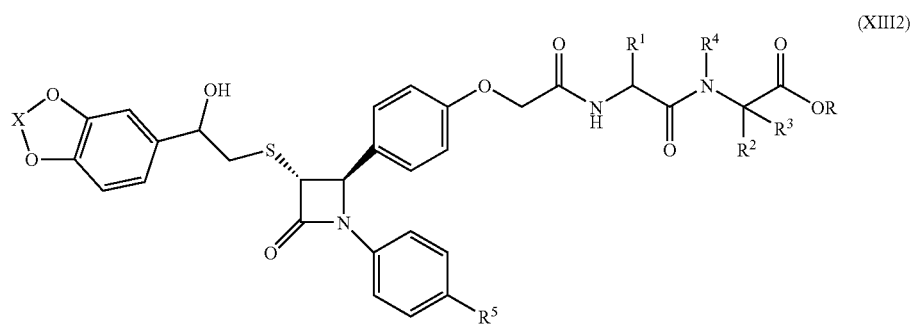

Process 7): De-Esterifying a Compound of Formula (XIII2)

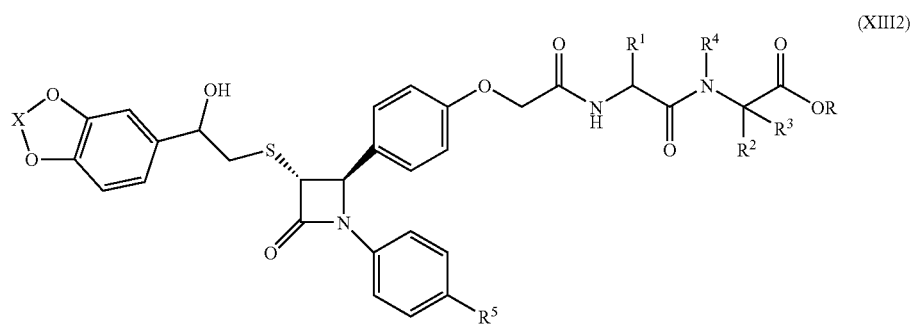

wherein the group C(O)OR is an ester group; and thereafter if necessary or desirable:

i) converting a compound of the formula (I2) into another compound of the formula (I2);

ii) removing any protecting groups;

iii) forming a pharmaceutically acceptable salt, solvate, solvate of such a salt or a prodrug; or iv) separating two or more enantiomers.

L is a displaceable group, suitable values for L are for example, a halogeno or sulphonyloxy group, for example a chloro, bromo, methanesulphonyloxy or toluene-4-sulphonyloxy group.

C(O)OR is an ester group, suitable values for C(O)OR are methoxycarbonyl, ethoxycarbonyl, t-butoxycarbonyl and benzyloxycarbonyl.

The starting materials used in the present invention can be prepared by modifications of the routes described in EP 0 792 264 B1. Alternatively they can be prepared by the following reactions.

Process 1): Alcohols of formula (II2) may be reacted with compounds of formula (III) in the presence of a base for example an inorganic base such as sodium carbonate, or an organic base such as Hunigs base, in the presence of a suitable solvent such as acetonitrile, dichloromethane or tetrahydrofuran at a temperature in the range of 0° C. to reflux, preferably at or near reflux.

Compounds of formula (II2) may be prepared according to the following scheme:
Scheme 1
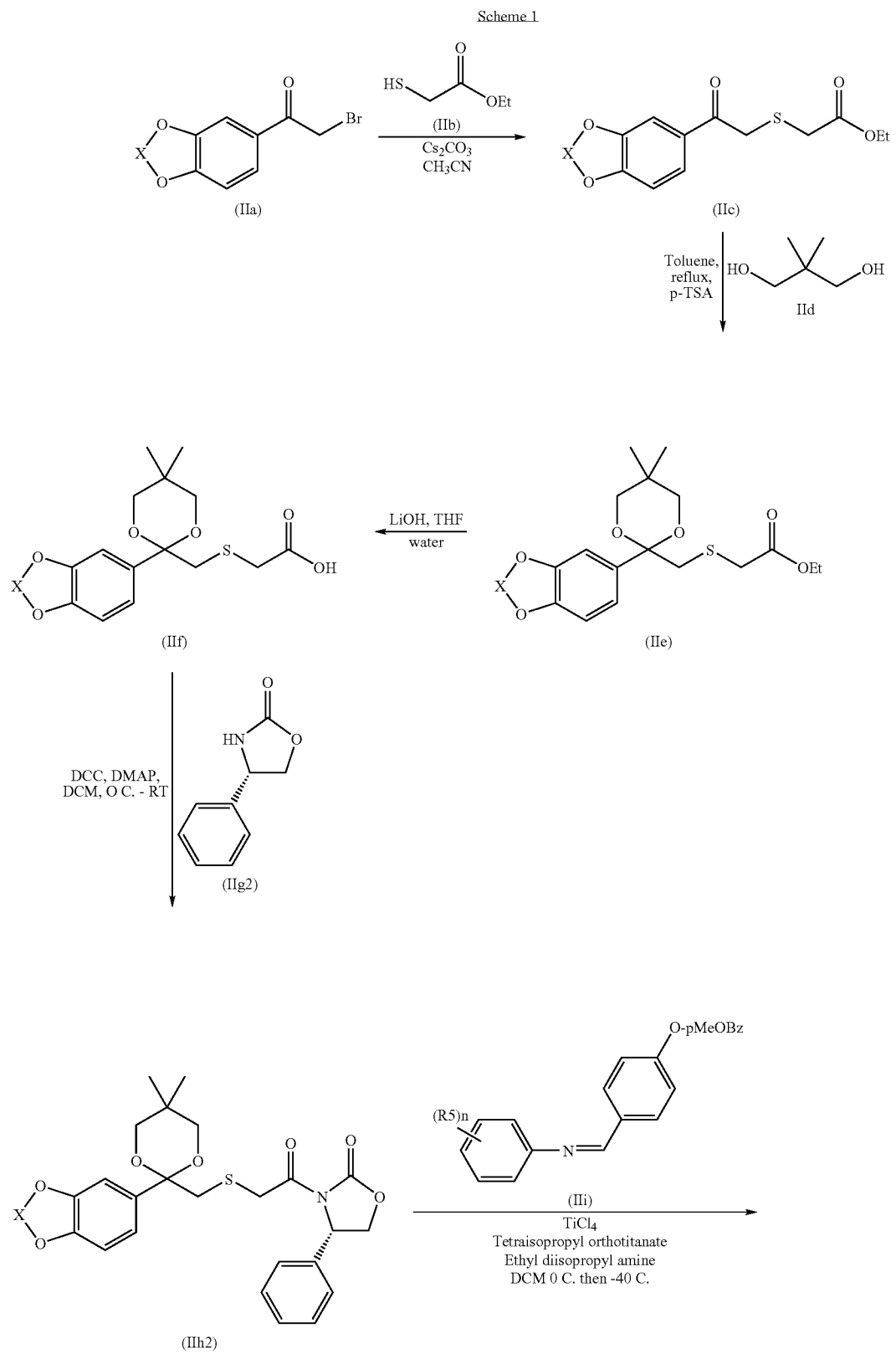

-continued
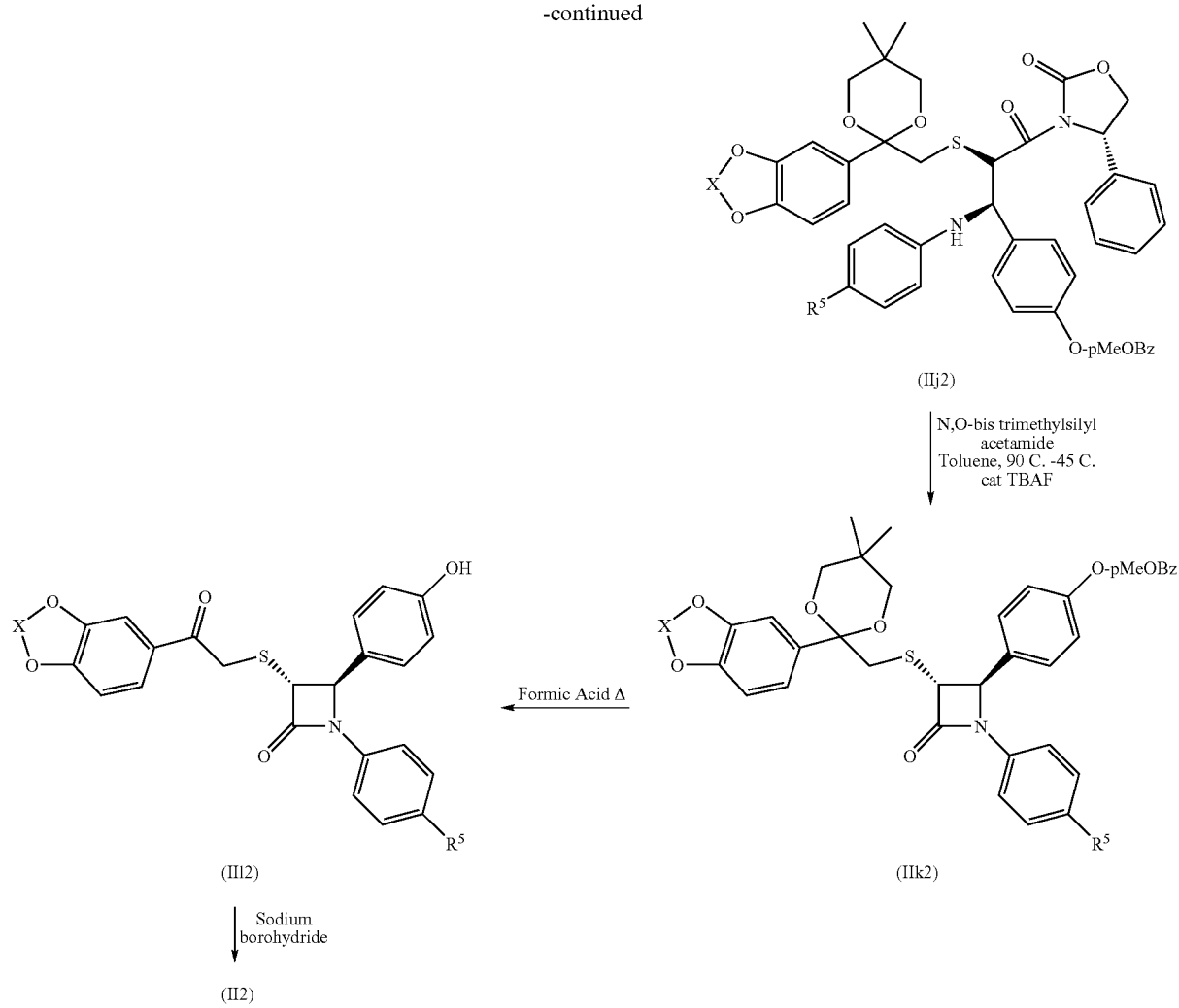
wherein pMeOBz is para methoxy benzyl.
Compounds of formula (IIb), (IId), (Iig2) and (III2) are commercially available compounds, or they are known in the literature, or they are prepared by standard processes known in the art.
A compound of formula (V) may also be reacted with a compound of formula (XIV).
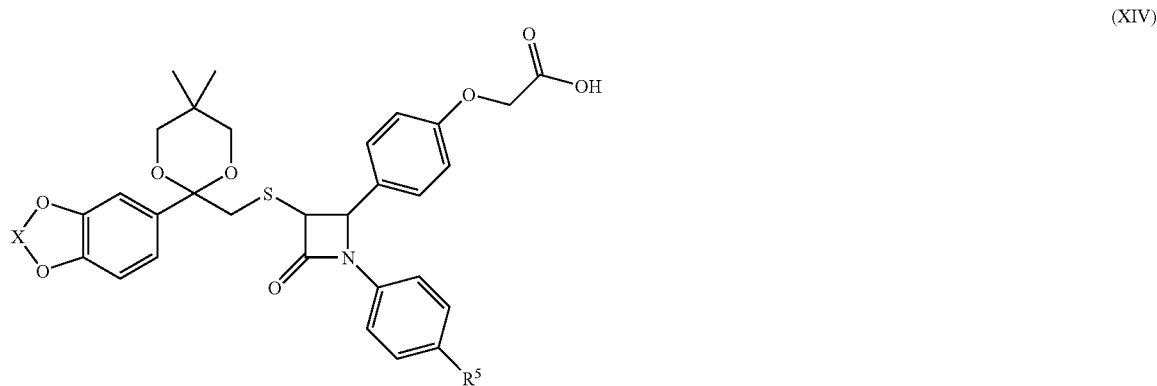

-continued
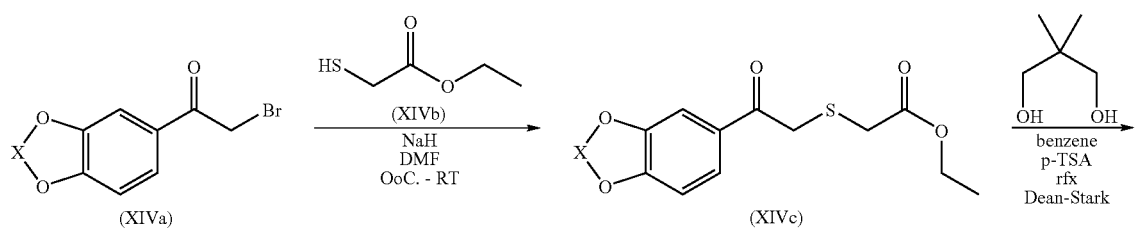
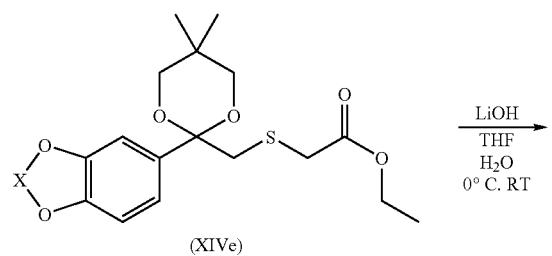
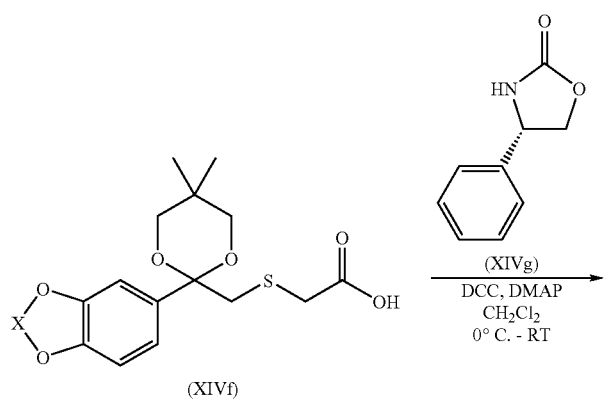
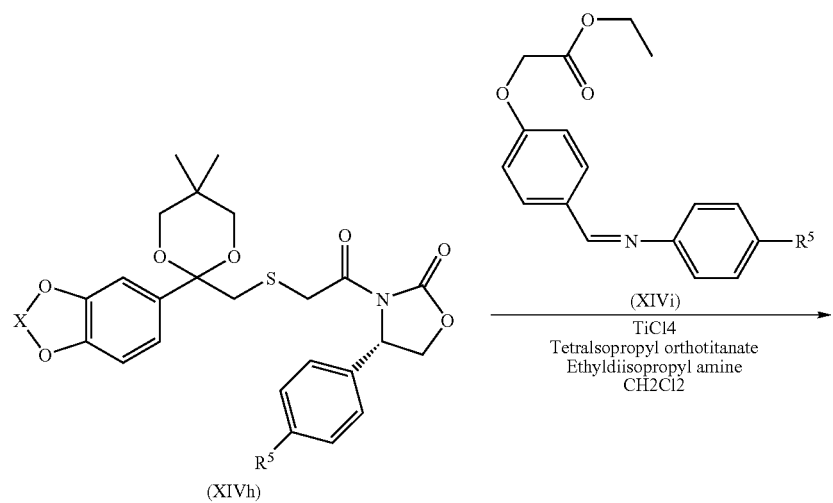

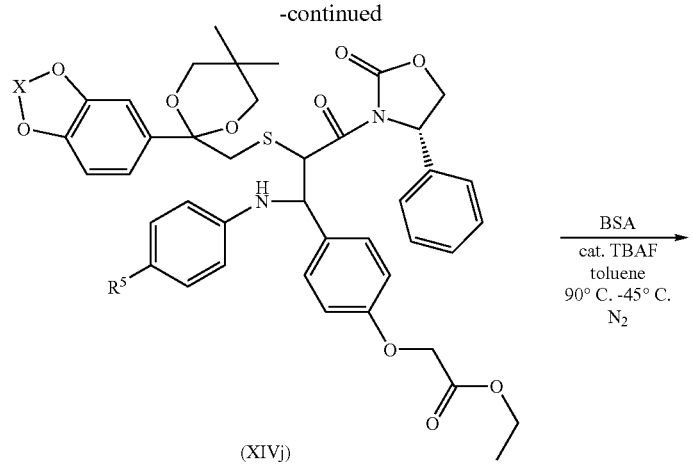
(XIVj)
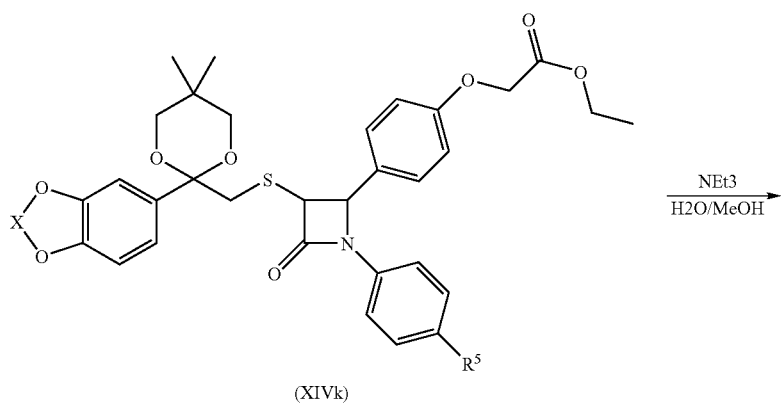
(XIVk)
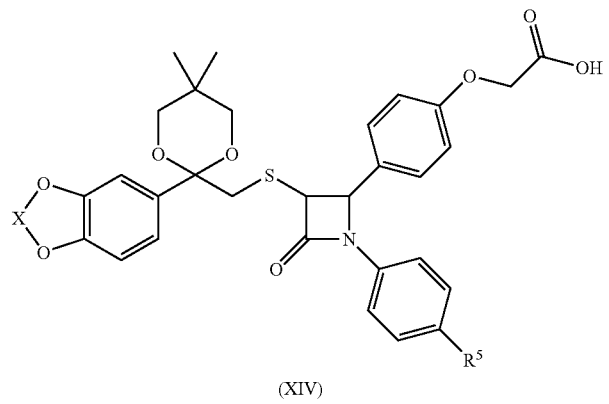
(XIV)
Compounds of formula XIVi may be prepared by the following route:
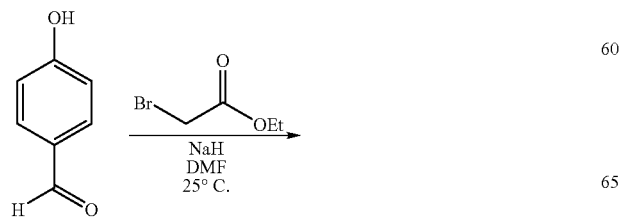

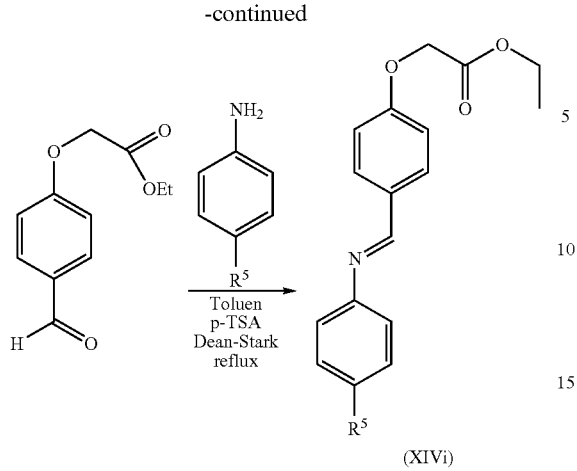
(XIVi)
A compound of formula (III2) may also be reacted with a compound of formula (XIV2).
Compounds of formula (XIV2) may be prepared according to the following route:
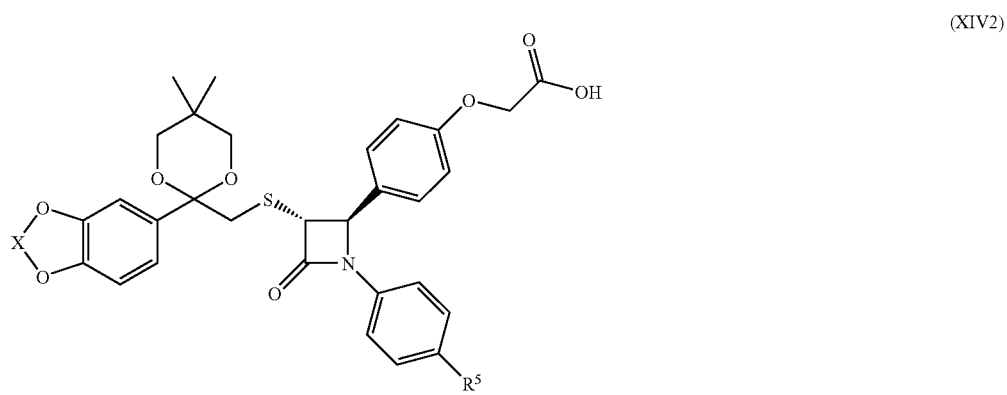
(XIV2)
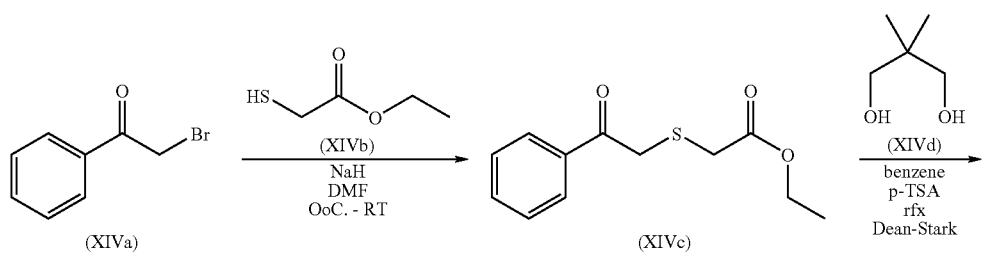
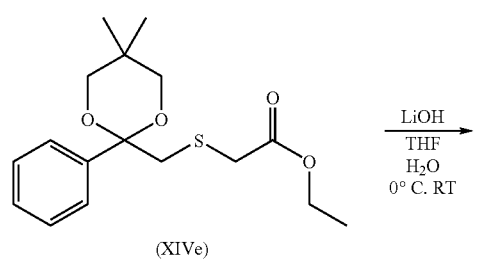

-continued
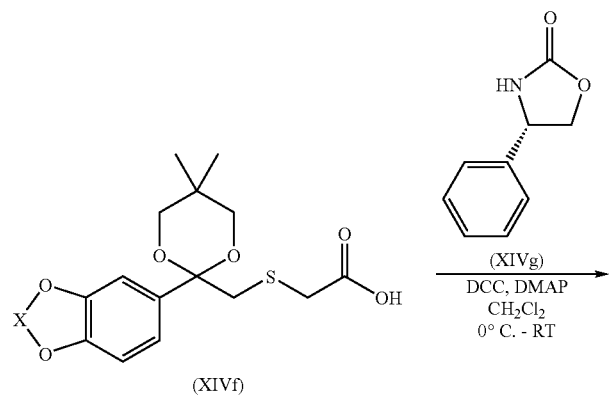
(XIVf)
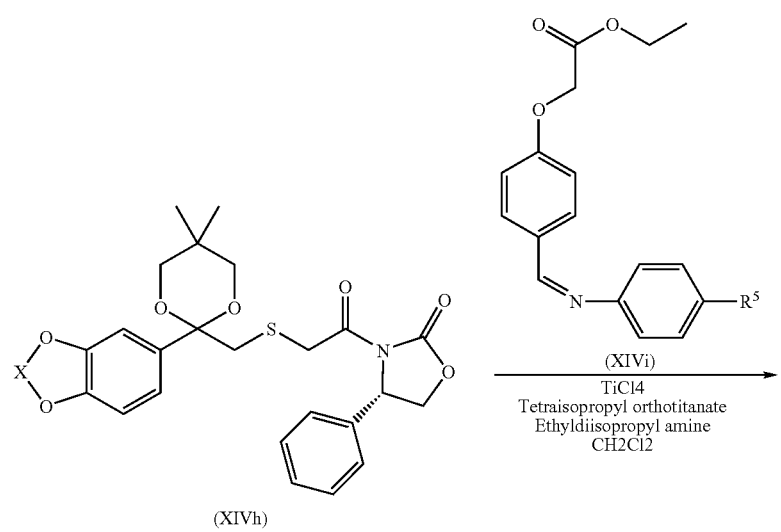
(XIVh)
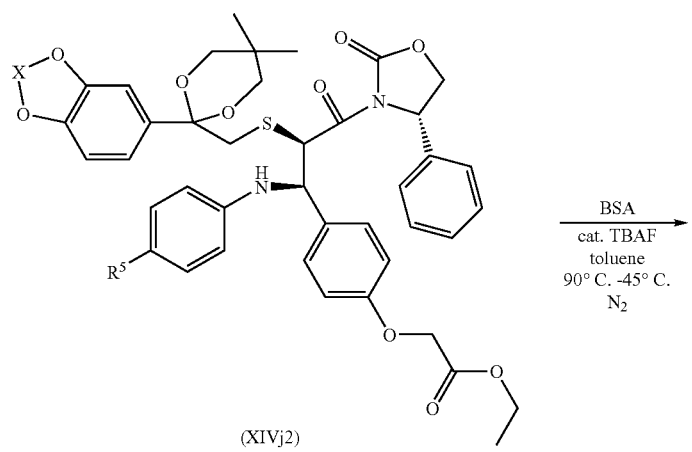
(XIVj2)

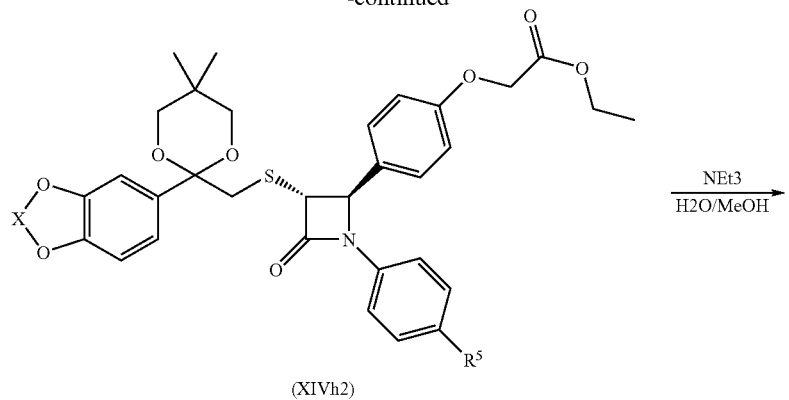
(XIVh2)
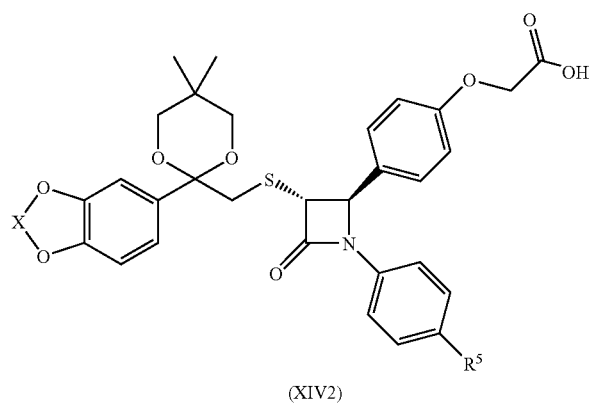
(XIV2)
A compound of formula (XV) may be reduced to a compound of formula (IV) or a compound of formula (XV) may be reacted with a compound of formula (V):
A compound of formula (XV2) may be reduced to a compound of formula (IV2) or a compound of formula (XV2) may be reacted with a compound of formula (V)
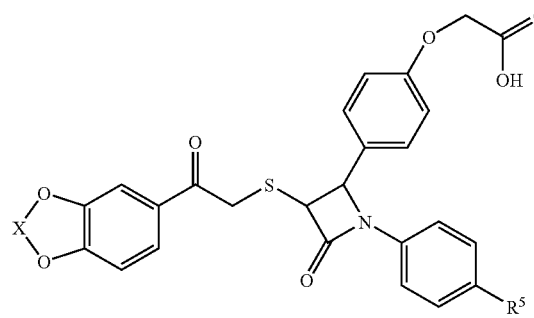
(XV)
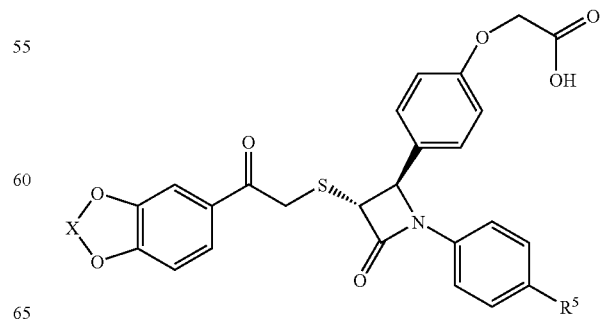
(XV2)

Compounds of formula (XV2) may be prepared according to the following route:
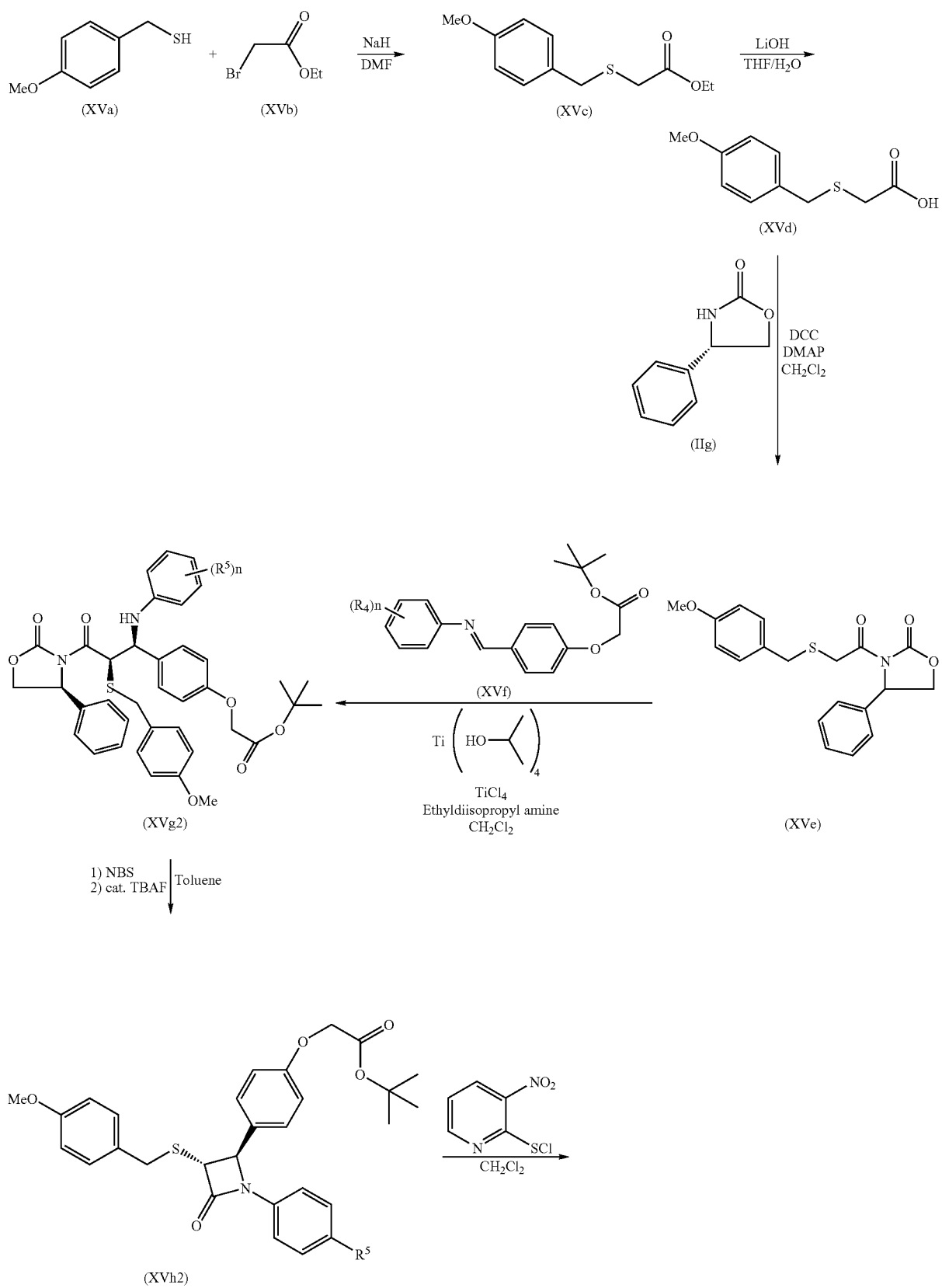

-continued
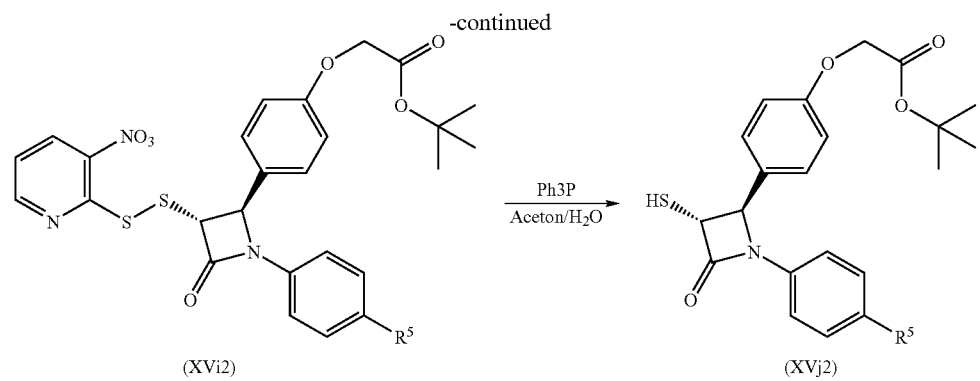
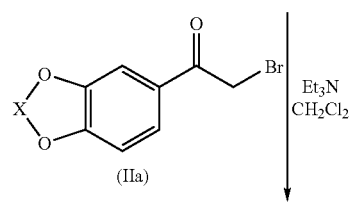
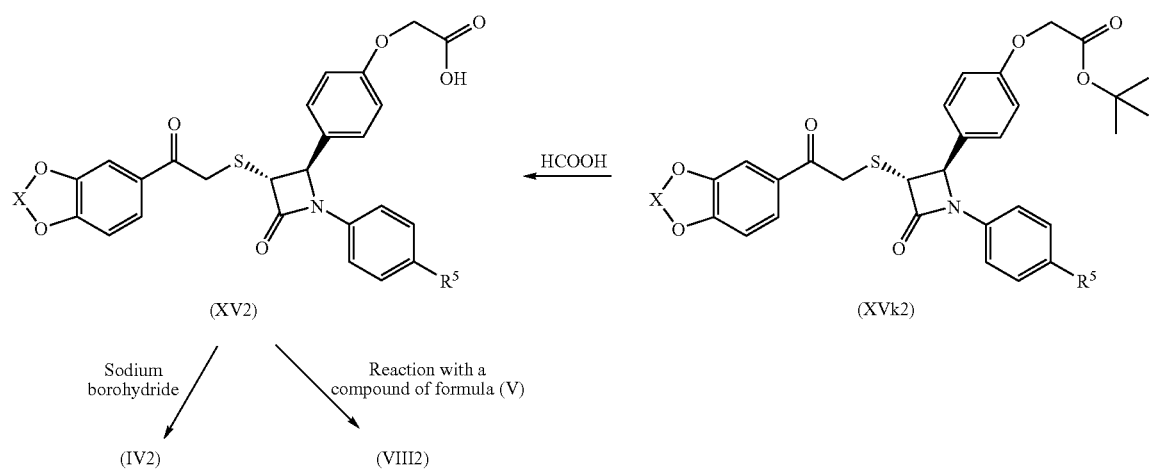
The steps in this scheme are not restricted to the reagents, conditions or protecting groups mentioned.
Compounds of formula (XV2) may be prepared according to the following scheme:
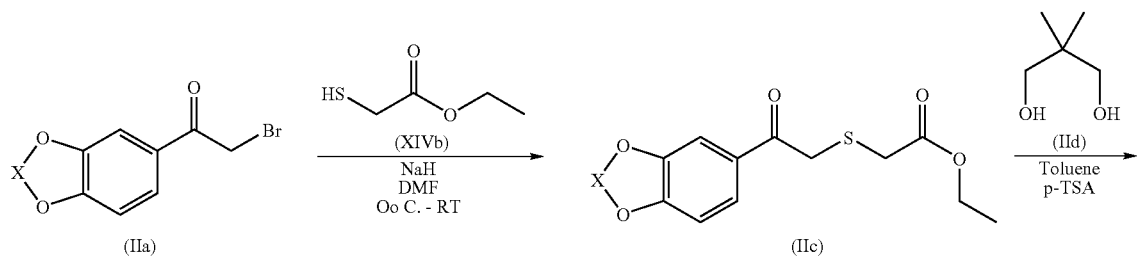

-continued
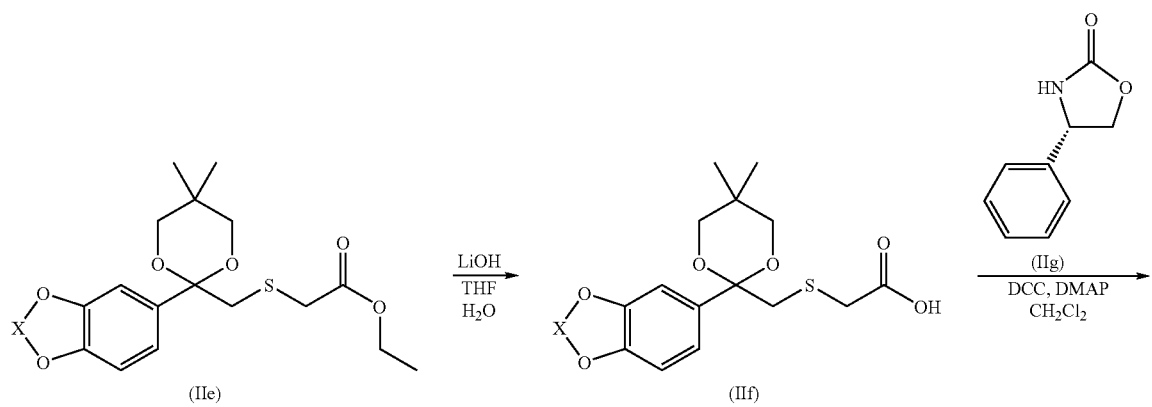
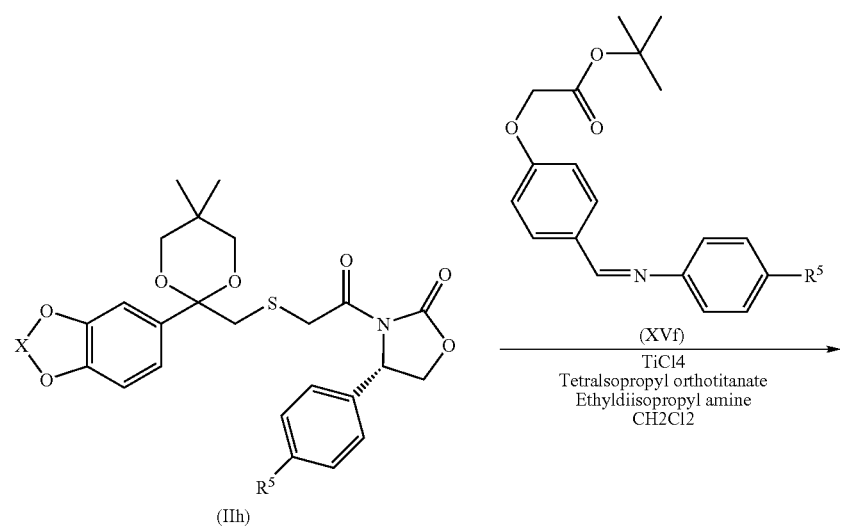
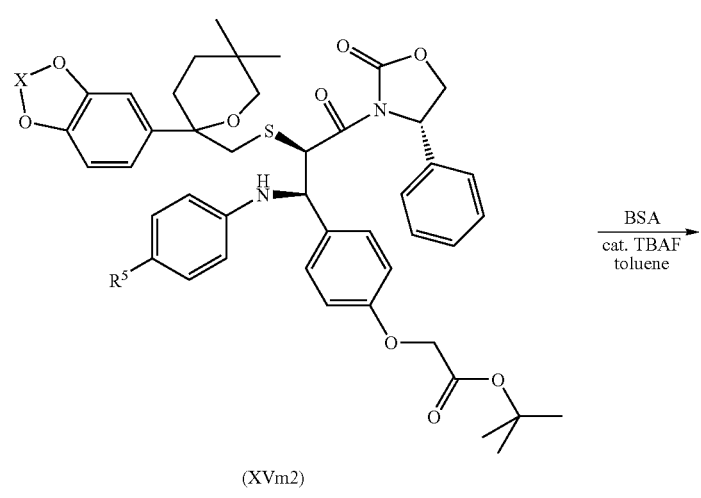

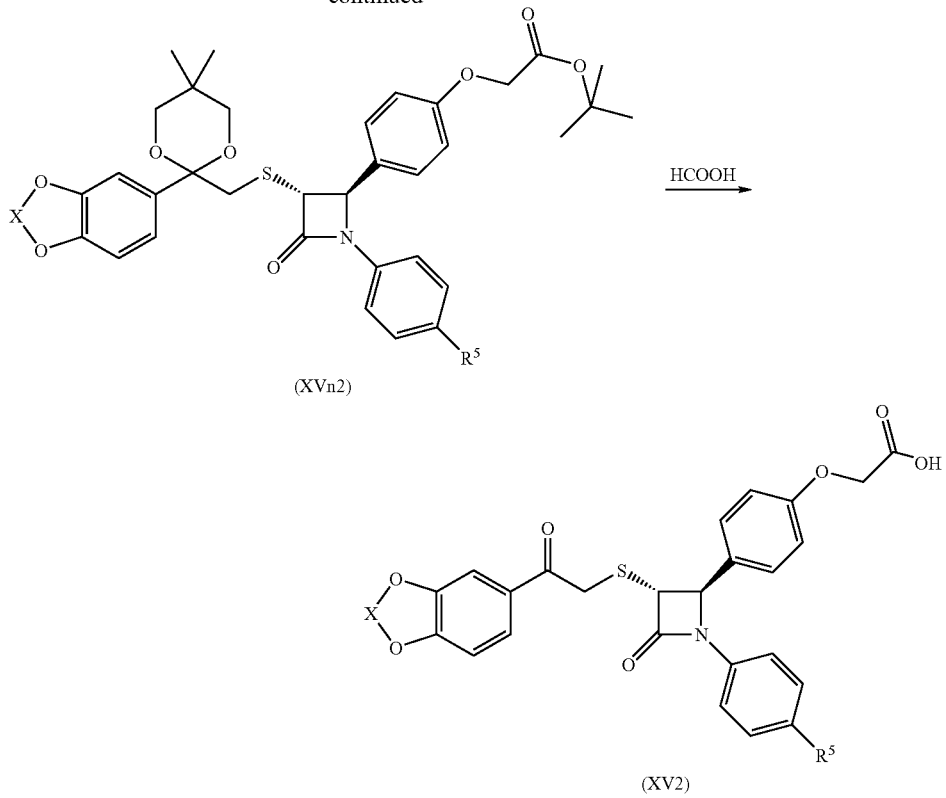

The steps in this scheme are not restricted to the reagents, conditions or protecting groups mentioned.

For XIV and (XV), and in an analogous manner for XIV2 and (XV2) both the following applies:

Process 2) and Process 3): Acids and amines may be coupled together in the presence of a suitable coupling reagent. Standard peptide coupling reagents known in the art can be employed as suitable coupling reagents, for example carbonyldiimidazole and dicyclohexyl-carbodiimide, optionally in the presence of a catalyst such as dimethylaminopyridine or 4-pyrrolidinopyridine, optionally in the presence of a base for example triethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of –40 to 40° C.

Suitable activated acid derivatives include acid halides, for example acid chlorides, and active esters, for example pentafluorophenyl esters. The reaction of these types of compounds with amines is well known in the art, for example they may be reacted in the presence of a base, such as those described above, and in a suitable solvent, such as those described above. The reaction may conveniently be performed at a temperature in the range of –40 to 40° C.

Acids of formula (IV) and (VI) may be prepared from compounds of formula (II) by reacting them with the appropriate, optionally protected, side chain using the conditions of Process 1). Alternatively, acids of formula (IV) and (VI) may be prepared by a modification of Scheme I.

Amines of formula (V) and (VII) are commercially available compounds, or they are known in the literature, or they are prepared by standard processes known in the art.

Process 4): Reduction of compounds of formula (VIII) could be performed with a hydride reagent such as sodium borohydride in a solvent such as methanol at temperatures suitable between –20-40° C.

Compounds of formula (VIII) can be prepared from compounds of formula (III), by deprotecting the benzyl group and performing Process 1. Alternatively compound (IIk) could be debenzylated, Process 1 could be performed and the resulting compound deprotected to reveal the ketone.

Process 5) and Process 6): these compounds may be reacted together in the presence of a base for example an inorganic base such as sodium carbonate, or an organic base such as Hunigs base, in the presence of a suitable solvent such as acetonitrile, dichloromethane or tetrahydrofuran at a temperature in the range of 0° C. to reflux, preferably at or near reflux.

Compounds of formula (IX) and (XI) may be prepared by an appropriate modification of Scheme 1.

Compounds of formula (X) and (XII) are commercially available compounds, or they are known in the literature, or they are prepared by standard processes known in the art.

Process 7): Esters of formula (XIII) may be deprotected under standard conditions such as those described below, for example a methyl or ethyl ester may be deprotected with sodium hydroxide in methanol at room temperature.

Compounds of formula (XIII) may be prepared by a modification of any of the processes described herein for the preparation of compounds of formula (I).

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1999). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

The invention further provides for a compound of the formula (XVI) or hydrolysable esters or amides thereof:

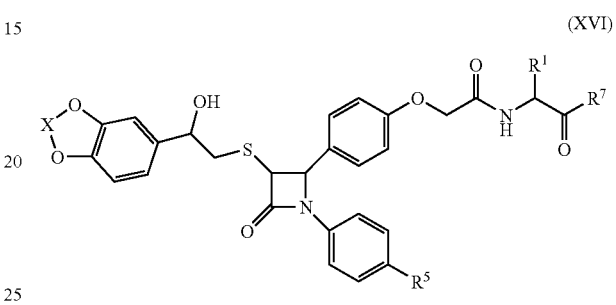

(XVI)

wherein $R^7$ is an hydroxy group or a $C_{1-4}$ alkoxy group. $R^1$, is as defined above regarding formula (I). A compound of formula (XVI) may be an intermediate to formula (I).

The invention further provides for a compound of the formula (XVI2) or hydrolysable esters or amides thereof:

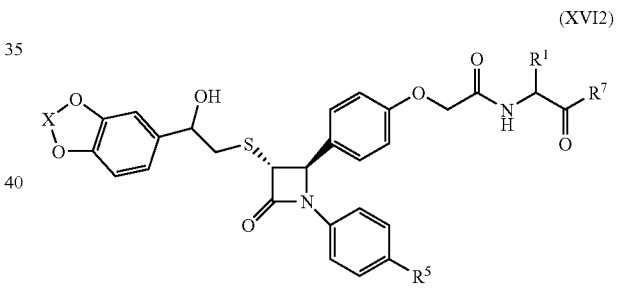

(XVI2)

wherein $R^7$ is an hydroxy group or a $C_{1-3}$ alkoxy group. $R^1$ is as defined above regarding formula (I). A compound of formula (XVI2) may be an intermediate to formula (I2).

As stated hereinbefore the compounds defined in the present invention possess cholesterol absorption inhibitory activity. These properties may be assessed, using the following biological tests.

In vivo Testing of Cholesterol Absorption Inhibitors (A)

C57BL/6 female mice were maintained on regular chow diet and housed in individual cages to collect faeces. Mice were fasted for 3 hours and then gavaged with vehicle or compound. Half an hour later the mice were gavaged with radiolabelled cholesterol. Six hours after the $^{14}C$-cholesterol gavage blood samples were taken via the tail and plasma prepared to determine how much cholesterol were absorbed. 24 hours after the gavage of $^{14}C$-cholesterol the mice were bled and plasma were prepared for analysis. Faeces were collected for 24 hours to assess absorption efficiency.

In vivo Testing of Cholesterol Absorption Inhibitors (B).

C57B116 female mice were maintained on regular chow diet and housed in individual cages to collect faeces. Mice were fasted for 3 hours and then gavaged with vehicle or compound. One to ten hours later the mice were gavaged with radiolabelled cholesterol. Six hours after the $^{14}$C-cholesterol gavage blood sample was taken via the tail and plasma prepared to determine how much cholesterol was absorbed. 24 hours after the gavage of $^{14}$C-cholesterol the mice were bled and plasma analysed for radioactivity. Faeces were also collected for 24 hours to assess absorption efficiency.

REFERENCES

1. E. A. Kirk, G. L. Moe, M. T. Caldwell, J. Å. Lernmark, D. L. Wilson, R. C. LeBoeuf. Hyper- and hypo-responsiveness to dietary fat and cholesterol among inbred mice: searching for level and variability genes. J. Lipid Res. 1995 36:1522-1532.
2. C. P. Carter, P. N. Howles, D. Y. Hui. Genetic variation in cholesterol absorption efficiency among inbred strains of mice. J. Nutr. 1997 127:1344-1348.
3. C. D. Jolley, J. M. Dietschy, S. D. Turley. Genetic differences in cholesterol absorption in 129/Sv and C57BL/6 mice: effect on cholesterol responsiveness. Am. J. Physiol. 1999 276:G1117-G1124.

Administration of 0.2 μmol/kg of Example 1 gave 61% inhibition of $^{14}$C-cholesterol absorption (procedure A). Administration of 0.2 μmol/kg of Example 3 gave 67% inhibition of $^{14}$C-cholesterol absorption (procedure A).

According to a further aspect of the invention there is provided a pharmaceutical composition which comprises a compound of formula (I), or a pharmaceutically acceptable salt, solvate, solvate of such a salt or a prodrug thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I), or a pharmaceutically acceptable salt, solvate, solvate of such a salt or a prodrug thereof, will normally be administered to a warm-blooded animal at a unit dose within the range of approximately 0.02-100 mg/kg, preferably 0.02-50 mg/kg, and this normally provides a therapeutically-effective dose. Preferably a daily dose in the range of 1-50 mg/kg, particularly 0.1-10 mg/kg is employed. In another aspect a daily dose in the rage of 0.01-20 mg/kg is employed. In one aspect of the invention the daily dose of a compound of formula (I) is less than or equal to 100 mg. However the daily dose will necessarily be varied depending upon the host treated, the particular route of administration, and the severity of the illness being treated. Accordingly the optimum dosage may be determined by the practitioner who is treating any particular patient. A unit dose form such as a tablet or capsule will usually contain, for example 1-250 mg of active ingredient.

According to a further aspect of the present invention there is provided a compound of the formula (I), or a pharmaceutically acceptable salt, solvate, solvate of such a salt or a prodrug thereof, as defined hereinbefore for use in a method of prophylactic or therapeutic treatment of a warm-blooded animal, such as man.

We have found that the compounds defined in the present invention, or a pharmaceutically acceptable salt, solvate, solvate of such a salt or a prodrug thereof, are effective cholesterol absorption inhibitors, and accordingly have value in the treatment of disease states associated with hyperlipidaemic conditions.

Thus according to this aspect of the invention there is provided a compound of the formula (I), or a pharmaceutically acceptable salt, solvate, solvate of such a salt or a prodrug thereof, as defined hereinbefore for use as a medicament.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the production of a cholesterol absorption inhibitory effect in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the production of a cholesterol absorption inhibitory effect in a warm-blooded animal, such as man.

Herein, where the production of a cholesterol absorption inhibitory effect or a cholesterol lowering effect is stated, suitably this relates to the treatment of hyperlipidaemic conditions in a warm-blooded animal, such as man. Additionally is relates to the treatment of dyslipidemic conditions and disorders such as hyperlipidaemia, hypertrigliceridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL) in a warm-blooded animal, such as man. Furthermore it relates to the treatment of different clinical conditions such as atherosclerosis, arteriosclerosis, arrhythmia, hyper-thrombotic conditions, vascular dysfunction, endothelial dysfunction, heart failure, coronary heart diseases, cardiovascular diseases, myocardial infarction, angina pectoris, peripheral vascular diseases, inflammation of cardiovascular tissues such as heart, valves, vasculature, arteries and veins, aneurysms, stenosis, restenosis, vascular plaques, vascular fatty streaks, leukocytes, monocytes and/or macrophage infiltration, intimal thickening, medial thinning, infectious and surgical trauma and vascular thrombosis, stroke and transient ischaemic attacks in a warm-blooded animal, such as man. It also relates to the treatment of atherosclerosis, coronary heart diseases, myocardial infarction, angina pectoris, peripheral vascular diseases, stroke and transient ischaemic attacks in a warm-blooded animal, such as man.

The production of a cholesterol absorption inhibitory effect or a cholesterol lowering effect also relates to a method of treating and/or preventing atherosclerotic lesions, a method of preventing plaque rupture and a method of promoting lesion regression. Furthermore it relates to a method of inhibiting monocytes-macrophage accumulation in atherosclerotic lesions, a method of inhibiting expression of matrix metalloproteinases in atherosclerotic lesions, a method of inhibiting the destabilization of atherosclerotic lesions, a method for preventing atherosclerotic plaque rupture and a method of treating unstable angina.

The production of a cholesterol absorption inhibitory effect or a cholesterol lowering effect also relates to a method of treating sitosterolemia.

Compounds of formula (I), or a pharmaceutically acceptable salt, solvate, solvate of such a salt or a prodrug thereof may also have value in the treatment or prevention of Alzheimer's Disease (see for example WO 02/096415). Therefore in a further aspect of the invention, there is provided a compound of formula (I), or a pharmaceutically acceptable salt, solvate, solvate of such a salt or a prodrug thereof, for use in the treatment or prevention of Alzheimer's Disease.

Compounds of formula (I), or a pharmaceutically acceptable salt, solvate, solvate of such a salt or a prodrug thereof may also have value in the treatment or prevention cholesterol associated tumors. Therefore in a further aspect of the invention, there is provided a compound of formula (I), or a pharmaceutically acceptable salt, solvate, solvate of such a salt or a prodrug thereof, for use in the treatment or prevention of cholesterol associated tumors.

Compounds of formula (I), or a pharmaceutically acceptable salt, solvate, solvate of such a salt or a prodrug thereof may also have value in the treatment or prevention of vascular inflammation (see for example WO 03/026644). Therefore in a further aspect of the invention, there is provided a compound of formula (I), or a pharmaceutically acceptable salt, solvate, solvate of such a salt or a prodrug thereof, for use in the treatment or prevention of vascular inflammation.

According to a further feature of this aspect of the invention there is provided a method for producing a cholesterol absorption inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof.

The cholesterol absorption inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. According to this aspect of the invention there is provided a pharmaceutical product comprising a compound of the formula (I), or a pharmaceutically acceptable salt, solvate, solvate of such a salt or a prodrug thereof, as defined hereinbefore and an additional cholesterol absorption inhibitory substance as defined hereinbefore and an additional hypolipidaemic agent for the conjoint treatment of hyperlipidaemia.

In another aspect of the invention, the compound of formula (I), or a pharmaceutically acceptable salt, solvate, solvate of such a salt or a prodrug thereof, may be administered in association with cholesterol biosynthesis inhibitors, or pharmaceutically acceptable salts, solvates, solvates of such salts or prodrugs thereof. Suitable cholesterol biosynthesis inhibitors include HMG Co-A reductase inhibitors, squalene synthesis inhibitors and squalene epoxidase inhibitors. Suitable squalene synthesis inhibitors are e.g squalestatin 1, TAK 475 and compounds described in WO2005012284. A suitable squalene epoxidase inhibitor is NB-598.

In this aspect of the invention, the compound of formula (I), or a pharmaceutically acceptable salt, solvate, solvate of such a salt or a prodrug thereof, may be administered in association with an HMG Co-A reductase inhibitor, or pharmaceutically acceptable salts, solvates, solvates of such salts or prodrugs thereof. Suitable HMG Co-A reductase inhibitors, pharmaceutically acceptable salts, solvates, solvates of such salts or prodrugs thereof are statins well known in the art. Particular statins are fluvastatin, lovastatin, pravastatin, simvastatin, atorvastatin, cerivastatin, bervastatin, dalvastatin, mevastatin and rosuvastatin, or a pharmaceutically acceptable salt, solvate, solvate of such a salt or a prodrug thereof. A further particular statin is pitavastatin, or a pharmaceutically acceptable salt, solvate, solvate of such a salt or a prodrug thereof. A particular statin is atorvastatin, or a pharmaceutically acceptable salt, solvate, solvate of such a salt or a prodrug thereof. A more particular statin is atorvastatin calcium salt. A further particular statin is rosuvastatin, or a pharmaceutically acceptable salt, solvate, solvate of such a salt or a prodrug thereof. A preferable particular statin is rosuvastatin calcium salt.

Therefore in an additional feature of the invention, there is provided a combination of a compound of formula (I), or a pharmaceutically acceptable salt, solvate, solvate of such a salt or a prodrug thereof and an HMG Co-A reductase inhibitor, or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof.

According to a further aspect of the present invention there is provided a kit comprising:
a) a compound of formula (I), or a pharmaceutically acceptable salt, solvate, solvate of such a salt or a prodrug thereof, in a first unit dosage form;
b) an HMG Co-A reductase inhibitor, or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) an HMG Co-A reductase inhibitor, or a pharmaceutically acceptable salt, solvate, solvate of such a salt or a prodrug thereof, in a second unit dosage form; and
c) container means for containing said first and second dosage forms.

According to another feature of the invention there is provided the use of a compound of the formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, in the manufacture of a medicament for use in the production of a cholesterol lowering effect.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an HMG Co-A reductase inhibitor, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

According to an additional further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of a matrix metalloproteinase inhibitor.

In another aspect of the invention, the compound of formula (I), or a pharmaceutically acceptable salt, solvate, solvate of such a salt or a prodrug thereof, may be administered in association with an ileal bile acid (IBAT) inhibitor or a pharmaceutically acceptable salt, solvate, solvate of such a salt or a prodrug thereof. Suitable compounds possessing IBAT inhibitory activity for use in combination with compounds of the present invention have been described, see for instance the compounds described in WO 93/16055, WO 94/18183, WO 94/18184, WO 94/24087, WO 96/05188, WO 96/08484, WO 96/16051, WO 97/33882, WO 98/07749, WO 98/38182, WO 98/40375, WO 98/56757, WO 99/32478, WO 99/35135, WO 99/64409, WO 99/64410, WO 00/01687, WO 00/20392, WO 00/20393, WO 00/20410, WO 00/20437, WO 00/35889, WO 01/34570, WO 00/38725, WO 00/38726, WO 00/38727, WO 00/38728, WO 00/38729, WO 00/47568, WO 00/61568, WO 01/66533, WO 01/68096, WO 01/68637, WO 02/08211, WO 02/50051, WO 03/018024, WO 03/040127, WO 03/043992, WO 03/061604, WO 04/020421, WO 04/076430, DE 19825804, JP 10072371, U.S. Pat. No. 5,070,103, EP 251 315, EP 417 725, EP 489 423, EP 549 967, EP 573 848, EP 624 593, EP 624 594, EP 624 595, EP 864 582, EP 869 121 and EP 1 070 703, WO 03/020710, WO 03/022825, WO 03/022830, WO 03/022286, WO 03/091232, WO 03/106482, and EP 597 107.

and the contents of these patent applications are incorporated herein by reference. Particularly the named examples of these patent applications are incorporated herein by reference. More particularly claim 1 of these patent application are incorporated herein by reference.

Other suitable classes of IBAT inhibitors for use in combination with compounds of the present invention are the benzothiepines, 1,2-benzothiazepines, 1,4-benzothiazepines and 1,5-benzothiazepines. A further suitable class of IBAT inhibitors is the 1,2,5-benzothiadiazepines.

One particular suitable compound possessing IBAT inhibitory activity for use in combination with compounds of the present invention is (3R,5R)-3-butyl-3-ethyl-1,1-dioxido-5-phenyl-2,3,4,5-tetrahydro-1,4-benzothiazepin-8-yl beta-D-glucopyranosiduronic acid (EP 864 582).

A further suitable compound possessing IBAT inhibitory activity for use in combination with compounds of the present invention is S-8921 (EP 597 107) and BARI-1741.

A further suitable IBAT inhibitor for use in combination with compounds of the present invention is the compound:

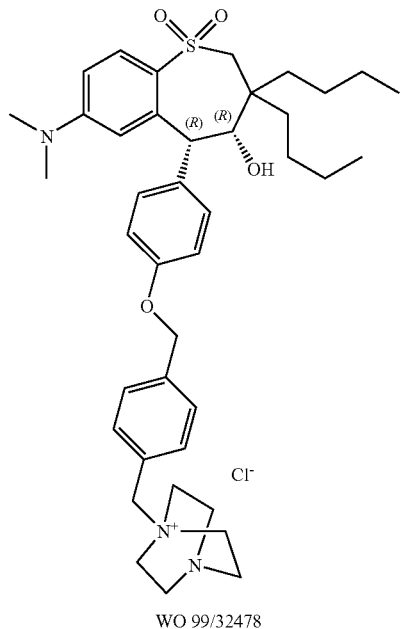

WO 99/32478

A particular MAT inhibitor for use in combination with compounds of the present invention is selected from any one of Examples 1-120 of WO 02/50051, or a pharmaceutically acceptable salt, solvate, solvate of such a salt or a prodrug thereof, and the compounds of Examples 1-120 are incorporated herein by reference. Claims 1-15 of WO 02/50051 are also incorporated herein by reference. A particular IBAT inhibitor selected from WO 02/50051 for use in combination with compounds of the present invention is selected from any one of:

1,1-dioxo-3,3-dibutyl-5-phenyl-7-methylthio-8-(N-{(R)-1'-phenyl-1'-[N'-(carboxymethyl) carbamoyl]methyl} carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(carboxymethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-1'-phenyl-1'[N'-(2-sulphoethyl)carbamoyl]methyl}carbamoylmethoxy)-2,3,4,5-tetrahydro-1,5-benzothiazepine;

1,1-dioxo-3-butyl-3-ethyl-5-phenyl-7-methylthio-8-(N-{(R)-1'-phenyl-1'-[N'-(2-sulphoethyl)carbamoyl]methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-sulphoethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-sulphoethyl) carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl]-4-hydroxybenzyl}carbamoylmethoxy)-2,3,4,5-tetrahydro-1,5-benzothiazepine;
1,1-dioxo-3-butyl-3-ethyl-5-phenyl-7-methylthio-8-(N-{(R)-α-[N'-(5-carboxypentyl) carbamoyl]benzyl}carbamoylmethoxy)-2,3,4,5-tetrahydro-1,5-benzothiazepine;
1,1-dioxo-3,3-dibutyl-5-phenyl-7-methylthio-8-(N-{(R)-α-[N'-(2-carboxyethyl)carbamoyl]benzyl}carbamoylmethoxy)-2,3,4,5-tetrahydro-1,5-benzothiazepine;
1,1-dioxo-3,3-dibutyl-5-phenyl-7-methylthio-8-(N-{α-[N'-(2-sulphoethyl)carbamoyl]-2-fluorobenzyl}carbamoylmethoxy)-2,3,4,5-tetrahydro-1,5-benzothiazepine;
1,1-dioxo-3-butyl-3-ethyl-5-phenyl-7-methylthio-8-(N-{(R)-α-[N'-(R)-(2-hydroxy-1-carboxyethyl)carbamoyl]benzyl}carbamoylmethoxy)-2,3,4,5-tetrahydro-1,5-benzothiazepine;
1,1-dioxo-3,3-dibutyl-5-phenyl-7-methylthio-8-(N-{(R)-α-[N'-(R)-(2-hydroxy-1-carboxyethyl)carbamoyl]benzyl}carbamoylmethoxy)-2,3,4,5-tetrahydro-1,5-benzothiazepine;
1,1-dioxo-3,3-dibutyl-5-phenyl-7-methylthio-8-[N-[(R)-α-(N'-{(R)-1-[N''-(R)-(2-hydroxy-1-carboxyethyl)carbamoyl]-2-hydroxyethyl}carbamoyl)benzyl]carbamoylmethoxy]-2,3,4,5-tetrahydro-1,5-benzothiazepine;
1,1-dioxo-3-butyl-3-ethyl-5-phenyl-7-methylthio-8-(N-{α-[N'-(carboxymethyl)carbamoyl]benzyl}carbamoylmethoxy)-2,3,4,5-tetrahydro-1,5-benzothiazepine;
1,1-dioxo-3-butyl-3-ethyl-5-phenyl-7-methylthio-8-(N-{α-[N'-((ethoxy)(methyl)phosphoryl-methyl)carbamoyl]benzyl}carbamoylmethoxy)-2,3,4,5-tetrahydro-1,5-benzothiazepine;
1,1-dioxo-3-butyl-3-ethyl-5-phenyl-7-methylthio-8-{N-[(R)-α-(N'-{2-[(hydroxy)(methyl)phosphoryl]ethyl} carbamoyl)benzyl]carbamoylmethoxy}-2,3,4,5-tetrahydro-1,5-benzothiazepine;
1,1-dioxo-3,3-dibutyl-5-phenyl-7-methylthio-8-(N-{(R)-α-[N'-(2-methylthio-1-carboxyethyl)carbamoyl]benzyl}carbamoylmethoxy)-2,3,4,5-tetrahydro-1,5-benzothiazepine;
1,1-dioxo-3,3-dibutyl-5-phenyl-7-methylthio-8-{N-[(R)-α-(N'-{2-[(methyl)(ethyl) phosphoryl]ethyl}carbamoyl)-4-hydroxybenzyl]carbamoylmethoxy}-2,3,4,5-tetrahydro-1,5-benzothiazepine;
1,1-dioxo-3,3-dibutyl-5-phenyl-7-methylthio-8-{N-[(R)-α-(N'-{2-[(methyl)(hydroxy) phosphoryl]ethyl}carbamoyl)-4-hydroxybenzyl]carbamoylmethoxy}-2,3,4,5-tetrahydro-1,5-benzothiazepine;
1,1-dioxo-3,3-dibutyl-5-phenyl-7-methylthio-8-(N-{(R)-α-[(R)-N'-(2-methylsulphinyl-1-carboxyethyl)carbamoyl]benzyl}carbamoylmethoxy)-2,3,4,5-tetrahydro-1,5-benzothiazepine; and
1,1-dioxo-3,3-dibutyl-5-phenyl-7-methoxy-8-[N-{(R)-α-[N'-(2-sulphoethyl)carbamoyl]-4-hydroxybenzyl}carbamoylmethoxy]-2,3,4,5-tetrahydro-1,5-benzothiazepine;
or a pharmaceutically acceptable salt, solvate, solvate of such a salt or a prodrug thereof.

A particular IBAT inhibitor for use in combination with compounds of the present invention is selected from any one of Examples 1-44 of WO 03/020710, or a pharmaceutically acceptable salt, solvate, solvate of such a salt or a prodrug thereof, and the compounds of Examples 1-44 are incorporated herein by reference. Claims 1-10 of WO 03/020710 are also incorporated herein by reference. A particular IBAT inhibitor selected from WO 03/020710 for use in combination with compounds of the present invention is selected from any one of:
1,1-dioxo-3,3-dibutyl-5-phenyl-7-methylthio-8-(N-{(R)-α-[N'-(2-(S)-3-(R)-4-(R)-5-(R)-2,3,4,5,6-pentahydroxyhexyl)carbamoyl]benzyl}carbamoylmethoxy)-2,3,4,5-tetrahydro-1,5-benzothiazepine;
1,1-dioxo-3-butyl-3-ethyl-5-phenyl-7-methylthio-8-(N-{(R)-α-[N'-(2-(S)-3-(R)-4-(R)-5-(R)-2,3,4,5,6-pentahydroxyhexyl)carbamoyl]benzyl}carbamoylmethoxy)-2,3,4,5-tetrahydro-1,5-benzothiazepine;
1,1-dioxo-3-butyl-3-ethyl-5-phenyl-7-methylthio-8-(N-{(R)-α-[N'-((S)-1-carbamoyl-2-hydroxyethyl)carbamoyl]benzyl}carbamoylmethoxy)-2,3,4,5-tetrahydro-1,5-benzothiazepine;
1,1-dioxo-3-butyl-3-ethyl-5-phenyl-7-methylthio-8-(N-{(R)-α-[N'-(hydroxycarbamoyl-methyl)carbamoyl]benzyl}carbamoylmethoxy)-2,3,4,5-tetrahydro-1,5-benzothiazepine;
1,1-dioxo-3-butyl-3-ethyl-5-phenyl-7-methylthio-8-[N-((R)-α-{N-[2-(N'-pyrimidin-2-ylureido)ethyl]carbamoyl}benzyl)carbamoylmethoxy]-2,3,4,5-tetrahydro-1,5-benzothiazepine;
1,1-dioxo-3-butyl-3-ethyl-5-phenyl-7-methylthio-8-[N-((R)-α-{N'-[2-(N'-pyridin-2-ylureido)ethyl]carbamoyl}benzyl)carbamoylmethoxy}-2,3,4,5-tetrahydro-1,5-benzothiazepine;
1,1-dioxo-3-butyl-3-ethyl-5-phenyl-7-methylthio-8-(N-{(R)-α-[N'-(1-t-butoxycarbonylpiperidin-4-ylmethyl)carbamoyl]benzyl}carbamoylmethoxy)-2,3,4,5-tetrahydro-1,5-benzothiazepine;
1,1-dioxo-3-butyl-3-ethyl-5-phenyl-7-methylthio-8-(N-{(R)-α-[N'-(2,3-dihydroxypropyl)carbamoyl]benzyl}carbamoylmethoxy)-2,3,4,5-tetrahydro-1,5-benzothiazepine;
1,1-dioxo-3-butyl-3-ethyl-5-phenyl-7-methylthio-8-[N-((R)-α-[N'[2-(3,4-dihydroxyphenyl)-2-methoxyethyl]carbamoyl]benzyl)carbamoylmethoxy]-2,3,4,5-tetrahydro-1,5-benzothiazepine
1,1-dioxo-3-butyl-3-ethyl-5-phenyl-7-methylthio-8-(N-{(R)-α-[N'-(2-aminoethyl)carbamoyl]benzyl}carbamoylmethoxy)-2,3,4,5-tetrahydro-1,5-benzothiazepine;
1,1-dioxo-3-butyl-3-ethyl-5-phenyl-7-methylthio-8-(N-{(R)-α-[N'-(piperidin-4-ylmethyl) carbamoyl]benzyl}carbamoylmethoxy)-2,3,4,5-tetrahydro-1,5-benzothiazepine; or
1,1-dioxo-3-butyl-3-ethyl-5-phenyl-7-methylthio-8-(N-{(R)-α-[N'-(2-N,N-dimethylaminosulphamoylethyl)carbamoyl]benzyl}carbamoylmethoxy)-2,3,4,5-tetrahydro-1,5-benzothiazepine;
or a pharmaceutically acceptable salt, solvate, solvate of such a salt or a prodrug thereof.

A particular IBAT inhibitor for use in combination with compounds of the present invention is selected from any one of Examples 1-7 of WO 03/022825, or a pharmaceutically acceptable salt, solvate; solvate of such a salt or a prodrug thereof, and the compounds of Examples 1-7 are incorporated herein by reference. Claims 1-8 of WO 03/022825 are also incorporated herein by reference. A particular IBAT inhibitor selected from WO 03/022825 for use in combination with compounds of the present invention is selected from any one of:

1,1-dioxo-3(R)-3-butyl-3-ethyl-5-(R)-5-phenyl-8-[N-((R)-α-carboxybenzyl) carbamoylmethoxy]-2,3,4,5-tetrahydro-1,4-benzothiazepine;

1,1-dioxo-3(S)-3-butyl-3-ethyl-5-(S)-5-phenyl-8-[N-((R)-α-carboxybenzyl) carbamoylmethoxy]-2,3,4,5-tetrahydro-1,4-benzothiazepine;

1,1-dioxo-3(R)-3-butyl-3-ethyl-5-(R)-5-phenyl-8-(N-{(R)-α-[N-(carboxymethyl)carbamoyl]benzyl}carbamoylmethoxy)-2,3,4,5-tetrahydro-1,4-benzothiazepine;

1,1-dioxo-3(S)-3-butyl-3-ethyl-5-(S)-5-phenyl-8-(N-{(R)-α-[N-(carboxymethyl)carbamoyl]benzyl}carbamoylmethoxy)-2,3,4,5-tetrahydro-1,4-benzothiazepine;

3,5-trans-1,1-dioxo-3-ethyl-3-butyl-5-phenyl-7-bromo-8-(N-{(R)-α-[N'-(carboxymethyl)carbamoyl]benzyl}carbamoylmethoxy)-2,3,4,5-tetrahydro-1,4-benzothiazepine;

3,5-trans-1,1-dioxo-3-(S)-3-ethyl-3-butyl-4-hydroxy-5-(S)-5-phenyl-7-bromo-8-(N-{(R)-α-[N'-(carboxymethyl)carbamoyl]benzyl}carbamoylmethoxy)-2,3,4,5-tetrahydro-1,4-benzothiazepine 3,5-trans-1,1-dioxo-3-(R)-3-ethyl-3-butyl-4-hydroxy-5-(R)-5-phenyl-7-bromo-8-(N-{(R)-α-[N'-(carboxymethyl)carbamoyl]benzyl}carbamoylmethoxy)-2,3,4,5-tetrahydro-1,4-benzothiazepine;

3,5-trans-1,1-dioxo-3-ethyl-3-butyl-5-phenyl-7-methylthio-8-(N-{(R)-α-[N-(carboxymethyl)carbamoyl]benzyl}carbaraoylmethoxy)-2,3,4,5-tetrahydro-1,4-benzothiazepine;

3,5-trans-1,1-dioxo-3-ethyl-3-butyl-5-phenyl-7-methylthio-8-(N-{(R)-α-[N-(2-sulphoethyl)carbamoyl]-4-hydroxybenzyl}carbamoylmethoxy)-2,3,4,5-tetrahydro-1,4-benzothiazepine ammonia salt;

1,1-dioxo-3-(S)-3-ethyl-3-butyl-5-(S)-5-phenyl-7-methylthio-8-(N-{(R)-α-[N-(carboxymethyl)carbamoyl]benzyl}carbamoylmethoxy)-2,3,4,5-tetrahydro-1,4-benzothiazepine diethylamine salt; and 1,1-dioxo-3-(R)-3-ethyl-3-butyl-5-(R)-5-phenyl-7-methylthio-8-(N-{(R)-α-[N-(carboxymethyl)carbamoyl]benzyl}carbamoylmethoxy)-2,3,4,5-tetrahydro-1,4-benzothiazepine diethylamine salt;

or a pharmaceutically acceptable salt, solvate, solvate of such a salt or a prodrug thereof.

A particular IBAT inhibitor for use in combination with compounds of the present invention is selected from any one of Examples 1-4 of WO 03/022830, or a pharmaceutically acceptable salt, solvate, solvate of such a salt or a prodrug thereof, and the compounds of Examples 1-4 are incorporated herein by reference. Claims 1-8 of WO 03/022830 are also incorporated herein by reference. A particular IBAT inhibitor selected from WO 03/022830 for use in combination with compounds of the present invention is selected from any one of:

1,1-dioxo-3-butyl-3-ethyl-4-hydroxy-5-phenyl-7-(N-{(R)-α-[N-(carboxymethyl)carbamoyl]benzyl}carbamoylmethylthio)-2,3,4,5-tetrahydrobenzothiepine 1,1-dioxo-3-butyl-3-ethyl-4-hydroxy-5-phenyl-7-(N-{(R)-α-[N-(2-sulphoethyl)carbamoyl]-4-hydroxybenzyl}carbamoylmethylthio)-2,3,4,5-tetrahydrobenzothiepine ammonia salt 1,1-dioxo-3-butyl-3-ethyl-4-hydroxy-5-phenyl-7-(N-{(R)-[α-(carboxy)-2-fluorobenzyl]carbamoylmethylthio}-2,3,4,5-tetrahydrobenzothiepine; and 1,1-dioxo-3-butyl-3-ethyl-4-hydroxy-5-phenyl-7-{N-[1-(carboxy)-1-(thien-2-yl)methyl]carbamoylmethylthio}-2,3,4,5-tetrahydrobenzothiepine or a pharmaceutically acceptable salt, solvate, solvate of such a salt or a prodrug thereof.

A particular IBAT inhibitor for use in combination with compounds of the present invention is selected from any one of Examples 1-39 of WO 03/022286, or a pharmaceutically acceptable salt, solvate, solvate of such a salt or a prodrug thereof, and the compounds of Examples 1-39 are incorporated herein by reference. Claims 1-10 of WO 03/022286 are also incorporated herein by reference. A particular IBAT inhibitor selected from WO 03/022286 for use in combination with compounds of the present invention is selected from any one of:

1,1-dioxo-3,3-dibutyl-5-phenyl-7-methylthio-8-(N-{(R)-α-[N-((R)-1-carboxy-2-methylthio-ethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxybutyl) carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxypropyl) carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl) carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-(2-sulphoethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((R)-1-carboxy-2-methylthioethyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α[N-{(S)-1-[N-((S)-2-hydroxy-1-carboxyethyl)carbamoyl]propyl}carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxypropyl) carbamoyl]-4-hydroxybenzyl}carbamoylmethoxy)-2,3,4,5-tetrahydro-1,2,5-benzothiadiazepine; and 1,1-dioxo-3,3-dibutyl-5-phenyl-7-methylthio-8-[N-((R)-α-carboxy-4-hydroxybenzyl)carbamoylmethoxy]-2,3,4,5-tetrahydro-1,2,5-benzothiadiazepine;

or a pharmaceutically acceptable salt, solvate, solvate of such a salt or a prodrug thereof.

A particular IBAT inhibitor for use in combination with compounds of the present invention is selected from any one of Examples 1-7 of WO 03/091232, or a pharmaceutically acceptable salt, solvate, solvate of such a salt or a prodrug thereof, and the compounds of Examples 1-7 are incorporated herein by reference. Claims 1-10 of WO 03/091232 are also incorporated herein by reference. A particular IBAT inhibitor selected from WO 03/091232 for use in combination with compounds of the present invention is selected from any one of:

1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl)carbamoyl]benzyl}carbamoylmethoxy)-2,3,4,5-tetrahydro-1,2,5-benzothialiazepine;

1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl)carbamoyl]-4-hydroxybenzyl}carbamoylmethoxy)-2,3,4,5-tetrahydro-1,2,5-benzothiadiazepine;

1,1-Dioxo-3,3-dibutyl-5-phenyl-7-methylthio-8-[N-((R/S)-α-{N-[1-(R)-2-(S)-1-hydroxy-1-(3,4-dihydroxyphenyl)prop-2-yl]carbamoyl}-4-hydroxybenzyl)carbamoylmethoxy]-2,3,4,5-tetrahydro-1,2,5-benzothiadiazepine;

1,1-Dioxo-3,3-dibutyl-5-phenyl-7-methylthio-8-{N-((R)-α-[N-{2-(S)-[N-(carbamoylmethyl) carbamoyl]pyrrolidin-1-ylcarbonylmethyl}carbamoyl)benzyl]carbamoylmethoxy}-2,3,4,5-tetrahydro-1,2,5-benzothiadiazepine;

1,1-Dioxo-3,3-dibutyl-5-phenyl-7-methylthio-8-[N-((R)-α-{N-[2-(3,4,5-trihydroxyphenyl)ethyl]carbamoyl}benzyl)carbamoylmethoxy]-2,3,4,5-tetrahydro-1,2,5-benzothiadiazepine; and 1,1-Dioxo-3,3-dibutyl-5-phenyl-7-methylthio-8-(N-{(R)-α-[N-(2-(R)-3-(S)-4-(S)-5-(R)-3,4,5,6-tetrahydroxytetrahydropyran-2-ylmethyl)carbamoyl]benzyl}carbamoylmethoxy)-2,3,4,5-tetrahydro-1,2,5-benzothiadiazepine;

or a pharmaceutically acceptable salt, solvate, solvate of such a salt or a prodrug thereof. Further suitable compounds possessing IBAT inhibitory for use in combination with compounds of the present invention are disclosed in WO 03/106482

Suitable IBAT inhibitors having the above structure for use in combination with compounds of the present invention are selected from any one of:

1,1-dioxo-3,3-dibutyl-5-phenyl-7-methylthio-8-(N-{(R)-α-[N'-((S)-1-carboxyethyl) carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxypropyl) carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxybutyl) carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylpropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylbutyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-methylbutyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-hydroxypropyl)carbamoyl]benzyl carbamoyl}methoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-mesylethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'4(S)-1-carboxy-3-methylsulphonylpropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-mesylpropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxyethyl) carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxypropyl) carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxybutyl) carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylpropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylbutyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-methylbutyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-hydroxyethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-hydroxypropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N-((S)-1-carboxy-2-methylthioethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylsulphinylethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-mesylethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'4(S)-1-carboxy-2-methoxyethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-methylthiopropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-methylsulphonylpropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-mesylpropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxypropyl)carbamoyl]-4-hydroxybenzyl}carbamoylmethoxy)-2,3,4,5-tetrahydro-1,5-benzothiazepine; or 1,1-dioxo-3,3-dibutyl-5-phenyl-7-methylthio-8-(N-{(R)-α-[N'-((S)-1-carboxyethyl) carbamoyl] benzyl}carbamoylmethoxy)-2,3,4,5-tetrahydro-1,5-benzothiazepine.

or a pharmaceutically acceptable salt, solvate, solvate of such a salt or a prodrug thereof.

Further suitable IBAT inhibitors for use in combination with compounds of the present invention are those disclosed in WO 04/076430.

In a particular aspect of the invention an IBAT inhibitor or a pharmaceutically acceptable salt, solvate, solvate of such a salt or a prodrug thereof is an IBAT inhibitor or a pharmaceutically acceptable salt thereof.

Therefore in an additional feature of the invention, there is provided a combination of a compound of formula (I), or a pharmaceutically acceptable salt, solvate, solvate of such a salt or a prodrug thereof and an IBAT inhibitor, or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an IBAT inhibitor, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and an IBAT inhibitor, or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and an IBAT inhibitor, or a pharmaceutically acceptable salt, solvate, solvate of such a salt or a prodrug thereof.

According to a further aspect of the present invention there is provided a kit comprising:
a) a compound of formula (I), or a pharmaceutically acceptable salt, solvate, solvate of such a salt or a prodrug thereof, in a first unit dosage form;
b) an IBAT inhibitor, or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) an IBAT inhibitor, or a pharmaceutically acceptable salt, solvate, solvate of such a salt or a prodrug thereof, in a second unit dosage form; and
c) container means for containing said first and second dosage forms.

According to another feature of the invention there is provided the use of a compound of the formula (I), or a pharmaceutically acceptable salt, solvate, solvate of such a salt or a prodrug thereof, and an IBAT inhibitor, or a pharmaceutically acceptable salt, solvate, solvate of such a salt or a prodrug thereof, in the manufacture of a medicament for use in the production of a cholesterol lowering effect in a warm-blooded animal, such as man.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an IBAT inhibitor, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an IBAT inhibitor, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

In another aspect of the invention, the compound of formula (I), or a pharmaceutically acceptable salt, solvate, solvate of such a salt or a prodrug thereof, may be administered in association with a PPAR alpha and/or gamma and/or delta agonist, or pharmaceutically acceptable salts, solvates, solvates of such salts or prodrugs thereof. Suitable PPAR alpha and/or gamma and/or delta agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871, WO 98/57941, WO 01/40170, WO 01/40172, WO 02/085844, WO 02/096863, WO03/051821, WO03/051822, WO03/051826, WO 04/000790, WO04/000295, WO04/000294, PCT/GB03/

02584, PCT/GB03/02591, PCT/GB03/02598, J Med Chem, 1996, 39, 665, Expert Opinion on Therapeutic Patents, 10 (5), 623-634 (in particular the compounds described in the patent applications listed on page 634) and J Med Chem, 2000, 43, 527 which are all incorporated herein by reference. Particularly a PPAR alpha and/or gamma and/or delta agonist refers to muraglitazar (BMS 298585), rivoglitazone (CS-011), netoglitazone (MCC-555), balaglitazone (DRF-2593, N,N-2344), clofibrate, fenofibrate, bezafibrate, gemfibrozil, ciprofibrate, beclofibrate, etofibrate, gemcabene, pioglitazone, rosiglitazone, edaglitazone, LY-293111, MBX-2044, AVE-0847, AVE-8134, CLX-0921, DRF-10945, DRF-4832, LY-518674, naveglitazar (LY-818), LY-929, 641597, GW-590735, GW-677954, GW-501516, metaglidazen (MBX-102), T-131, SDX-101 E-3030, PLX-204, ONO-5129, KRP-101, R-483 (BM131258), TAK-559, K-111 (BM170744), netoglitazone (MCC-555; RWJ-241947; isaglitazone), FK-614 or TAK-654

Particularly a PPAR alpha and/or gamma and/or delta agonist refers to (S)-2-ethoxy-3-[4-(2-{4-methanesulphonyloxyphenyl}ethoxy)phenyl]propanoic acid (tesaglitazar) and pharmaceutically acceptable salts thereof.

Therefore in an additional feature of the invention, there is provided a combination of a compound of formula (I), or a pharmaceutically acceptable salt, solvate, solvate of such a salt or a prodrug thereof and a PPAR alpha and/or gamma agonist, or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a PPAR alpha and/or gamma and/or delta agonist, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a PPAR alpha and/or gamma and/or delta agonist, or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and a PPAR alpha and/or gamma and/or delta agonist, or a pharmaceutically acceptable salt, solvate, solvate of such a salt or a prodrug thereof.

According to a further aspect of the present invention there is provided a kit comprising:
a) a compound of formula (I), or a pharmaceutically acceptable salt, solvate, solvate of such a salt or a prodrug thereof, in a first unit dosage form;
b) a PPAR alpha and/or gamma and/or delta agonist, or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) a PPAR alpha and/or gamma and/or delta agonist, or a pharmaceutically acceptable salt, solvate, solvate of such a salt or a prodrug thereof, in a second unit dosage form; and
c) container means for containing said first and second dosage forms.

According to another feature of the invention there is provided the use of a compound of the formula (I), or a pharmaceutically acceptable salt, solvate, solvate of such a salt or a prodrug thereof, and a PPAR alpha and/or gamma and/or delta agonist, or a pharmaceutically acceptable salt, solvate, solvate of such a salt or a prodrug thereof, in the manufacture of a medicament for use in producing a cholesterol lowering effect in a warm-blooded animal, such as man.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of a PPAR alpha and/or gamma and/or delta agonist, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

In another aspect of the invention, there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an-agonists to the receptor H74A (nicotinic acid receptor). HM74A receptor agonists may be nicotine acid derivates. As used herein "nicotinic acid derivative" means a compounds comprising a pyridine-3-carboxylate structure or a pyrazine-2-carboxylate structure. Examples of nicotinic acid derivatives include nicotinic acid, niceritrol, nicofuranose, NIASPAN® and acipimox.

HM74A receptor agonists may be anthranilic acid derivatives described in WO-2005016867 and WO-2005016870.

Other nicotinic receptor agonists are for example compounds described in WO2005011677, WO2004032928 and WO2004033431.

Therefore, in an additional feature of the invention, there is provided a combination of a compound of formula (I), or a pharmaceutically acceptable salt, solvate, solvate of such a salt or a prodrug thereof and a HM74A receptor agonists or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a HM74A receptor agonists, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a HM74A receptor agonists, or a pharmaceutically acceptable salt, solvate, solvate of such a salt or a prodrug thereof, in association with a pharmaceutically acceptable diluent or carrier.

In another aspect of the invention, there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration Of a mediator of reverse cholesterol transport i.e. a peptide (Apo A-1 mimetic peptides) or small molecule mediator of reverse cholesterol transport e.g. those described in Circ. 2002; 105:290, Circ. 2004.109:3215, Curr. Opinion in Lipidology 2004, 15:645 or in WO2004094471.

In another aspect of the invention, the compound of formula I, or a pharmaceutically acceptable salt or solvate thereof, or a solvate of such a salt, may be administered in association with an anti-obesity compound, or pharmaceutically acceptable salts, solvates, solvates of such salts or prodrugs thereof, for example a pancreatic lipase inhibitor e.g. orlistat (EP 129,748) or an appetite (satiety) controlling substance for example sibutramine (GB 2,184,122 and U.S. Pat. No. 4,929,629), a cannabinoid 1 (CB1) antagonist or inverse agonist, or pharmaceutically acceptable salts, solvates, solvates of such salts or prodrugs thereof, for example rimonabant (EP 656354) and as described in WO01/70700 or a melanin concentrating hormone (MCH) antagonist, or pharmaceutically acceptable salts, solvates, solvates of such salts or prodrugs thereof, for example as described in WO 04/004726.

According to another feature of the invention there is provided the use of a compound of the formula (I), or a pharmaceutically acceptable salt, solvate, solvate of such a salt or a prodrug thereof, and a nicotinic acid derivative, or a pharmaceutically acceptable salt, solvate, solvate of such a salt or a prodrug thereof, in the manufacture of a medicament for use in the production of a cholesterol lowering effect in a warm-blooded animal, such as man.

In another aspect of the invention, the compound of formula (I), or a pharmaceutically acceptable salt, solvate, solvate of such a salt or a prodrug thereof, may be administered in association with a bile acid sequestrant or a pharmaceutically acceptable salt, solvate, solvate of such a salt or a prodrug thereof. Suitable bile acid sequestrants include cholestyramine, cholestipol and cosevelam hydrochloride.

Therefore, in an additional feature of the invention, there is provided a combination of a compound of formula (I), or a pharmaceutically acceptable salt, solvate, solvate of such a salt or a prodrug thereof and a bile acid sequestrant or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a bile acid sequestrant, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a bile acid sequestrant, or a pharmaceutically acceptable salt, solvate, solvate of such a salt or a prodrug thereof, in association with a pharmaceutically acceptable diluent or carrier.

According to another feature of the invention there is provided the use of a compound of the formula (I), or a pharmaceutically acceptable salt, solvate, solvate of such a salt or a prodrug thereof, and a bile acid sequestrant, or a pharmaceutically acceptable salt, solvate, solvate of such a salt or a prodrug thereof, in the manufacture of a medicament for use in the production of a cholesterol lowering effect in a warm-blooded animal, such as man.

In another aspect of the invention, the compound of formula I, or a pharmaceutically acceptable salt or solvate thereof, or a solvate of such a salt, may be administered in association with a cholesteryl ester transfer protein (CETP) inhibitor, or pharmaceutically acceptable salts, solvates, solvates of such salts or prodrugs thereof, for example JTT-705, torcetrapib (CP-529414), Bay 194789 and those referenced and described in WO05033082 or WO 00/38725 page 7 line 22-page 10, line 17 which are incorporated herein by reference.

In another aspect of the invention, the compound of formula I, or a pharmaceutically acceptable salt or solvate thereof, or a solvate of such a salt, may be administered in association with a acyl coenzymA: cholesterol O-acyltransferase (ACAT) inhibitor, or pharmaceutically acceptable salts, solvates, solvates of such salts or prodrugs thereof, for example pactimibe (CS-505), eflucimibe (F-12511) and SMP-797, avasimibe or K604.

In yet another aspect of the invention, the compound of formula I, association with modulators for example GW-4064 and INT-747 of nuclear receptors such as farnesoid or a pharmaceutically acceptable salt or solvate thereof, or a solvate of such a salt, may be administered in X receptor (FXR), or pharmaceutically acceptable salt, solvate, solvate of such a salt or a prodrug thereof In another aspect of the invention, the compound of formula I, or a pharmaceutically acceptable salt or solvate thereof, or a solvate of such a salt, may be administered in association with a phytosterol compound, or pharmaceutically acceptable salts, solvates, solvates of such salts or prodrugs thereof, for example stanols. An example of phytosterol analogs is FM-VP4.

In another aspect of the invention, the compound of formula I, or a pharmaceutically acceptable salt or solvate thereof, or a solvate of such a salt, may be administered in association with other therapies for the treatment of metabolic syndrome or type 2 diabetes and its associated complications, these include biguanide drugs, for example metformin, phenformin and buformin, insulin (synthetic insulin analogues, amylin) and oral antihyperglycemics (these are divided into prandial glucose regulators and alpha-glucosidase inhibitors). An example of an alpha-glucosidase inhibitor is acarbose or voglibose or miglitol. An example of a prandial glucose regulator is repaglinide or nateglinide.

In another aspect of the invention, the compound of formula I, or a pharmaceutically acceptable salt or solvate thereof, or a solvate of such a salt, may be administered in association with a sulfonylurea for example: glimepiride, glibenclamide (glyburide), gliclazide, glipizide, gliquidone, chloropropamide, tolbutamide, acetohexamide, glycopyramide, carbutamide, glibonuride, glisoxepid, glybuthiazole, glibuzole, glyhexamide, glymidine, glypinamide, phenbutamide, tolcylamide and tolazamide. Preferably the sulfonylurea is glimepiride or glibenclamide (glyburide). More preferably the sulfonylurea is glimepiride. Therefore the present invention includes administration of a compound of the present invention in conjunction with one, two or more existing therapies described in this paragraph. The doses of the other existing therapies for the treatment of type 2 diabetes and its associated complications will be those known in the art and approved for use by regulatory bodies for example the FDA and may be found in the Orange Book published by the FDA. Alternatively smaller doses may be used as a result of the benefits derived from the combination.

According to an additional further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration one or more of the following agents selected from Group X:

an antihypertensive compound (for example althiazide, benzthiazide, captopril, carvedilol, chlorothiazide sodium, clonidine hydrochloride, cyclothiazide, delapril hydrochloride, dilevalol hydrochloride, doxazosin mesylate, fosinopril sodium, guanfacine hydrochloride, methyldopa, metoprolol succinate, moexipril hydrochloride, monatepil maleate, pelanserin hydrochloride, phenoxybenzamine hydrochloride, prazosin hydrochloride, primidolol, quinapril hydrochloride, quinaprilat, ramipril, terazosin hydrochloride, candesartan, candesartan cilexetil, telmisartan, amlodipine besylate, amlodipine maleate and bevantolol hydrochloride);

an angiotensin converting enzyme inhibitor (for example alacepril, alatriopril, altiopril calcium, ancovenin, benazepril, benazepril hydrochloride, benazeprilat, benzoylcaptopril, captopril, captopril-cysteine, captopril-glutathione, ceranapril, ceranopril, ceronapril, cilazapril, cilazaprilat, delapril, delapril-diacid, enalapril, enalaprilat, enapril, epicaptopril, foroxymithine, fosfenopril, fosenopril, fosenopril sodium, fosinopril, fosinopril sodium, fosinoprilat, fosinoprilic acid, glycopril, hemorphin-4, idrapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spiraprilat, spirapril hydrochloride, spiraprilat, spiropril, spiropril hydrochloride, temocapril, temocapril hydrochloride, teprotide, trandolapril, trandolaprilat, utibapril, zabicipril, zabiciprilat, zofenopril and zofenoprilat);

an angiotensin II receptor antagonist (for example candesartan, candesartan cilexetil, losartan, valsartan, irbesartan, tasosartan, tehnisartan and eprosartan);

an andrenergic blocker (for example bretylium tosylate, dihydroergotamine so mesylate, phentolamine mesylate, solypertine tartrate, zolertine hydrochloride, carvedilol or labetalol hydrochloride); an alpha andrenergic blocker (for example fenspiride hydrochloride, labetalol hydrochloride, proroxan and alfuzosin hydrochloride); a beta andrenergic blocker (for example acebutolol, acebutolol hydrochloride, alprenolol hydrochloride, atenolol, bunolol hydrochloride, carteolol hydrochloride, celiprolol hydrochloride, cetamolol hydrochloride, cicloprolol hydrochloride, dexpropranolol hydrochloride, diacetolol hydrochloride, dilevalol hydrochloride, esmolol hydrochloride, exaprolol hydrochloride, flestolol sulfate, labetalol hydrochloride, levobetaxolol hydrochloride, levobunolol hydrochloride, metalol hydrochloride, metoprolol, metoprolol tartrate, nadolol, pamatolol sulfate, penbutolol sulfate, practolol, propranolol hydrochloride, sotalol hydrochloride, timolol, timolol maleate, tiprenolol hydrochloride, tolamolol, bisoprolol, bisoprolol fumarate and nebivolol); or a mixed alpha/beta andrenergic blocker;

an andrenergic stimulant (for example combination product of chlorothiazide and methyldopa, the combination product of methyldopa hydrochlorothiazide and methyldopa, clonidine hydrochloride, clonidine, the combination product of chlorthalidone and clonidine hydrochloride and guanfacine hydrochloride);

channel blocker, for example a calcium channel blocker (for example clentiazem maleate, amlodipine besylate, isradipine, nimodipine, felodipine, nilvadipine, nifedipine, teludipine hydrochloride, diltiazem hydrochloride, belfosdil, verapamil hydrochloride or fostedil);

a diuretic (for example the combination product of hydrochlorothiazide and spironolactone and the combination product of hydrochlorothiazide and triamterene);

anti-anginal agents (for example amlodipine besylate, amlodipine maleate, betaxolol hydrochloride, bevantolol hydrochloride, butoprozine hydrochloride, carvedilol, cinepazet maleate, metoprolol succinate, molsidomine, monatepil maleate, primidolol, ranolazine hydrochloride, tosifen or verapamil hydrochloride);

vasodilators for example coronary vasodilators (for example fostedil, azaclorzine hydrochloride, chromonar hydrochloride, clonitrate, diltiazem hydrochloride, dipyridamole, droprenilamine, erythrityl tetranitrate, isosorbide dinitrate, isosorbide mononitrate, lidoflazine, mioflazine hydrochloride, mixidine, molsidomine, nicorandil, nifedipine, nisoldipine, nitroglycerine, oxprenolol hydrochloride, pentrinitrol, perhexyline maleate, prenylamine, propatyl nitrate, terodiline hydrochloride, tolamolol and verapamil);

anti-coagulants (selected from argatroban, bivalirudin, dalteparin sodium, desirudin, dicumarol, lyapolate sodium, nafamostat mesylate, phenprocoumon, tinzaparin sodium and warfarin sodium);

antithrombotic agents (for example anagrelide hydrochloride, bivalirudin, cilostazol, dalteparin sodium, danaparoid sodium, dazoxiben hydrochloride, efegatran sulfate, enoxaparin sodium, fluretofen, ifetrofan, ifetroban sodium, lamifiban, lotrafiban hydrochloride, napsagatran, orbofiban acetate, roxifiban acetate, sibrafiban, tinzaparin sodium, trifenagrel, abciximab and zolimomab aritox);

fibrinogen receptor antagonists (for example roxifiban acetate, fradafiban, orbofiban, lotrafiban hydrochloride, tirofiban, xemilofiban, monoclonal antibody 7E3 and sibrafiban)

platelet inhibitors (for example cilostezol, clopidogrel bisulfate, epoprostenol, epoprostenol sodium, ticlopidine hydrochloride, aspirin, ibuprofen, naproxen, sulindae, indomethacin, mefenamate, droxicam, diclofenac, sulfinpyrazone and piroxicam, dipyridamole);

platelet aggregation inhibitors (for example acadesine, beraprost, beraprost sodium, ciprostene calcium, itezigrel, lifarizine, lotrafiban hydrochloride, orbofiban acetate, oxagrelate, fradafiban, orbofiban, tirofiban and xemilofiban)

hemorrheologic agents (for example pentoxifylline);

lipoprotein associated coagulation inhibitors;

Factor VIIa inhibitors;

Factor Xa inhibitors;

low molecular weight heparins (for example enoxaparin, nardroparin, dalteparin, certroparin, parnaparin, reviparin and tinzaparin);

liver X receptor (LXR) agonists for example GW-3965 and those described in WO00224632, WO00103705, WO02090375 and WO00054759 (claim 1 and the named examples of these four application are incorporated herein by reference);

microsomal triglyceride transfer protein inhibitors for example implitapide, CP-346086, JTT-130, BMS-201038, R-103757 and those described in WO05/021486, WO03004020, WO03002533, WO02083658 and WO 00242291 (claim 1 and the named examples of these four application are incorporated herein by reference);

ApoA1 expression inducer for example those described in WO2005032559 or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Therefore, in an additional feature of the invention, there is provided a combination of a compound of formula (I), or a pharmaceutically acceptable salt, solvate, solvate of such a salt or a prodrug thereof and a compound from Group X or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a compound from Group X, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a compound from Group X, or a pharmaceutically acceptable salt, solvate, solvate of such a salt or a prodrug thereof, in association with a pharmaceutically acceptable diluent or carrier.

According to another feature of the invention there is provided the use of a compound of the formula (I), or a pharmaceutically acceptable salt, solvate, solvate of such a salt or a prodrug thereof, and a compound from Group X, or a pharmaceutically acceptable salt, solvate, solvate of such a salt or a prodrug thereof, in the manufacture of a medicament for use in the production of a cholesterol lowering effect in a warm-blooded animal, such as man.

In addition to their use in therapeutic medicine, the compounds of formula (I), or a pharmaceutically acceptable salt, solvate, solvate of such a salt or a prodrug thereof, are also useful as pharmacological tools in the development and standardisation of in vitro and in vivo test systems for the evaluation of the effects of inhibitors of cholesterol absorption in laboratory animals such as cats, dogs, rabbits, monkeys, rats and mice, as part of the search for new therapeutic agents.

What has been described above regarding the combination therapy with a compound of formula (I), and the use of a compound of formula (I) for the treatment or prophylaxis of various diseases and conditions also apply for compound (I2).

Many of the intermediates described herein are novel and are thus provided as a further feature of the invention. For example compounds of formula (XVI) show cholesterol absorption inhibitory activity when tested in the above referenced in vitro test assay and are thus claimed as a further feature of the invention.

Thus in a further feature of the invention, there is provided a compound of formula (XVI), or a pharmaceutically acceptable salt, solvate, solvate of such a salt or a prodrug thereof.

Therefore according to a further aspect of the invention there is provided a pharmaceutical composition which comprises a compound of formula (XVI), or a pharmaceutically acceptable salt, solvate, solvate of such a salt or a prodrug thereof in association with a pharmaceutically-acceptable diluent or carrier.

According to an additional aspect of the present invention there is provided a compound of the formula (XVI), or a pharmaceutically acceptable salt, solvate, solvate of such a salt or a prodrug thereof, for use in a method of prophylactic or therapeutic treatment of a warm-blooded animal, such as man.

Thus according to this aspect of the invention there is provided a compound of the formula (VI), or a pharmaceutically acceptable salt, solvate, solvate of such a salt or a prodrug thereof, for use as a medicament.

According to another feature of the invention there is provided the use of a compound of the formula (XVI), or a pharmaceutically acceptable salt, solvate, solvate of such a salt or a prodrug thereof, in the manufacture of a medicament for use in the production of a cholesterol absorption inhibitory effect in a warm-blooded animal, such as man.

According to another feature of the invention there is provided the use of a compound of the formula (XVI) or a pharmaceutically acceptable salt, solvate, solvate of such a salt or a prodrug thereof, in the manufacture of a medicament for use in the treatment of hyperlipidaemic conditions in a warm-blooded animal, such as man.

According to a further feature of this aspect of the invention there is provided a method for producing a cholesterol absorption inhibitory effect in a warm-blooded animal, such as man, in need of such treatment which comprises administering to said animal an effective amount of a compound of formula (XVI), or a pharmaceutically acceptable salt, solvate, solvate of such a salt or a prodrug thereof.

According to a further feature of this aspect of the invention there is provided a method of treating hyperlipidemic conditions in a warm-blooded animal, such as man, in need of such treatment which comprises administering to said animal an effective amount of a compound of formula (XVI), or a pharmaceutically acceptable salt, solvate, solvate of such a salt or a prodrug thereof.

In the above other pharmaceutical composition, process, method, use and medicament manufacture features, the alternative and preferred embodiments of the compounds of the invention described herein also apply.

EXAMPLES

The invention will now be illustrated in the following non limiting Examples, in which standard techniques known to the skilled chemist and techniques analogous to those described in these Examples may be used where appropriate, and in which, unless otherwise stated:

(i) evaporations were carried out by rotary evaporation in vacuo and work up procedures were carried out after removal of residual solids such as drying agents by filtration;

(ii) all reactions were carried out under an inert atmosphere at ambient temperature, typically in the range 18-25° C., with solvents of HPLC grade under anhydrous conditions, unless otherwise stated;
(iii) column chromatography (by the flash procedure) was performed on Silica gel 40-63 µm (Merck);
(iv) yields are given for illustration only and are not necessarily the maximum attainable;
(v) the structures of the end products of the formula (I) were generally confirmed by nuclear (generally proton) magnetic resonance (NMR) and mass spectral techniques; magnetic resonance chemical shift values were measured in deuterated $CDCl_3$ (unless otherwise stated) on the delta scale (ppm downfield from tetramethylsilane); proton data is quoted unless otherwise stated; spectra were recorded on a Varian Mercury-300 MHz, Varian Unity plus-400 MHz, Varian Unity plus-600 MHz or on Varian Inova-500 MHz spectrometer unless otherwise stated data was recorded at 400 MHz; and peak multiplicities are shown as follows: s, singlet; d, doublet; dd, double doublet; t, triplet; tt, triple triplet; q, quartet; tq, triple quartet; m, multiplet; br, broad; ABq, AB quartet; ABd, AB doublet, ABdd, AB doublet of doublets; dABq, doublet of AB quartets;
Mass spectra were recorded on one of the following instruments: LCT, QTOF, ZQ Mass spectrometer, all from Waters.
LC-MS:
Separation was performed using Agilent 1100 Series Modules or Waters 1525 pump on a Synergi MAX-RP (Phenomenex) C12 3×50 mm 4 µm with gradient elution.
Samples were injected using Waters 2700 Sample Manager.
Mobile Phases:
Generic gradients were applied from 5% to 95% acetonitrile. Buffers containing 10 mM ammonium acetate or 5 mM ammonium formiate/5 mM formic acid were used.
The mass spectra were recorded with a Waters ZQ2000 or Waters MAD equipped with an electrospray interface, swithing positive and negative ionization mode. UV spectra were collected by a Aglent 1100 PDA or Waters 2996 DAD and the evaporative light scattering (ELS) signal by a Sedere Sedex 55 or 75.
Data collection and evaluation were performed using the MassLynx software.
Accurate mass data were determined using either a LCT or QTOF MS (Waters) with leucine enkephaline (m/z 556.2771) as lockmass. Unless otherwise stated the mass ion quoted is $(MH^+)$
Unless further details are specified in the text, analytical high performance liquid chromatography (HPLC) was performed on Prep LC 2000 (Waters), Cromasil $C_8$, 7 µm, (Akzo Nobel); MeCN and de-ionised water 10 mM ammonium acetate as mobile phases, with suitable composition;
(vii) intermediates were not generally fully characterised and purity was assessed by thin layer chromatography (TLC), HPLC, infra-red (IR), MS or NMR analysis;
(viii) where solutions were dried sodium sulphate was the drying agent; and
(ix) the following abbreviations may be used hereinbefore or hereinafter:—

| DCM | dichloromethane; |
|---|---|
| DMF | N,N-dimethylformamide; |
| TBTU | o-Benzotriazol-1-yl-N,N,N',N'-tetramethyluronium tetrafluoroborate; |
| EtOAc | ethyl acetate; |
| MeCN | acetonitrile; |
| TFA | trifluoroacetic acid; |
| DMAP | 4-(dimethylamino)pyridine; |
| BSA | N,O-Bis(trimethylsilyl)acetamide; and |
| TBAF | tetrabutylammonium fluoride; |
| NMM | N-methyl morpholine; |
| TEA | triethylamine; |
| DBN | 1,5-diazabicyclo-[4,3,0]-non-5-ene. |

EXAMPLES

It will be appreciated by those skilled in the art that the examples may be modified within the realms of the invention, why the invention is not limited to particular embodiments.

Example 1

N-({4-[(2R,3R)-3-{[2-(2,3-dihydro-1,4-benzodioxin-6-yl)-2-hydroxyethyl]thio}-1-(4-fluorophenyl)-4-oxoazetidin-2-yl]phenoxy}acetyl)glycyl-3-methyl-D-valine To a solution of N-[(4-{(2R,3R)-1-(4-fluorophenyl)-3-[(3-nitropyridin-2-yl)dithio]-4-oxoazetidin-2-yl}phenoxy)acetyl]glycyl-3-methyl-D-valine (0.030 g, 0.045 mmol) in acetone/water (2/0.5 ml) was added triphenylphosphine (0.012 g, 0.045 mmol). After 30 minutes the solvent was evaporated and to the residue was added dichloromethane (2 ml) and triethylamine (0.018 g, 0.179 mmol) followed by the addition of 2-bromo-1-(2,3-dihydro-1,4-benzodioxin-6-yl)ethanone (0.029 g, 0.112 mmol). After 10 minutes the reaction was quenched by the addition of water (1 ml) followed by concentration of the mixture. MeOH (2 ml) was added followed by the addition of sodium borohydride (0.017 g, 0.447 mmol). Full conversion to the corresponding alcohol was achieved within 5 minutes. The reaction was quenched by the addition of 0.1M $NH_4OAc$ buffer (1 ml). Preparative HPLC of the mixture using an eluent of 20-45% $CH_3CN$ in 0.1M $NH_4OAc$ buffer followed by freeze drying of pure fractions afforded the desired compound. m/z: 694.7 (M−1). $^1H$ NMR [$(CD_3)_2SO$, 400 MHz] δ 0.89 (s, 9H), 2.78-2.89 (m, 2H), 3.82 (d, 2H), 4.05-4.28 (m, 6H), 4.51 (s, 2H), 4.55-4.61 (m, 1H), 5.01-5.03 (m, 1H), 6.72-7.37 (m, 11H), 7.81-7.87 (m, 1H), 8.25 (t, 1H).

Example 2

N-({4-[(2R,3R)-3-{[2-(1,3-Benzodioxol-5-yl)-2-hydroxyethyl]thio}-1-(4-fluorophenyl)-4-oxoazetidin-2-yl]phenoxy}acetyl)glycyl-3-cyclohexyl-D-alanine To a solution of {4-[(2R,3R)-3-{[2-(1,3-benzodioxol-5-yl)-2-oxoethyl]thio}-1-(4-fluorophenyl)-4-oxoazetidin-2-yl]phenoxy}acetic acid (Method 7) (0.025 g, 0.049 mmol) and NMM (0.020 ml, 0.178 mmol) in DMF (3 ml) at RT was added TBTU (0.020 g, 0.062 mmol). The reaction mixture was stirred for 90 min after which glycyl-3-cyclohexyl-D-alanine (Method 9) (0.012 g, 0.035 mmol) was added. The mixture was stirred for 20 h before the reaction was quenched by the addition of water (1 ml). The mixture was diluted with methanol (2 ml) and then NaBH4 (0.028 g, 0.740 mmol) was added. After 15 min the reaction was quenched by the addition of an aqueous solution of hydrochloric acid (1M, 1 ml) and most of the methanol was removed under reduced pressure. The remaining solution was purified by preparative HPLC using a gradient of 20-60% MeCN in a 0.1M ammonium acetate buffer as eluent. Freeze-drying of the pure fractions gave the desired product as.

M/z (ES−): 721.1. $^1$H NMR (DMSO, 400 MHz): δ 0.69-1.69 (m, 13H), 2.77-2.91 (m, 2H), 3.71-3.78 (m, 2H), 4.10-4.19 (m, 1H), 4.21-4.27 (m, 1H), 4.49 (s, 2H), 4.55-4.65 (m, 1H), 4.99-5.04 (m, 1H), 5.88-5.96 (m, 2H), 6.69-6.85 (m, 3H), 6.92-6.99 (m, 2H), 7.07-7.24 (m, 4H), 7.31-7.38 (m, 2H), 7.93-8.02 (m, 1H), 8.17-8.25 (m, 1H).

Example 3

N-({4-[(2R,3R)-3-{[2-(1,3-Benzodioxol-5-yl)-2-hydroxyethyl]thio}-1-(4-fluorophenyl)-4-oxoazetidin-2-yl]phenoxy}acetyl)glycyl-3-methyl-D-valine To a solution of {4-[(2R,3R)-3-{[2-(1,3-benzodioxol-5-yl)-2-hydroxyethyl]thio}-1-(4-fluorophenyl)-4-oxoazetidin-2-yl]phenoxy}acetic acid (0.006 g, 0.012 mmol) and NMM (0.007 ml, 0.064 mmol) in DMF (3 ml) at RT was added TBTU (0.005 g, 0.016 mmol). The reaction mixture was stirred for 60 min after which glycyl-3-methyl-D-valine (Method 10) (0.003 g, 0.016 mmol) was added. The mixture was stirred for 4 h before the solution was purified by preparative HPLC using a gradient of 20-60% MeCN in a 0.1M ammonium acetate buffer as eluent. Freeze-drying of the pure fractions gave the desired product.
M/z (ES−): 681.1. $^1$H NMR (DMSO, 400 MHz): δ 0.86 (s, 9H), 2.75-2.94 (m, 2H), 3.74-3.82 (m, 2H), 3.92-4.01 (m, 1H), 4.21-4.32 (m, 1H), 4.49 (s, 2H), 4.56-4.65 (m, 1H), 4.98-5.04 (m, 1H), 5.90-5.95 (m, 2H), 6.70-6.84 (m, 3H), 6.92-6.99 (m, 2H), 7.08-7.24 (m, 4H), 7.31-7.38 (m, 2H), 7.63-7.78 (m, 1H), 8.23-8.29 (m, 1H).

Example 4

N-({4-[(2R,3R)-3-{[2-(1,3-benzodioxol-5-yl)-2-hydroxyethyl]thio}-1-(4-fluorophenyl)-4-oxoazetidin-2-yl]phenoxy}acetyl)glycyl-b,b-dimethyl-D-phenylalanine To a stirred solution of N-({4-[(2R,3R)-3-{[2-(1,3-benzodioxol-5-yl)-2-hydroxyethyl]thio}-1-(4-fluorophenyl)-4-oxoazetidin-2-yl]phenoxy}acetyl)glycine (15.6 mg, 0.027 mmol) in DMF (2 ml) was added N-methylmorpholine (15 µl, 0.091 mmol). TBTU (12.2 mg, 0.038 mmol) was added and the reaction mixture was stirred at 30° C. for 1 hour. β,β-dimethyl-D-phenylalanine trifluoroacetate (10.2 mg, 0.033 mmol) was added and the mixture was stirred at ambient temperature overnight. The solution was purified with preparative HPLC on a C8 column, UV 240/260 nm. A gradient from 20 to 45% MeCN in 0.1M NH$_4$OAc buffer was used as eluent. The pure fractions were collected and the MeCN was removed under reduced pressure. The remaining water solution was acidified to pH 1 with HCl (1M) and extracted with DCM. The organic phase was passed through a phase separator and concentrated under reduced pressure. The residue was dissolved in MeCN and water. After lyophilisation, the title compound was obtained. H-NMR (400 MHz, DMSO-d$_6$): 1.28 (d, 6H), 2.74-2.92 (m, 2H), 3.58-3.82 (m, 2H) 4.30-4.21 (m, 1H), 4.46 (s, 2H), 4.53-4.65 (m, 2H) 5.00 (b, 0.5H), 5.03 (b, 0.5H), 5.53 (b, 1H), 5.90-5.94 (m, 2H), 6.70-6.79 (m, 2H), 6.82 (s, 1H), 6.90-6.98 (m, 2H), 7.07-7.15 (m, 3H), 7.18-7.26 (m, 4H), 7.27-7.37 (m, 4H), 7.78 (b, 1H), 8.19 (t, 1H). M/z: 742.68 (M−1).

Example 5

N-({4-[(2R,3R)-3-{[2-(1,3-benzodioxol-5-yl)-2-hydroxyethyl]thio}-1-(4-fluorophenyl)-4-oxoazetidin-2-yl]phenoxy}acetyl)glycyl-D-valine To a stirred solution of N-({4-[(2R,3R)-3-{[2-(1,3-benzodioxol-5-yl)-2-hydroxyethyl]thio}-1-(4-fluorophenyl)-4-oxoazetidin-2-yl]phenoxy}acetyl)glycine (12.8 mg, 0.023 mmol) in DMF (2 ml) was added N-methylmorpholine (15 µl, 0.091 mmol). TBTU (8.8 mg, 0.027 mmol) was added and the reaction mixture was stirred at 30° C. for 1 hour. D-valine (4.5 mg, 0.038 mmol) was added and the mixture was stirred at ambient temperature overnight. The solution was purified with preparative HPLC on a C8 column, UV 240/260 nm. A gradient from 20 to 45% MeCN in 0.1M NH$_4$OAc buffer was used as eluent. The pure fractions were collected and the MeCN was removed under reduced pressure. The remaining water solution was acidified to pH 1 with HCl (1M) and extracted with DCM. The organic phase was passed through a phase separator and concentrated under reduced pressure. The residue was dissolved in MeCN and water. After lyophilisation, the title compound was obtained. H-NMR (400 MHz, DMSO-d$_6$): 0.80 (bs, 6H), 1.92-2.04 (m, 1H), 2.77-2.90 (m, 2H), 3.77 (bs, 2H), 3.94-4.10 (b, 1H), 4.22-4.30 (m, 1H), 4.49 (s, 2H), 4.56-4.64 (m, 1H), 4.99-5.03 (m, 1H), 5.90-5.94 (m, 2H), 6.70-6.79 (m, 2H), 6.82 (s, 1H), 6.96 (d, 2H), 7.09-7.15 (m, 2H), 7.18-7.24 (m, 2H), 7.34 (d, 2H), 8.23 (bs, 1H). M/z: 666.67 (M−1).

Example 6

N-({4-[(2R,3R)-3-{[2-(1,3-benzodioxol-5-yl)-2-hydroxyethyl]thio}-1-(4-chlorophenyl)-4-oxoazetidin-2-yl]phenoxy}acetyl)glycyl-3-cyclohexyl-D-alanine To a stirred solution of {4-[(2R,3R)-3-{[2-(1,3-benzodioxol-5-yl)-2-oxoethyl]thio}-1-(4-chlorophenyl)-4-oxoazetidin-2-yl]phenoxy}acetic acid (35.4 mg, 0.067 mmol)) in DMF (3 ml) was added N-methylmorpholine (35 µl, 0.23 mmol). TBTU (29.3 mg, 0.091 mmol) was added and the reaction mixture was stirred at 30° C. for 1 hour. Glycyl-3-cyclohexyl-D-alanine (18.4 mg, 0.081 mmol) was added and the mixture was stirred at ambient temperature for 60 hours. The formation of the ketone of the title compound was confirmed. M/z: 736.67 (M+1) and 734.71 (M−1). Without further purification, methanol (2 ml) and sodium borohydride (28.0 mg, 0.740 mmol) was added and the mixture was stirred for 20 minutes. Ammonium acetate (38.4 mg) was added and the solution was purified with preparative HPLC on a C8 column, UV 240/260 nm. A gradient from 20 to 45 MeCN in 0.1M NH$_4$OAc buffer was used as eluent. The pure fractions were collected and the MeCN was removed under reduced pressure. The remaining water solution was acidified to pH 1 with HCl (1M) and extracted with DCM. The organic phase was passed through a phase separator and concentrated under reduced pressure. The residue was dissolved in MeCN and water. After lyophilisation, the title compound was obtained $^1$H-NMR (400 MHz, DMSO-d$_6$): 0.70-1.68 (m, 13H), 2.78-2.88 (m, 2H), 3.75 (d, 2H), 4.13-4.21 (m, 1H), 4.23-4.28 (m, 1H), 4.49 (s, 2H), 4.56-4.64 (m, 1H), 5.02 (d, 0.5H), 5.04 (d, 0.5H), 5.56 (b, 1H), 6.70-6.79 (m, 2H), 6.82 (s, 1H), 6.96 (d, 2H), 7.18 (d, 2H), 7.30-7.37 (m, 4H), 8.04 (b, 1H), 8.20 (t, 1H). M/z: 736.69 (M−1).

Example 7

N-({4-[(2R,3R)-3-{[2-(1,3-benzodioxol-5-yl)-2-hydroxyethyl]thio}-1-(4-fluorophenyl)-4-oxoazetidin-2-yl]phenoxy}acetyl)glycyl-D-lysine To a stirred solution of N-({4-[(2R,3R)-3-{[2-(1,3-benzodioxol-5-yl)-2-hydroxyethyl]thio}-1-(4-fluorophenyl)-4-oxoazetidin-2-yl]phenoxy}acetyl)glycine (11.3 mg, 0.020 mmol) in DCM (2 ml) were added tert-butyl $N^6$-(tert-butoxycarbonyl)-D-lysinate hydrochloride (9.5 mg, 0.028 mmol), N-methylmorpholine (15 μl, 0.091 mmol) and TBTU (11.0 mg, 0.034 mmol). The reaction mixture was stirred at ambient temperature for 3 hours. The formation of the intermediate tert-butyl N-({4-[(2R,3R)-3-{[2-(1,3-benzodioxol-5-yl)-2-hydroxyethyl]thio}-1-(4-fluorophenyl)-4-oxoazetidin-2-yl]phenoxy}acetyl)glycyl-$N^6$-(tert-butoxycarbonyl)-D-lysinate was confirmed. M/z: 852.23 (M−1). The solvent was removed under reduced pressure and the residue was dissolved in formic acid (2 ml). The mixture was stirred at ambient temperature for 48 hours. The solvent was co-evaporated with toluene and the residue was purified with preparative HPLC on a C8 column, UV 240/260 nm. A gradient from 20 to 45% MeCN in 0.1M $NH_4OAc$ buffer was used as eluent. The MeCN was removed under reduced pressure and the residue was lyophilised to give the title. H-NMR (400 MHz, DMSO-$d_6$): 1.08-1.32 (m, 2H), 1.37-65 (m, 4H), 2.63 (t, 2H), 2.77-2.92 (m, 2H), 3.70 (d, 2H), 3.76-3.82 (m, 1H), 4.25 (d, 0.5H), 4.28 (d, 0.5H), 4.50 (s, 2H), 4.57-4.64 (m, 1H), 5.00 (d, 0.5H), 5.02 (d, 0.5H), 5.90-5.94 (m, 2H), 6.70-6.81 (m, 2H), 6.83 (s, 1H), 6.96 (d, 2H), 7.08-7.16 (m, 2H), 7.17-7.24 (m, 2H), 7.34 (d, 2H), 7.45-7.55 (m, 1H), 8.37-8.43 (m, 1H). M/z: 697.32 (M+1) and 695.39 (M−1).

Example 8

N-({4-[(2R,3R)-3-{[2-(1,3-Benzodioxol-5-yl)-2-hydroxyethyl]thio}-1-(4-methylphenyl)-4-oxoazetidin-2-yl]phenoxy}acetyl)glycyl-3-cyclohexyl-D-alanine To a solution of {4-[(2R,3R)-3-{[2-(1,3-benzodioxol-5-yl)-2-oxoethyl]thio}-1-(4-methylphenyl)-4-oxoazetidin-2-yl]phenoxy}acetic acid (0.020 g, 0.040 mmol) and NMM (0.013 ml, 0.116 mmol) in DMF (3 ml) at RT was added TBTU (0.020 g, 0.062 mmol). The reaction mixture was stirred for 30 min after which glycyl-3-cyclohexyl-D-alanine (0.011 g, 0.032 mmol) was added. The mixture was stirred for 22 h before the reaction was quenched by the addition of water (1 ml). The mixture was diluted with MeOH (2 ml) and added NaBH4 (0.028 g, 0.740 mmol). After 15 min the reaction was quenched by the addition of an aqueous solution of hydrochloric acid (1M, 1 ml) and most of the methanol was removed under reduced pressure. The remaining solution was purified by preparative HPLC using a gradient of 20-60% MeCN in a 0.1M ammonium acetate buffer as eluent. Freeze-drying of the pure fractions gave the desired product.

M/z (ES−): 716.7. $^1$H NMR (DMSO, 400 MHz): δ 0.70-1.70 (m, 13H), 2.16 (s, 3H), 2.77-2.90 (m, 2H), 3.70-3.78 (m, 2H), 4.10-4.22 (m, 2H), 4.48 (s, 2H), 4.55-4.64 (m, 1H), 4.93-5.00 (m, 1H), 5.88-5.97 (m, 2H), 6.69-6.85 (m, 3H), 6.91-7.00 (m, 2H), 7.02-7.11 (m, 4H), 7.29-7.36 (m, 2H), 7.93-8.04 (m, 1H), 8.17-8.25 (m, 1H).

Example 9

N-({4-[(2R,3R)-3-{[2-(1,3-Benzodioxol-5-yl)-2-hydroxyethyl]thio}-1-(4-methylphenyl)-4-oxoazetidin-2-yl]phenoxy}acetyl)glycyl-3-methyl-D-valine To a solution of {4-[(2R,3R)-3-{[2-(1,3-benzodioxol-5-yl)-2-oxoethyl]thio}-1-(4-methylphenyl)-4-oxoazetidin-2-yl]phenoxy}acetic acid (0.020 g, 0.040 mmol) and NMM (0.013 ml, 0.116 mmol) in DMF (3 ml) at RT was added TBTU (0.016 g, 0.050 mmol). The reaction mixture was stirred for 30 min after which glycyl-3-methyl-D-valine (0.009 g, 0.048 mmol) was added. The mixture was stirred for 15 h before the reaction was quenched by the addition of water (1 ml). The mixture was diluted with MeOH (2 ml) and added NaBH4 (0.017 g, 0.449 mmol). After 15 min the reaction was quenched by the addition of an aqueous solution of hydrochloric acid (1M, 1 ml) and most of the methanol was removed under reduced pressure. The remaining solution was purified by preparative HPLC using a gradient of 20-60% MeCN in a 0.1M ammonium acetate buffer as eluent. Freeze-drying of the pure fractions gave the desired product.

M/z (E−): 676.6. 1H NMR (DMSO, 400 MHz): d 0.87 (s, 9H), 2.16 (s, 3H), 2.76-2.90 (m, 2H), 3.77-3.84 (m, 2H), 4.01-4.08 (m, 1H), 4.16-422 (m, 1H), 4.48 (s, 2H), 4.56-4.64 (m, 1H), 4.94-4.99 (m, 1H), 5.89-5.95 (m, 2H), 6.69-6.84 (m, 3H), 6.91-6.98 (m, 2H), 7.02-7.10 (m, 4H), 7.28-7.35 (m, 2H), 7.78-7.88 (m, 1H), 8.19-8.26 (m, 1H).

Example 10

N-({4-[(2R,3R)-3-{[(2S or R)-2-(1,3-benzodioxol-5-yl)-2-hydroxyethyl]thio}-1-(4-fluorophenyl)-4-oxoazetidin-2-yl]phenoxy}acetyl)glycyl-3-methyl-D-valine The diastereomeric mixture of N-({4-[(2R,3R)-3-{[2-(1,3-benzodioxol-5-yl)-2-hydroxyethyl]thio}-1-(4-fluorophenyl)-4-oxoazetidin-2-yl]phenoxy}acetyl)glycyl-3-methyl-D-valine (Example 3); (10.8 mg, 0.016 mmol) was separated on two successive Chiralpak AD columns (250×20 mm, 10 μm) at 40 C using ethanol/heptane/formic acid/triethylamine (90/10/0.1/0.05) in 1.0 ml/min as mobile phase. UV-detection at 254 nm. The fraction of the first eluting diastereomer was concentrated and extracted between DCM and water. The organic phase was washed with water, dried with $Na_2SO_4$ and concentrated to yield the title compound. $^1$H-NMR (DMSO, 400 MHz): δ 0.90 (s, 9H), 2.80-2.95 (m, 2H), 3.84 (d, 2H), 4.08 (d, 1H), 4.29 (d, 1H), 4.53 (s, 2H), 4.63-4.68 (m, 1H), 5.05 (d, 1H), 5.96 (s, 2H), 6.74-6.82 (m, 2H), 6.86 (s, 1H), 7.00 (d, 2H), 7.12-7.20 (m, 2H), 7.21-7.28 (2H), 7.38 (d, 2H), 7.84 (d, 1H), 8.28 (t, 1H).

Example 11

N-({4-[(2R,3R)-3-{[(2R or S)-2-(1,3-benzodioxol-5-yl)-2-hydroxyethyl]thio}-1-(4-fluorophenyl)-4-oxo azetidin-2-yl]phenoxy}acetyl)glycyl-3-methyl-D-valine The diastereomeric mixture of N-({4-[(2R,3R)-3-{[2-(1,3-benzodioxol-5-yl)-2-hydroxyethyl]thio}-1-(4-fluorophenyl)-4-oxoazetidin-2-yl]phenoxy}acetyl)glycyl-3-methyl-D-valine ((10.8 mg, 0.016 mmol) was separated as described in Example 10. The title compound was obtained as the second eluting diastereomer. $^1$H-NMR (DMSO, 400 MHz): δ 0.90 (s, 9H), 2.84-2.95 (m, 2H), 3.84 (d, 2H), 4.07 (d, 1H), 4.27 (d, 1H), 4.53 (s, 2H), 4.60-4.65 (m, 1H), 5.07 (d, 1H), 5.96 (d, 2H), 6.74-6.84 (m, 2H), 6.86 (s, 1H), 7.00 (d, 2H), 7.12-7.20 (m, 2H), 7.21-7.28 (m, 2H), 7.38 (d, 2H), 7.83 (d, 1H), 8.28 (t, 1H).

Example 12

N-({4-[(2R,3R)-3-{[(2S or R)-2-(1,3-benzodioxol-5-yl)-2-hydroxyethyl]thiol}-1-(4-fluorophenyl)-4-oxoazetidin-2-yl]phenoxy}acetyl)glycyl-3-cyclohexyl-D-alanine The title compound was obtained as the first eluting diastereomer in the chromatographic separation of N-({4-[(2R,3R)-3-{[2-(1,3-benzodioxol-5-yl)-2-hydroxyethyl]thio}-1-(4-fluorophenyl)-4-oxoazetidin-2-yl]phenoxy}acetyl)glycyl-3-cyclohexyl-D-alanine (Example 2) (12 mg, 0.017 mmol). The chromatographic conditions used were as those described in Example 10. The title compound was obtained. $^1$H-NMR (DMSO, 400 MHz): δ 0.75-0.96 (m, 2H), 1.06-1.20 (m, 3H), 1.24-1.37 (m, 2H), 1.41-1.72 (m, 6H), 2.81-2.93 (m, 2H); 3.80 (d, 2H), 4.02 (t, 1H), 4.28 (d, 1H), 4.53 (s, 2H), 4.61-4.69 (m, 1H), 5.05 (d, 1H), 5.56 (d, 1H), 5.96 (s, 2H), 6.72-6.82 (m, 2H), 6.85 (s, 1H), 7.00 (d, 2H), 7.11-7.20 (m, 2H), 7.21-7.28 (m, 2H), 7.38 (d, 2H), 8.13 (d, 1H), 8.22 (t, 1H).

Example 13

N-({4-[(2R,3R)-3-{[(2R or S)-2-(1,3-benzodioxol-5-yl)-2-hydroxyethyl]thio}-1-(4-fluorophenyl)-4-oxoazetidin-2-yl]phenoxy}acetyl)glycyl-3-cyclohexyl-D-alanine The diastereomeric mixture of N-({4-[(2R,3R)-3-{[2-(1,3-benzodioxol-5-yl)-2-hydroxyethyl]thio}-1-(4-fluorophenyl)-4-oxoazetidin-2-yl]phenoxy}acetyl)glycyl-3-cyclohexyl-D-alanine 12 mg, 0.017 mmol) was separated as described in Example 12. The title compound was obtained as the second eluting. $^1$H-NMR (DMSO, 400 MHz): δ 0.76-0.96 (m, 2H), 1.05-1.21 (m, 3H), 1.24-1.37 (m, 2H), 1.41-1.72 (m, 6H), 2.84-2.94 (m, 2H), 3.79 (d, 2H), 4.18-4.26 (m, 1H), 4.27 (d, 1H), 4.52 (s, 2H), 4.59-4.66 (m, 1H), 5.07 (d, 1H), 5.56 (brs, 1H), 5.96 (d, 2H), 6.742-6.84 (m, 2H), 6.86 (s, 1H), 7.00 (d, 2H), 7.12-7.20 (m, 2H), 7.21-7.28 (m, 2H), 7.38 (d, 2H), 8.05-8.13 (m, 1H), 8.23 (t, 1H).

Example 14

N-({4-[(2R,3R)-3-{[2-(2,3-dihydro-1,4-benzodioxin-6-yl)-2-hydroxyethyl]thio}-1-(4-fluorophenyl)-4-oxoazetidin-2-yl]phenoxy}acetyl)glycyl-3-cyclohexyl-D-alanine To a solution of {4-[(2R,3R)-3-{[2-(2,3-dihydro-1,4-benzodioxin-6-yl)-2-oxoethyl]thio}-1-(4-fluorophenyl)-4-oxoazetidin-2-yl]phenoxy}acetic acid (0.020 g, 0.038 mmol) (Method 29) in DMF (1 ml) was added N-methylmorpholine (0.010 g, 0.099 mmol) followed by the addition of 3,4-dichlorophenol (0.008 g, 0.051 mmol) and TBTU (0.012 g, 0.038 mmol). After 2 h, the intermediate 3,4-dichlorophenylester (3,4-dichlorophenyl{4-[(2R,3R)-3-{[2-(2,3-dihydro-1,4-benzodioxin-6-yl)-2-oxoethyl]thio}-1-(4-fluorophenyl)-4-oxoazetidin-2-yl]phenoxy}acetate) had been formed. Glycyl-3-cyclohexyl-D-alanine (0.010 g, 0.046 mmol) and lithium chloride (0.024 g, 0.57 mmol) were added and the mixture was allowed to stir at room temperature for 1 h.

Methanol (1 ml) was added followed by the addition of NaBH$_4$ (0.022 g, 0.573 mmol). Full conversion to the corresponding alcohol had been obtained within 5 minutes. The mixture was purified through preparative HPLC using an eluent of 10-50% CH$_3$CN in 0.1M NH$_4$OAc buffer. Freeze drying of pure fractions afforded the desired. $^1$H NMR [(CD$_3$)$_2$SO), 400 MHz] δ 0.73-1.67 (m, 13H), 2.76-2.87 (m, 2H), 3.73 (d, 2H), 4.07-4.14 (m, 1H), 4.14-4.18 (m, 4H), 4.24-4.26 (m, 1H), 4.48 (s, 2H), 4.52-4.60 (m, 1H), 4.98-5.03 (m, 1H), 6.70-7.35 (m, 11H), 7.85-7.90 (m, 1H), 8.20-8.24 (m, 1H).

Example 15

N-{(2R)-2-[({4-[(2R,3R)-3-{[2-(2,3-dihydro-1,4-benzodioxin-6-yl)-2-hydroxyethyl]thio}-1-(4-fluorophenyl)-4-oxoazetidin-2-yl]phepoxy}acetyl)amino]-2-phenylacetyl}-L-serine {4-[(2R,3R)-3-{[2-(2,3-dihydro-1,4-benzodioxin-6-yl)-2-oxoethyl]thio}-1-(4-fluorophenyl)-4-oxoazetidin-2-yl]phenoxy}acetic acid (22 mg, 0.042 mmol); N-methylmorpholine (12 µl, 0.11 mmol), TBTU (15 mg, 0.046 mmol) and tert-butyl N-[(2R)-2-amino-2-phenylacetyl]-O-(tert-butyl)-L-serinate (22 mg, 0.063 mmol) were added to methylene chloride (2 ml) and the reaction mixture was stirred for 2 h. at room temperature. The solvent was evaporated under reduced pressure and formic acid (2 ml) was added. The mixture was stirred for 16 h. at room temperature and at 50° C. for 4 h. The solvent was evaporated at reduced pressure and then co-evaporated with toluene twice. To the residue was added methanol (1 ml) and NaBH4 (26 mg, 0.34 mmol) was added during 15 min. The reaction mixture was stirred for 2 h. at room temperature and was then purified by preparative HPLC using acetonitril/ammonium acetate:buffer (40:60) as eluent. The collected fractions were lyophilized to obtain the title compound.

($^1$H-NMR, 500 MHz, DMSO-d6): 2.8-2.9 (m, 2H), 3.2-3.3 (m, 1H), 3.45-3.5 (m, 1H), 4.2 (s, 4H), 4.3 (s, 1H), 4.55-4.7, 5.05 (d, 1H), 5.55 (bs, 1H), 5.65 (d, 1H), 6.7-7.4 (m, 16H), 8.15 (bs, 1H), 8.6 (d, 1H)

Example 16

(R)-3-Cyclohexyl-2-[2-(2-{4-[(2R,3R)-3-[(R os S)-2-(2,3-dihydro-benzo[1,4]dioxin-6-yl)-2-hydroxy-ethylsulfanyl]-1-(4-fluoro-phenyl)-4-oxo-azetidin-2-yl]-phenoxy}-acetylamino)-acetylamino]-propionic Acid To a solution {4-[(2R,3R)-3-[(R or S)-2-(2,3-dihydro-benzo[1,4]dioxin-6-yl)-2-hydroxy-ethylsulfanyl]-1-(4-fluoro-phenyl)-4-oxo-azetidin-2-yl]-phenoxy}-acetic acid (60 mg, 0.114 mmol) in DMF (2 mL) was added 4-chlorophenol (15 mg, 0.117 mmol), N-methylmorpholine (75 µL, 0.682 mmol) and TBTU (37 mg, 0.115 mmol). The mixture was stirred for 1 h at room temperature before (R)-2-(2-amino-acetylamino)-3-cyclohexyl-propionic acid (39 mg, 0.171 mmol) and lithium chloride (100 mg, 2.36 mmol) were added. The reaction mixture was stirred at room temperature for 13 h and then at 30° C. for 3 h. The reaction was quenched by the addition of water (2 mL) and the resulting mixture was purified by preparative HPLC using a gradient of 20-50% MeCN in a 0.1M ammonium acetate buffer as eluent. Freeze-drying of the pure fractions gave the desired product.

$^1$H-NMR (DMSO, 400 MHz): δ 0.70-0.95 (m, 2H), 1.00-1.73 (m, 11H), 2.80-2.92 (m, 2H), 3.77 (d, 2H), 4.12-4.24 (m, 5H), 4.27 (d, 1H), 4.51 (s, 2H), 4.54-4.61 (m, 1H), 5.04 (d,

1H), 5.53 (bs, 1H), 6.72-6.81 (m, 3H), 6.95-7.03 (m, 2H), 7.10-7.28 (m, 4H), 7.34-7.42 (m, 2H), 7.99 (d, 1H), 8.21-8.28 (m, 1H).

Example 17

(R)-2-[2-(2-{4-[(2R,3R)-3-R or S)-2-(2,3-Dihydro-benzo[1,4]dioxin-6-yl)-2-hydroxy-ethylsulfanyl]-1-(4-fluoro-phenyl)-4-oxo-azetidin-2-yl]-phenoxy}-acetylamino)-acetylamino)-3,3-dimethyl-butyric Acid To a solution of {4-[(2R,3R)-3-[(R or S)-2-(2,3-dihydro-benzo[1,4]dioxin-6-yl)-2-hydroxy-ethylsulfanyl]-1-(4-fluoro-phenyl)-4-oxo-azetidin-2-yl]-phenoxy}-acetic acid (19 mg, 0.036 mmol) in DMF (1.5 mL) was added N-methylmorpholine (10 μL, 0.089 mmol) and TBTU (13 mg, 0.040 mmol). The mixture was stirred for 30 min at room temperature before (R)-2-(2-amino-acetylamino)-3,3-dimethyl-butyric acid (7 mg, 0.037 mmol) was added. After 16 h, the reaction was quenched by the addition of water (0.5 mL). The solution was purified by preparative HPLC using a gradient of 20-40% MeCN in a 0.1M ammonium acetate buffer as eluent. Freeze-drying of the pure fractions gave the desired product.

$^1$H-NMR (DMSO, 500 MHz): δ 0.88 (s, 9H), 2.80-2.92 (m, 2H), 3.80 (d, 2H), 3.99 (d, 1H), 4.19 (s, 4H), 4.28 (d, 1H), 4.52 (s, 2H), 4.54-4.61 (m, 1H), 5.04 (d, 1H), 6.71-6.81 (m, 3H), 6.95-7.02 (m, 2H), 7.11-7.19 (m, 2H), 7.20-7.27 (m, 2H), 7.34-7.40 (m, 2H), 7.69-7.78 (m, 1H), 8.26-8.32 (m, 1H).

Example 18

(R)-2-[2-(2-{4-[(2R,3R)-3-[(R or S)-2-(2,3-Dihydro-benzo[1,4]dioxin-6-yl)-2-hydroxy-ethylsulfanyl]-1-(4-fluoro-phenyl)-4-oxo-azetidin-Z-yl]-phenoxy}-acetylamino)-acetylamino]-3-methyl-butyric Acid To a solution of {4-[(2R,3R)-3-[(R or S)-2-(2,3-dihydro-benzo[1,4]dioxin-6-yl)-2-hydroxy-ethylsulfanyl]-1-(4-fluoro-phenyl)-4-oxo-azetidin-2-yl]-phenoxy}-acetic acid (19 mg, 0.036 mmol) in DMF (1.5 mL) was added N-methylmorpholine (15 μL, 0.138 mmol) and TBTU (13 mg, 0.040 mmol). The mixture was stirred for 30 min at RT before (R)-2-(2-amino-acetylamino)-3-methyl-butyric acid (8 mg, 0.038 mmol) was added. After 16 h, the reaction was quenched by the addition of water (1 mL). This solution was purified by preparative HPLC using a gradient of 20-40% MeCN in a 0.1M ammonium acetate buffer as eluent. Freeze-drying of the pure fractions gave the desired product.

$^1$H-NMR (DMSO, 500 MHz): δ 0.76-0.84 (m, 6H), 1.95-2.06 (m, 1H), 2.81-2.92 (m, 2H), 3.79 (d, 2H), 3.93-4.01 (m, 1H), 4.19 (s, 4H), 4.28 (d, 1H), 4.52 (s, 2H), 4.55-4.61 (m, 1H), 5.04 (d, 1H), 6.71-6.81 (m, 3H), 6.96-7.02 (m, 2H), 7.11-7.18 (m, 2H), 7.20-7.27 (m, 2H), 7.34-7.40 (m, 2H), 7.65-7.74 (m, 1H), 8.26-8.33 (m, 1H).

The following compounds could be prepared by the procedure of Example 14, but wherein different protecting groups may be used.

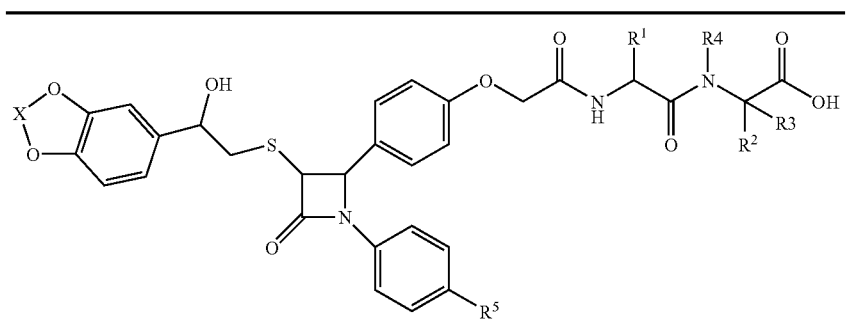

| X | R1 | R2 | R3 | R4 | R5 |
|---|---|---|---|---|---|
| CH$_2$CH$_2$ | H | CH$_2$C$_6$H$_5$ | H | H | F |
| CH$_2$CH$_2$ | H | CH$_2$C$_6$H$_5$-p-OH | H | H | F |
| CH$_2$CH$_2$ | H | CH$_2$C$_6$H$_5$-p-CN | H | H | F |
| CH$_2$CH$_2$ | H | CH$_2$CH$_2$CH$_2$NH$_2$ | H | H | F |
| CH$_2$CH$_2$ | H | CH$_2$CH$_2$CH$_2$CH$_2$NH$_2$ | H | H | F |
| CH$_2$CH$_2$ | H | C(CH$_3$)$_2$C$_6$H$_5$ | H | H | F |
| CH$_2$CH$_2$ | H | CH$_2$CH(CH$_3$)$_2$ | H | H | F |
| CH$_2$CH$_2$ | H | CH(CH$_3$)$_2$ | CH$_3$ | H | F |
| CH$_2$CH$_2$ | H | R$_2$, R$_4$ = CH$_2$CH$_2$CH$_2$ | H | R2, R4 = CH$_2$CH$_2$CH$_2$ | F |
| CH$_2$CH$_2$ | H | CH$_2$CH$_2$CH$_2$CH$_2$N(CH$_3$)$_2$ | H | H | F |
| CH$_2$CH$_2$ | H | CH$_2$SC(CH$_3$)$_3$ | H | H | F |
| CH$_2$CH$_2$ | H | CH$_2$CH$_2$CH$_2$CH$_3$ | CH$_2$CH$_2$CH$_2$CH$_3$ | H | F |
| CH$_2$CH$_2$ | H | CH$_2$C$_6$H$_5$ | H | H | H |
| CH$_2$CH$_2$ | H | CH$_2$C$_6$H$_5$-p-OH | H | H | H |
| CH$_2$CH$_2$ | H | CH$_2$C$_6$H$_5$-p-CN | H | H | H |
| CH$_2$CH$_2$ | H | cyclohexyl | H | H | H |
| CH$_2$CH$_2$ | H | CH$_2$cyclohexyl | H | H | H |
| CH$_2$CH$_2$ | H | CH$_2$CH$_2$CH$_2$NH$_2$ | H | H | H |
| CH$_2$CH$_2$ | H | CH$_2$CH$_2$CH$_2$CH$_2$NH$_2$ | H | H | H |
| CH$_2$CH$_2$ | H | C(CH$_3$)$_2$C$_6$H$_5$ | H | H | H |
| CH$_2$CH$_2$ | H | CH(CH$_3$)$_2$ | H | H | H |
| CH$_2$CH$_2$ | H | CH$_2$CH(CH$_3$)$_2$ | H | H | H |
| CH$_2$CH$_2$ | H | CH(CH$_3$)$_2$ | CH$_3$ | H | H |
| CH$_2$CH$_2$ | H | R$_2$, R$_4$ = CH$_2$CH$_2$CH$_2$ | H | R2, R4 = CH$_2$CH$_2$CH$_2$ | H |
| CH$_2$CH$_2$ | H | CH$_2$CH$_2$CH$_2$CH$_2$N(CH$_3$)$_2$ | H | H | H |
| CH$_2$CH$_2$ | H | CH$_2$SC(CH$_3$)$_3$ | H | H | H |

-continued

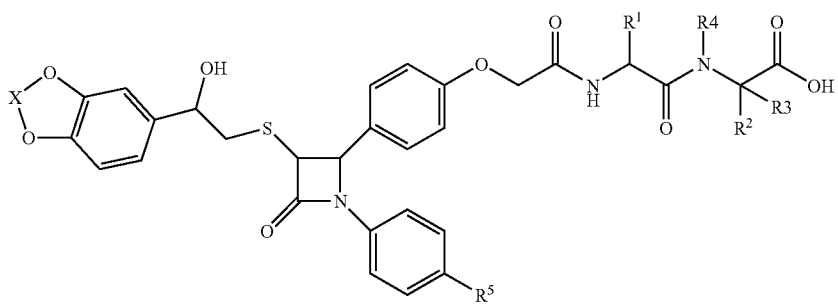

| X | R1 | R2 | R3 | R4 | R5 |
|---|---|---|---|---|---|
| $CH_2CH_2$ | H | $CH_2CH_2CH_2CH_3$ | $CH_2CH_2CH_2CH_3$ | H | H |
| $CH_2CH_2$ | H | $C(CH_3)_3$ | H | H | H |
| $CH_2CH_2$ | H | $CH_2C_6H_5$ | H | H | Cl |
| $CH_2CH_2$ | H | $CH_2C_6H_5$-p-OH | H | H | Cl |
| $CH_2CH_2$ | H | $CH_2C_6H_5$-p-CN | H | H | Cl |
| $CH_2CH_2$ | H | cyclohexyl | H | H | Cl |
| $CH_2CH_2$ | H | $CH_2$cyclohexyl | H | H | Cl |
| $CH_2CH_2$ | H | $CH_2CH_2CH_2NH_2$ | H | H | Cl |
| $CH_2CH_2$ | H | $CH_2CH_2CH_2CH_2NH_2$ | H | H | Cl |
| $CH_2CH_2$ | H | $C(CH_3)_2C_6H_5$ | H | H | Cl |
| $CH_2CH_2$ | H | $CH(CH_3)_2$ | H | H | Cl |
| $CH_2CH_2$ | H | $CH_2CH(CH_3)_2$ | H | H | Cl |
| $CH_2CH_2$ | H | $CH(CH_3)_2$ | $CH_3$ | H | Cl |
| $CH_2CH_2$ | H | $R_2, R_4 = CH_2CH_2CH_2$ | H | $R_2, R_4 = CH_2CH_2CH_2$ | Cl |
| $CH_2CH_2$ | H | $CH_2CH_2CH_2CH_2N(CH_3)_2$ | H | H | Cl |
| $CH_2CH_2$ | H | $CH_2SC(CH_3)_3$ | H | H | Cl |
| $CH_2CH_2$ | H | $CH_2CH_2CH_2CH_3$ | $CH_2CH_2CH_2CH_3$ | H | Cl |
| $CH_2CH_2$ | H | $C(CH_3)_3$ | H | H | Cl |
| $CH_2CH_2$ | H | $CH_2C_6H_5$ | H | H | CH3 |
| $CH_2CH_2$ | H | $CH_2C_6H_5$-p-OH | H | H | CH3 |
| $CH_2CH_2$ | H | $CH_2C_6H_5$-p-CN | H | H | CH3 |
| $CH_2CH_2$ | H | cyclohexyl | H | H | CH3 |
| $CH_2CH_2$ | H | $CH_2$cyclohexyl | H | H | CH3 |
| $CH_2CH_2$ | H | $CH_2CH_2CH_2NH_2$ | H | H | CH3 |
| $CH_2CH_2$ | H | $CH_2CH_2CH_2CH_2NH_2$ | H | H | CH3 |
| $CH_2CH_2$ | H | $C(CH_3)_2C_6H_5$ | H | H | CH3 |
| $CH_2CH_2$ | H | $CH(CH_3)_2$ | H | H | CH3 |
| $CH_2CH_2$ | H | $CH_2CH(CH_3)_2$ | H | H | CH3 |
| $CH_2CH_2$ | H | $CH(CH_3)_2$ | $CH_3$ | H | CH3 |
| $CH_2CH_2$ | H | $R_2, R_4 = CH_2CH_2CH_2$ | H | $R_2, R_4 = CH_2CH_2CH_2$ | CH3 |
| $CH_2CH_2$ | H | $CH_2CH_2CH_2CH_2N(CH_3)_2$ | H | H | CH3 |
| $CH_2CH_2$ | H | $CH_2SC(CH_3)_3$ | H | H | CH3 |
| $CH_2CH_2$ | H | $CH_2CH_2CH_2CH_3$ | $CH_2CH_2CH_2CH_3$ | H | CH3 |
| $CH_2CH_2$ | H | $C(CH_3)_3$ | H | H | CH3 |
| $CH_2$ | H | $CH_2C_6H_5$-p-OH | H | H | F |
| $CH_2$ | H | $CH_2C_6H_5$-p-OH | H | H | F |
| $CH_2$ | H | $CH_2C_6H_5$-p-CN | H | H | F |
| $CH_2$ | H | cyclohexyl | H | H | F |
| $CH_2$ | H | $CH_2CH_2CH_2NH_2$ | H | H | F |
| $CH_2$ | H | $CH_2CH(CH_3)_2$ | H | H | F |
| $CH_2$ | H | $CH(CH_3)_2$ | $CH_3$ | H | F |
| $CH_2$ | H | $R_2, R_4 = CH_2CH_2CH_2$ | H | $R_2, R_4 = CH_2CH_2CH_2$ | F |
| $CH_2$ | H | $CH_2CH_2CH_2CH_2N(CH_3)_2$ | H | H | F |
| $CH_2$ | H | $CH_2SC(CH_3)_3$ | H | H | F |
| $CH_2$ | H | $CH_2CH_2CH_2CH_3$ | $CH_2CH_2CH_2CH_3$ | H | F |
| $CH_2$ | H | $CH_2C_6H_5$ | H | H | H |
| $CH_2$ | H | $CH_2C_6H_5$-p-OH | H | H | H |
| $CH_2$ | H | $CH_2C_6H_5$-p-CN | H | H | H |
| $CH_2$ | H | cyclohexyl | H | H | H |
| $CH_2$ | H | $CH_2$cyclohexyl | H | H | H |
| $CH_2$ | H | $CH_2CH_2CH_2NH_2$ | H | H | H |
| $CH_2$ | H | $CH_2CH_2CH_2CH_2NH_2$ | H | H | H |
| $CH_2$ | H | $C(CH_3)_2C_6H_5$ | H | H | H |
| $CH_2$ | H | $CH(CH_3)_2$ | H | H | H |
| $CH_2$ | H | $CH_2CH(CH_3)_2$ | H | H | H |
| $CH_2$ | H | $CH(CH_3)_2$ | $CH_3$ | H | H |
| $CH_2$ | H | $R_2, R_4 = CH_2CH_2CH_2$ | H | $R_2, R_4 = CH_2CH_2CH_2$ | H |
| $CH_2$ | H | $CH_2CH_2CH_2CH_2N(CH_3)_2$ | H | H | H |
| $CH_2$ | H | CH2OH | H | H | H |
| $CH_2$ | H | $CH_2SC(CH_3)_3$ | H | H | H |
| $CH_2$ | H | $CH_2CH_2CH_2CH_3$ | $CH_2CH_2CH_2CH_3$ | H | H |
| $CH_2$ | H | $C(CH_3)_3$ | H | H | H |

Preparations of Starting Material for the Above Examples

N-[(4-{(2R,3R)-1-(4-fluorophenyl)-3-[(3-nitropyridin-2-yl)dithio]-4-oxoazetidin-2-yl}phenoxy)acetyl]glycyl-3-methyl-D-valine To a solution of ten-butyl(4-{(2R,3R)-1-(4-fluorophenyl)-3-[(3-nitropyridin-2-yl)dithio]-4-oxoazetidin-2-yl}phenoxy)acetate (Method 6) (0.250 g, 0.448 mmol) in dichloromethane (5 ml) was added trifluoroacetic acid (1 g). After 2 h, full conversion to the corresponding acid was obtained. The reaction mixture was concentrated to give the acid as a yellow solid. To a solution of this acid and N-methylmorpholine (0.177 g, 1.755 mmol) in DMF (4 ml) under an atmosphere of nitrogen was added TBTU (0.183 g, 0.570 mmol). After 1 h, glycyl-3-methyl-D-valine trifluoroacetate salt (Method 10)(0.159 g, 0.526 mmol) was added. The reaction was allowed to stir for 10 minutes after which it was quenched by the addition of water (1 ml). Preparative HPLC of the mixture using an eluent of 0-50% $CH_3CN$ in 0.1M $NH_4OAc$ buffer followed by freeze drying of pure fractions afforded the desired compound. m/z: 672.6 (M+1). $^1H$ NMR [$(CD_3)_2SO$], 400 MHz] δ 0.88 (s, 9H), 3.80-3.84 (m, 2H), 4.02-4.06 (m, 1H), 4.49-4.67 (m, 3H), 5.21-5.26 (m, 1H), 6.51-7.49 (m, 10H), 7.79-7.81 (m, 1H), 7.95 (dd, 1H), 8.23-8.32 (m, 1H).

N-({4-[(2R,3R)-3-{[2-(1,3-benzodioxol-5-yl)-2-hydroxyethyl]thio}-1-(4-fluorophenyl)-4-oxoazetidin-2-yl]phenoxy}acetyl)glycine To a stirred solution of {4-[(2R,3R)-3-{[2-(1,3-benzodioxol-5-yl)-2-oxoethyl]thio}-1-(4-fluorophenyl)-4-oxoazetidin-2-yl]phenoxy}acetic acid (Method 7) 208 mg, 0.41 mmol) in DCM (16 ml) were added N-methylmorpholine (130 μl, 1.18 mmol), tert-butyl glycinate hydrochloride (102.3 mg, 0.61 mmol) and TBTU (180.8 mg, 0.56 mmol). The reaction mixture was stirred at ambient temperature overnight. The formation of the intermediate tert-butyl N-({4-[(2R,3R)-3-{[2-(1,3-benzodioxol-5-yl)-2-oxoethyl]thio}-1-(4-fluorophenyl)-4-oxoazetidin-2-yl]phenoxy}acetyl)glycinate confirmed. M/z: 623.88 (M+1) and 621.84 (M−1). The solvent was removed under reduced pressure and the residue was passed through a short silica gel pad and eluted with DCM:EtOAc 8:2. The collected fractions were concentrated under reduced pressure. The crude oil (0.818 mg) was dissolved in DCM (6 ml) and TFA (4 ml) was added and the mixture was stirred for 1 hour. The formation of the ketone of the title compound was confirmed. M/z: 567.74 (M+1) and 565.79 (M−1). The solvent was co-evaporated with toluene under reduced pressure. The residue was dissolved in methanol (8 ml) and sodium borohydride (128.6 mg, 3.40 mmol) and the mixture was stirred for 40 minutes Ammonium acetate (200 mg) was added and the solvent was removed under reduced pressure. The residue was purified with preparative HPLC on a C8 column, UV 240/260 nm. A gradient from 20 to 50% MeCN in 0.1M $NH_4OAc$ buffer was used as eluent. The pure fractions were collected and the MeCN was removed under reduced pressure. The remaining water solution was acidified to pH 1 with HCl (1M) and extracted with DCM. The organic phase was passed through a phase separator and concentrated under reduced pressure. The residue was dissolved in MeCN and water. After lyophilisation, the title compound was obtained. H-NMR (400 MHz, DMSO-$d_6$): 2.78-2.89 (m, 2H), 3.76 (d, 2H), 4.22-4.25 (m, 1H), 4.49 (s, 2H), 4.55-4.64 (m, 1H), 5.01 (d, 0.5H), 5.03 (d, 0.5H), 5.52 (bs, 1H), 5.90-5.94 (m, 2H), 6.70-6.79 (m, 2H), 6.82 (s, 1H), 6.96 (d, 2H), 7.08-7.16 (m, 2H), 7.18-7.24 (m, 2H), 7.34 (d, 2H), 8.34 (t, 1H). M/z: 567.52 (M−1).

(4S)-3-{[(4-Methoxybenzyl)thio]acetyl}-4-phenyl-1,3-oxazolidin-2-one

[(4-Methoxybenzyl)thio]acetic acid (1.3 g, 6.1 mmol) was dissolved in dry $CH_2Cl_2$ (40 ml) and given 0° C. N,N'-Dicyclohexylcarbodiimide (DCC, 6.1 g, 6.1 mmol) and 4-(dimethylamino)pyridine (DMAP, 1.6 g, 12.9 mmol) were added and the mixture was stirred for 30 minutes. (S)-(+)-4-Phenyl-2-oxazolidinone (1.0 g, 6.1 mol) was added and the mixture was stirred at room temperature for 24 hours. The mixture was filtered, concentrated under reduced pressure and purified by flash-chromatography (Hex:EtOAc 8:2 then 1:1). This afforded the title compound.
$^1H$-NMR (CDCl$_3$, 200 MHz): δ 3.46-3.59 (m, 3H), 3.74-3.76 (m, 4H), 4.23-4.28 (m, 4.68 (t, J=8.8 Hz, 1H), 5.38-5-42 (m, 1H), 6.78 (d, J=8.6 Hz, 2H), 7.14 (d, J=8.6 Hz, 2H), 7.32-7.40 (m, 5H).

tert-Butyl(4-{(1R)-1-[(4-fluorophenyl)amino]-2-[(4-methoxybenzyl)thio]-3-oxo-3-[(4S)-2-oxo-4-phenyl-1,3-oxazolidin-3-yl]propyl}phenoxy)acetate TiCl$_4$ (1M in CH$_2$Cl$_2$, 12.6 mL, 12.6 mmol) was added to a solution of tetraisopropyl orthotitanate (1.24 mL, 4.2 mmol) in CH$_2$Cl$_2$ (80 mL) held at 0° C. under inert atmosphere. The mixture was stirred for 15 minutes, then (4S)-3-{[(4-methoxybenzyl)thio]acetyl}-4-phenyl-1,3-oxazolidin-2-one (Method 3) (6.0 g, 16.8 mmol) in dry CH$_2$Cl$_2$ (60 mL) was added dropwise over 30 minutes and the mixture was stirred for ten minutes. Then tert-butyl (4-{(E)-[(4-fluorophenyl)imino]methyl}phenoxy)acetate (Method 18) (11.1 g, 33.6 mmol) in dry CH$_2$Cl$_2$ (60 mL) was added dropwise over 30 minutes, the mixture was given −40° C. and stirred for 20 minutes. Ethyl diisopropyl amine (5.8 mL, 33.6 mmol) in 20 mL CH$_2$Cl$_2$ was added dropwise over 20 minutes and the mixture was stirred at −40° C. for 90 minutes. The mixture was then given −78° C., added isopropanol (50 mL) and slowly given room temperature over two hours. H$_2$O (100 mL) was added and the mixture was stirred for 20 minutes at room temperature and then extracted twice with diethyl ether. The combined organic layer was washed with water, dried (MgSO$_4$) and concentrated under reduced pressure. The crude product was dissolved in methanol and an off-white precipitate formed. Filtration and drying afforded the title compound.
$^1H$-NMR (CDCl$_3$, 200 MHz): δ 1.5 (s, 9H), 3.65 (s, 1H), 3.8 (s, 3H), 4.1 (m, 1H), 4.4-4.6 (m, 4H), 5.0-5.2 (m, 2H), 5.4 (m, 1H), 6.4-6.6 (m, 2H), 6.7-7-4 (m, 15H).

tert-Butyl (4-{(2R,3R)-1-(4-fluorophenyl)-3-[(4-methoxybenzyl)thio]-4-oxoazetidin-2-yl}phenoxy)acetate tert-Butyl (4-{(1R)-1-[(4-fluorophenyl)amino]-2-[(4-methoxybenzyl)thio]-3-oxo-3-[(4S)-2-oxo-4-phenyl-1,3-oxazolidin-3-yl]propyl}phenoxy)acetate (Method 4) (9.3 g, 13.5 mmol) was dissolved in dry toluene (500 mL) and heated to 90° C. under inert atmosphere. N,O-Bis(trimethylsilyl)acetamide (BSA, 9.9 mL, 40.6 mmol) was added and the mixture was stirred at 90° C. for one hour. The mixture was then given 45° C. and tetrabutylammonium fluoride (TBAF, 1 g) was added. The mixture was stirred at 45° C. for 24 hours. After cooling, the mixture was concentrated under reduced pressure and purified by flash-chromatography (Hex:EtOAc 6:1 then 5:1 then 4:1). This afforded the title compound.

$^1$H-NMR (CDCl$_3$, 200 MHz): δ 1.5 (s, 9H), 3.7 (s, 3H), 3.9 (m, 3H), 4.5 (m, 3H), 6.7 (d, 2H), 6.8-7.0 (m, 4H), 7.0-7.2 (m, 6H).

tert-Butyl (4-{(2R,3R)-1-(4-fluorophenyl)-3-[(3-nitropyridin-2-yl)dithio]-4-oxoazetidin-2-yl}phenoxy)acetate tert-Butyl (4-{(2R,3R)-1-(4-fluorophenyl)-3-[(4-methoxybenzyl)thio]-4-oxoazetidin-2-yl}phenoxy)acetate (Method 5) (2.54 g, 4.86 mmol) was dissolved in CH$_2$Cl$_2$ (60 mL) and given 0° C. under inert atmosphere. 3-Nitro-2-pyridinesulfenyl chloride (1.11 g, 5.82 mmol) was added and the mixture was stirred for two hours at 0° C., the one hour at room temperature. Concentration under reduced pressure and purification by flash-chromatography (Hex:EtOAc 2:1) afforded the title compound.

$^1$H-NMR (CDCl$_3$, 200 MHz): δ 1.6 (s. 9H), 4.3 (d, 1H), 4.5 (s, 2H), 5.2 (d, 1H), 6.8-7.0 (m, 4H), 7.1-7.3 (m, 4H), 7.4 (m, 1H) 8.5 (d, 1H), 8.9 (d, 1H).

{4-[(2R,3R)-3-{[2-(1,3-Benzodioxol-5-yl)-2-oxoethyl]thio}-1-(4-fluorophenyl)-4-oxoazetidin-2-yl]phenoxy}acetic Acid tert-Butyl (4-{(2R,3R)-1-(4-fluorophenyl)-3-[(3-nitropyridin-2-yl)dithio]-4-oxoazetidin-2-yl}phenoxy)acetate (Method 6) (0.050 g, 0.090 mmol) was dissolved in acetone (4 ml) at room temperature. Water (0.5 ml) and triphenyl phosphine (0.025 g, 0.095 mmol) were added and the mixture was stirred at room temperature for 30 minutes. The solvent was removed under reduced pressure and the residue was immediately dissolved in DCM (4 ml). Benzodioxol-5-yl)-2-bromoethanone (0.055 g, 0.226 mmol) and Et$_3$N (0.030 ml, 0.272 mmol) were added and the mixture was stirred at room temperature for 18 hours. The reaction mixture was concentrated under reduced pressure and the residue was dissolved in formic acid (4 ml). The solution was stirred at RT for 90 min before the solvent was removed under reduced pressure. The residue was purified by preparative HPLC using a gradient of 20-60% MeCN in a 0.1M ammonium acetate buffer as eluent. Freeze-drying of the pure fractions gave the desired product.

M/z: 510.8. $^1$H NMR (DMSO, 400 MHz): δ 4.26 (ABq, 2H), 4.29 (d, 1H), 4.33 (bs, 2H), 5.11 (d, 1H), 6.10-6.15 (m, 2H), 6.79-6.84 (m, 2H), 6.97-7.02 (m, 1H), 7.10-7.32 (m, 6H), 7.38-7.42 (m, 1H), 7.54-7.60 (m, 1H).

{4-[(2R,3R)-3-{[2-(1,3-Benzodioxol-5-yl)-2-hydroxyethyl]thio}-1-(4-fluorophenyl)-4-oxoazetidin-2-yl]phenoxy}acetic Acid To a solution of {4-[(2R,3R)-3-{[2-(1,3-Benzodioxol-5-yl)-2-oxoethyl]thio}-1-(4-fluorophenyl)-4-oxoazetidin-2-yl]phenoxy}acetic acid (Method 7) (0.010 g, 0.020 mmol) in methanol (2 ml) was added NaBH4 (0.010 g, 0.265 mmol). After 15 min the reaction was quenched by the addition of an aqueous solution of hydrochloric acid (1M, 1 ml) and most of the methanol was removed under reduced pressure. The remaining solution was purified by preparative HPLC using a gradient of 20-60% MeCN in a 0.1M ammonium acetate buffer as eluent. Freeze-drying of the pure fractions gave the product.

M/z (ES−): 510.8. 1H NMR (DMSO, 500 MHz): δ 2.82-2.94 (m, 2H), 4.27-4.30 (m, 1H), 4.60-4.68 (m, 3H), 5.03-5.08 (m, 1H), 5.56 (bs, 1H), 5.95-5.99 (m, 2H), 6.73-6.96 (m, 5H), 7.13-7.28 (m, 4H), 7.34-7.39 (m, 2H).

Glycyl-3-cyclohexyl-D Alanine

N-(tert-butoxycarbonyl)glycine (2.0 g, 11.4 mmol) and DIPEA (4.0 g, 31 mmol) were dissolved in methylene chloride (25 ml). TBTU (4.1 g, 12.8 mmol) was added and the mixture was stirred for 15 min at room temperature. 3-cyclohexyl-D-alanine (2.1 g, 12.2 mmol) was added and the reaction mixture was stirred over night at room temperature. The reaction mixture was transferred to a separation funnel and was then extracted with a water/acetic acid solution (100 ml 5% acetic acid). The organic layer was separated and evaporated under reduced pressure. The residue was dissolved in formic acid (20 ml) and the mixture was stirred over night at 40° C. The formic acid was removed under reduced pressure. The residue was washed with water (50 ml) and then stirred in aceton (25 ml) for 1 h at room temperature. The solid material was filtered off and washed with aceton (20 ml). The title compound was obtained.

$^1$H-NMR, 300 MHz, CD3COOD): 0.8-1.9 (m, 13H), 3.9-4.1 (m, 2H), 4.55-4.65 (m, 1H).

Glycyl-3-methyl-D-valine Trifluoroacetate

To a 30° C. solution of N-(tert-butoxycarbonyl)glycine (0.450 g, 2.569 mmol) and N-methylmorpholine (1.30 g, 12.84 mmol) in CH$_2$Cl$_2$ (50 ml) was added TBTU (0.99 g, 3.08 mmol). After 1.5 h, D-tert-leucine (0.303 g, 2.31 mmol) was added. After 30 minutes, the reaction was quenched by the addition of water (1 ml). The mixture was concentrated and the residue was purified through preparative HPLC using an eluent of 0-40% CH$_3$CN in 0.1M NH$_4$OAc buffer. Pure fractions were collected and concentrated. To the residue were added CH$_2$Cl$_2$ (10 ml) and TFA (3 ml). Full conversion to the corresponding amino acid was obtained after 30 minutes. The reaction mixture was concentrated to give the desired compound. $^1$H NMR [(CD$_3$)$_2$SO), 400 MHz] ▯0.94 (s, 9H), 3.60-3.67 (m, 2H), 4.16 (d, 1H), 7.90-8.00 (m, 3H), 8.47 (d, 1H).

Ethyl {[2-(1,3-benzodioxol-5-yl)-2-oxoethyl]thio}acetate

Ethyl 2-mercaptoacetate (9.68 mL, 88.3 mmol) was added dropwise to a suspension of K$_2$CO$_3$ (12.2 g, 88.3 mmol) and 1-(1,3-benzodioxol-5-yl)-2-bromoethanone (21.4 g, 88.3 mmol) in dry acetone (100 mL). The mixture was stirred at reflux for seven hours, cooled at an icebath and added 200 mL water. Diethyl ether (400 mL) was added and the phases were separated. The aqueous layer was extracted with diethyl ether (200 mL) and the combined organic layers were washed with brine (200 mL), dried (MgSO$_4$) and concentrated. This afforded the title compound.

$^1$H-NMR (CDCl$_3$, 300 MHz): δ 1.2-1.3 (t, 3H), 3.3 (s, 2H), 4.0 (s, 2H), 4.1-4.2 (q, 2H), 6.1 (s, 2H), 6.9 (d, 1H), 7.3 (s, 1H), 7.6 (d, 1H).

Ethyl ({[2-(1,3-benzodioxol-5-yl)-5,5-dimethyl-1,3-dioxan-2-yl]methyl}thio)acetate Ethyl {[2-(1,3-benzodioxol-5-yl)-2-oxoethyl]thio}acetate (Method 11) (15.8 g, 0.056 mol) was dissolved in benzene (500 mL) and 2,2-dimethyl-1,3-propanediol (46.6 g, 0.45 mol) and p-toluene sulfonic acid (cat., 500 mg) were added. The mixture was stirred at reflux in a Dean-Stark apparatus for two hours, given room temperature and concentrated under reduced pressure. The resulting white solid was dissolved in CH$_2$Cl$_2$ (500 mL) and washed twice with water (300 mL) and brine (300 mL). The organic layer was dried (MgSO$_4$) and concentrated under reduced pressure. The crude oil was purified by flash-chromatography (heptane:EtOAc 4:1) to afford the desired product.

$^1$H-NMR (CDCl$_3$, 200 MHz): δ 0.6 (s, 3H), 1.2-1.4 (m, 6H), 2.9 (s, 2H), 3.2 (s, 2H), 3.4 (s, 4H), 4.1 (q, 2H), 6.0 (s, 2H), 6.8-7.0 (m, 3H).

({[2-(1,3-Benzodioxol-5-yl)-5,5-dimethyl-1,3-dioxan-2-yl]methyl}thio)acetic Acid Ethyl ({[2-(1,3-benzodioxol-5-yl)-5,5-dimethyl-1,3-dioxan-2-yl]methyl}thio)acetate (Method 12) (14.2 g, 0.039 mol) was dissolved in THF (300 mL) and cooled to 0° C. LiOH (4.87 g, 0.12 mol) in water (100 mL) was added, and the mixture was given room temperature and stirred for 19 hours. The solvents were evaporated, the crude product was added water and extracted with diethyl ether. The aqueous layer was added 1M HCl until pH=3 and extracted twice with CH$_2$Cl$_2$. The combined CH$_2$Cl$_2$ layers were dried (Na$_2$SO$_4$) and concentrated under reduced pressure to afford the desired product.

$^1$H-NMR (CDCl$_3$, 300 MHz): δ 0.6 (s, 3H), 1.3 (s, 3H), 3.0 (s, 2H), 3.4 (s, 2H), 3.5 (m, 4H), 6.0 (s, 2H), 6.8-7.0 (m, 3H).

(4S)-3-[({[2-(1,3-Benzodioxol-5-yl)-5,5-dimethyl-1,3-dioxan-2-yl]methyl}thio)acetyl]-4-phenyl-1,3-oxazolidin-2-one ({[2-(1,3-Benzodioxol-5-yl)-5,5-dimethyl-1,3-dioxan-2-yl]methyl}thio)acetic acid (Method 13) (12.7 g, 37.4 mmol) was dissolved in dry CH$_2$Cl$_2$ (150 ml) and given 0° C. N,N'-Dicyclohexylcarbodiimide (DCC, 8.48 g, 37.4 mmol) and 4-(dimethylamino)pyridine (DMAP, 9.13 g, 74.8 mmol) were added and the mixture was stirred at 0° C. for 20 minutes. (S)-(+)-4-Phenyl-2-oxazolidinone (6.10 g, 37.4 mmol) was added and the mixture was stirred at room temperature for 16 hours. The mixture was filtrated, concentrated under reduced pressure and purified by flash-chromatography (heptane:EtOAc 2:1). This afforded the title compound.

$^1$H-NMR (CDCl$_3$, 200 MHz): δ 0.6 (s, 3H), 1.3 (s, 3H), 2.8 (s, 2H), 3.4 (m, 4H), 3.9 (s, 2H), 4.3 (dd, 1H), 4.7 (t, 1H), 5.4 (dd, 1H), 6.0 (s, 2H), 6.8-7.0 (m; 311) 7.2-7.5 (m, 6H).

tert-Butyl (4-{(1R,2R)-2-({[2-(1,3-benzodioxol-5-yl)-5,5-dimethyl-1,3-dioxan-2-yl]methyl}thio)-1-[(4-fluorophenyl)amino]-3-oxo-3-[(4S)-2-oxo-4-phenyl-1,3-oxazolidin-3-yl]propyl}phenoxy)acetate Tetraisopropyl orthotitanate (2.74 mL, 9.3 mmol) was added to a solution of TiCl$_4$ (1M in CH$_2$Cl$_2$, 27.8 mL, 27.8 mmol) in CH$_2$Cl$_2$ (150 mL) held at 0° C. under inert atmosphere. The mixture was stirred for ten minutes, then (4S)-3-[({[2-(1,3-benzodioxol-5-yl)-5,5-dimethyl-1,3-dioxan-2-yl]methyl}thio)acetyl]-4-phenyl-1,3-oxazolidin-2-one (Method 14) (18.0 g, 37.1 mmol) in dry CH$_2$Cl$_2$ (200 mL) was added dropwise over 30 minutes and the mixture was stirred for ten minutes at 0° C. Then tert-butyl (4-{[(4-fluorophenyl)imino]methyl}phenoxy)acetate (Method 18) (24.4 g, 74.1 mmol) in dry CH$_2$Cl$_2$ (200 mL) was added dropwise over 30 minutes and the mixture was given −30° C. and stirred for 20 minutes. Ethyl diisopropyl amine (12.7 mL, 74.1 mmol) was added dropwise over 10 minutes and the mixture was stirred at −30° C. for 90 minutes. The mixture was then given −78° C., added isopropanol (70 mL) and slowly given room temperature over one hour. 10% NH$_4$Cl (100 mL) was added and the mixture was stirred for 15 minutes at room temperature, added brine (250 mL) and then extracted twice with 600 mL diethyl ether. The combined organic layers were dried (MgSO$_4$) and concentrated under reduced pressure. Purification by flash-chromatography (heptane:EtOAc 4:1 then 2:1) afforded the desired product.

$^1$H-NMR (CDCl$_3$, 200 MHz): δ 0.6 (s, 3H), 1.2 (s, 3H), 1.5 (s, 9H), 2.6-2.8 (m, 2H), 3.2-3.6 (m, 4H), 4.2 (m, 1H), 4.5 (s, 2H), 4.6-4.8 (m, 2H), 5.4 (d, 1H), 5.7 (d, 1H), 6.0 (s, 2H), 6.4 (m, 1H), 6.6-7.5 (m, 15H).

MS (CI) m/z: 837.2 (M$^+$+Na, 100), 838.3 (50), 839.3 (10), 840.2 (5).

tert-Butyl {4-[(2R,3R)-3-({[2-(1,3-benzodioxol-5-yl)-5,5-dimethyl-1,3-dioxan-2-yl]methyl}thio)-1-(4-fluorophenyl)-4-oxoazetidin-2-yl]phenoxy}acetate tert-Butyl (4-{(1R,2R)-2-({[2-(1,3-benzodioxol-5-yl)-5,5-dimethyl-1,3-dioxan-2-yl]methyl}thio)-1-[(4-fluorophenyl)amino]-3-oxo-3-[(4S)-2-oxo-4-phenyl-1,3-oxazolidin-3-yl]propyl}phenoxy)acetate (Method 15) (22.30 g, 27.4 mmol) was dissolved in dry toluene (800 mL) and heated to 90° C. under inert atmosphere. N,O-Bis(trimethylsilyl)acetamide (BSA, 20.1 mL, 82.1 mmol) was added and the mixture was stirred at 90° C. for one hour. The mixture was then given 45° C. and tetrabutylammonium fluoride trihydrate (TBAF, cat., 1 g) was added and the mixture was stirred at 45° C. for 1 hour. The mixture was then concentrated under reduced pressure and purified by flash-chromatography (heptane:EtOAc 5:1). This afforded 10.0 g (56%) of the title compound as a white solid.

$^1$H-NMR (CDCl$_3$, 200 MHz): δ 0.6 (s, 3H), 1.2 (s, 3H), 1.5 (s, 9H), 3.0 (q, 2H), 3.3-3.6 (m, 4H), 4.0 (d, 1H), 4.5 (s, 2H), 4.8 (d, 1H), 6.0 (s, 2H), 6.8-7.0 (m, 8H), 7.2-7.3 (m, 3H).

{4-[(2R,3R)-3-{[2-(1,3-Benzodioxol-5-yl)-2-oxoethyl]thio}-1-(4-fluorophenyl)-4-oxoazetidin-2-yl]phenoxy}acetic acid tert-Butyl {4-[(2R,3R)-3-({[2-(1,3-benzodioxol-5-yl)-5,5-dimethyl-1,3-dioxan-2-yl]methyl}thio)-1-(4-fluorophenyl)-4-oxoazetidin-2-yl]phenoxy}acetate (Method 16) (10.0 g, 15.35 mmol) was dissolved in formic acid (100 mL) at room temperature and stirred for two hours. The mixture was concentrated under reduced pressure (temperature<30° C.) and the crude oil was purified by flash-chromatography (heptane:acetone:formic acid 6:4:0.01 and then 5:5:0.01) to afford the title compound.

$^1$H-NMR (CDCl$_3$, 200 MHz): δ 4.10 (m, 3H), 4.70 (s, 2H), 4.85 (d, 1H), 6.05 (s, 2H), 6.80-7.00 (m, 5H), 7.20-7.40 (m, 4H), 7.40 (s, 1H), 7.55 (dd, 1H).

MS (CI) m/z: 508.0 (M$^-$, 100), 509.0 (30), 510.0 (10).

tert-butyl (4-{(E)-[(4-fluorophenyl)imino]methyl}phenoxy)acetate tert-Butyl (4-formylphenoxy)acetate (93.7 g, 0.40 mol) was dissolved in dry toluene (200 mL), added 4-fluoroaniline (38.1 mL, 0.40 mol) and p-toluene sulfonic acid (cat, ~1 g). The mixture was refluxed in a Dean-Stark apparatus for 2 hours, cooled at an icebath and a precipitate was formed. The precipitate was filtered, washed with cold heptane and dried to afford the title compound.

¹H-NMR (CDCl₃, 200 MHz): δ 1.6 (s, 9H), 4.8 (s, 2H), 7.0-7.4 (m, 6H), 7.9 (d, 2H), 8.4 (s, tert-Butyl (4-{(E)-[(4-methylphenyl)imino]methyl}phenoxy)acetate tert-Butyl (4-formylphenoxy)acetate (5.0 g, 21.2 mmol) was dissolved in dry toluene (100 mL) and p-toluidine (2.27 g, 21.2 mmol) was added. The mixture was refluxed in a Dean-Stark apparatus for 18 hours, cooled and concentrated under reduced pressure. Heptane was added and the mixture was concentrated under reduced pressure. This afforded the title compound.

¹H-NMR (CDCl₃, 200 MHz): δ 1.5 (s, 9H), 2.4 (s, 3H), 4.6 (s, 2H), 7.0 (d, 2H), 7.2 (s, 4H), 7.9 (d, 2H), 8.4 (s, 1H).

tert-butyl (4-{(1R,2R)-2-({[2-(1,3-benzodioxol-5-yl)-5,5-dimethyl-1,3-dioxan-2-yl]methyl}thio)-1-[(4-methylphenyl)amino]-3-oxo-3-[(4S)-2-oxo-4-phenyl-1,3-oxazolidin-3-yl]propyl}phenoxy)acetate Tetraisopropyl orthotitanate (0.21 mL, 0.72 mmol) was added to a solution of TiCl₄ (1M in CH₂Cl₂, 2.16 mL, 2.16 mmol) in CH₂Cl₂ (40 mL) held at 0° C. under inert atmosphere. The mixture was stirred for ten minutes, then (4S)-3-[({[2-(1,3-benzodioxol-5-yl)-5,5-dimethyl-1,3-dioxan-2-yl]methyl}thio)acetyl]-4-phenyl-1,3-oxazolidin-2-one (Method 14) (1.40 g, 2.88 mmol) in dry CH₂Cl₂ (40 mL) was added dropwise over 20 minutes and the mixture was stirred for ten minutes at 0° C. Then tert-Butyl (4-{(E)-[(4-methylphenyl)imino]methyl}phenoxy)acetate (Method 19) (2.02 g, 5.77 mmol) in dry CH₂Cl₂ (40 mL) was added dropwise over 20 minutes and the mixture was given –30° C. and stirred for 15 minutes. Ethyl diisopropyl amine (0.99 mL, 5.77 mmol) was added dropwise over 10 minutes and the mixture was stirred at –30° C. for one hour. The mixture was then given –78° C., added isopropanol (15 mL) and slowly given room temperature over two hours. 10% NH₄Cl (50 mL) was added and the mixture was stirred for 15 minutes at room temperature, added brine (150 mL) and then extracted twice with 300 mL diethyl ether. The combined organic layer was dried (MgSO₄) and concentrated under reduced pressure. Purification by flash-chromatography (heptane:EtOAc 4:1 then 3:1) afforded the title compound.

¹H-NMR (CDCl₃, 200 MHz): δ 0.6 (s, 3H), 1.2 (s, 3H), 1.5 (s, 9H), 2.2 (s, 3H), 2.6-2.8 (m, 2H), 3.2-3.6 (m, 4H), 4.2 (m, 1H), 4.5 (s, 2H), 4.6-4.8 (m, 2H), 5.3 (d, 1H), 5.7 (d, 1H), 6.0 (s, 2H), 6.4 (m, 1H), 6.6-7.5 (m, 15H).

tert-Butyl {4-[(2R,3R)-3-({[2-(1,3-benzodioxol-5-yl)-5,5-dimethyl-1,3-dioxan-2-yl]methyl}thio)-1-(4-methylphenyl)-4-oxoazetidin-2-yl]phenoxy}acetate tert-Butyl (4-{(1R,2R)-2-({[2-(1,3-benzodioxol-5-yl)-5,5-dimethyl-1,3-dioxan-2-yl]methyl}thio)-1-[(4-methylphenyl)amino]-3-oxo-3-[(4S)-2-oxo-4-phenyl-1,3-oxazolidin-3-yl]propyl}phenoxy)acetate (Method 20) (1.70 g, 2.03 mmol) was dissolved in dry toluene (200 mL) and heated to 90° C. under inert atmosphere. N,O-Bis(trimethylsilyl)acetamide (BSA, 1.50 mL, 6.10 mmol) was added and the mixture was stirred at 90° C. for one hour. The mixture was then given 45° C. and tetrabutylammonium fluoride (TBAF, cat., 0.1 g) was added and the mixture was stirred at 45° C. for 19 hours. The mixture was then concentrated under reduced pressure and purified by flash-chromatography (heptane:EtOAc 4:1). This afforded the title compound.

¹H-NMR (CDCl₃, 200 MHz): δ 0.6 (s, 3H), 1.2 (s, 3H), 1.5 (s, 9H), 2.1 (s, 3H), 3.0 (d, 2H), 3.4 (m, 4H), 4.0 (d, 1H), 4.5 (s, 2H), 4.8 (d, 1H), 6.0 (s, 2H), 6.8-7.4 (m, 11H).

{4-[(2R,3R)-3-{[2-(1,3-Benzodioxol-5-yl)-2-oxoethyl]thio}-1-(4-methylphenyl)-4-oxoazetidin-2-yl]phenoxy}acetic Acid tert-Butyl {4-[(2R,3R)-3-({[2-(1,3-benzodioxol-5-yl)-5,5-dimethyl-1,3-dioxan-2-yl]methyl}thio)-1-(4-methylphenyl)-4-oxoazetidin-2-yl]phenoxy}acetate (Method 21) (0.21 g, 0.32 mmol) was dissolved in formic acid (10 mL) at room temperature and stirred for 30 minutes. The mixture was concentrated under reduced pressure (temperature<30° C.) and this crude oil was purified by flash-chromatography (heptane:acetone:formic acid 6:4:0.01) to afford the title compound.

¹H-NMR (CDCl₃, 200 MHz): δ 2.25 (s, 3H), 4.05 (d, 1H), 4.10 (d, 2H), 4.60 (s, 2H), 4.85 (d, 1H), 6.05 (s, 2H), 6.80-7.60 (m, 11H).

MS (CI) m/z: 504.0 (M⁻, 100), 505.1 (30), 506.0 (10).

β,β-dimethyl-D-phenylalanine trifluoroacetate

N-(tert-butoxycarbonyl)-b,b-dimethyl-D-phenylalanine tert-butyl ammonium salt (51.2 mg, 0.14 mmol) was dissolved in DCM (15 ml). Water (10 ml) was added and the mixture was acidified to pH 1 with HCl (1M). The organic phase was washed with water (3×10 ml) and the water phase extracted with DCM (3×10 ml). The solvent was removed under reduced pressure. The residue was dissolved in DCM (4 ml) and TFA (2.5 ml) was added and the mixture was stirred for 2 hours. The solvent was removed under reduced pressure and the residue was dried under vacuum overnight. The title compound was obtained. M/z: 194.18 (M+1).

tert-Butyl (4-{(E)-[(4-chlorophenyl)imino]methyl}phenoxy)acetate tert-Butyl (4-formylphenoxy)acetate (17.4 g, 73.4 mmol) was dissolved in dry toluene (120 mL) and 4-chloroaniline (9.37 g, 73.4 mmol) was added. The mixture was refluxed in a Dean-Stark apparatus for 20 hours, cooled and concentrated under reduced pressure. Hexane was added and a precipitate formed. This precipitate was filtered, washed twice with cold hexane and dried. This afforded the title compound.

¹H-NMR (CDCl₃, 200 MHz): δ 1.5 (s, 9H), 4.6 (s, 2H), 7.0 (d, 2H), 7.2 (d, 2H), 7.4 (d, 2H), 7.8 (d, 2H), 8.4 (s, 1H).

MS (CI) ink: 368.0 (M⁺+Na, 100), 369.0 (20), 370.0 (30), 371.0 (10).

tert-Butyl (4-{(1R)-1-[(4-chlorophenyl)amino]-2-[(4-methoxybenzyl)thio]-3-oxo-3-[(4S)-2-oxo-4-phenyl-1,3-oxazolidin-3-yl]propyl}phenoxy)acetate TiCl₄ (1M in CH₂Cl₂, 4.2 mL, 4.2 mmol) was added to a solution of tetraisopropyl orthotitanate (0.4 mL, 1.4 mmol) in CH₂Cl₂ (60 mL) held at 0° C. under inert atmosphere. The mixture was stirred for 15 minutes, then (4S)-3-{[(4-methoxybenzyl)thio]acetyl}-4-phenyl-1,3-oxazolidin-2-one (Method 3) (2.0 g, 5.6 mmol) in dry CH₂Cl₂ (60 mL) was added dropwise over 30 minutes and the mixture was stirred for ten minutes. Then tert-Butyl (4-{(E)-[(4-chlorophenyl)imino]methyl}phenoxy)acetate (Method 24) (3.9 g, 11.2 mmol) in dry CH₂Cl₂ (60 mL) was added dropwise over 30 minutes, the mixture was given –30° C. and stirred for 20 minutes. Ethyl diisopropyl amine (1.9 mL, 11.2 mmol) in 20 mL CH$_2$Cl$_2$ was added dropwise over five minutes and the mixture was stirred at −30° C. for 60 minutes. The mixture was then given −78° C., added isopropanol (30 mL) and slowly given room temperature over one hour. 10% NH$_4$Cl (100 mL) was added and the mixture was stirred for 20 minutes at room temperature and then extracted twice with diethyl ether. The combined organic layer was washed with water, dried (MgSO$_4$) and concentrated under reduced pressure. Purification by flash-chromatography (Heptane:EtOAc 4:1 then 3:1 then 2:1) afforded the title compound.

MS (CI) m/z: 725.2 (M$^+$+Na, 100), 727.2 (50), 728.2 (20)

tert-Butyl (4-{(2R,3R)-1-(4-chlorophenyl)-3-[(4-methoxybenzyl)thio]-4-oxoazetidin-2-yl}phenoxy) acetate tert-Butyl (4-{(1R)-1-[(4-chlorophenyl)amino]-2-[(4-methoxybenzyl)thio]-3-oxo-3-[(4S)-2-oxo-4-phenyl-1,3-oxazolidin-3-yl]propyl}phenoxy)acetate (Method 25) (2.3 g, 3.3 mmol) was dissolved in dry toluene (250 mL) and heated to 90° C. under inert atmosphere. N,O-Bis(trimethylsilyl) acetamide (BSA, 2.4 mL, 9.8 mmol) was added and the mixture was stirred at 90° C. for one hour. The mixture was then given 45° C. and tetrabutylammonium fluoride (TBAF, 0.2 g) was added. The mixture was stirred at 45° C. for 2 hours. After cooling, the mixture was concentrated under reduced pressure and purified by flash-chromatography (Heptane:EtOAc 4:1). This afforded the title compound.

$^1$H-NMR (CDCl$_3$, 200 MHz): δ 1.5 (s, 9H), 3.8 (s, 3H), 3.9 (m, 3H), 4.5 (m, 3H), 6.7 (d, 2H), 6.9 (m, 2H), 7.1-7.3 (m, 8H).

tert-Butyl (4-{(2R,3R)-1-(4-chlorophenyl)-3-[(3-nitropyridin-2-yl)dithio]-4-oxoazetidin-2-yl}phenoxy)acetate tert-Butyl (4-{(2R,3R)-1-(4-chlorophenyl)-3-[(4-methoxybenzyl)thio]-4-oxoazetidin-2-yl}phenoxy)acetate (Method 26) (0.9 g, 1.7 mmol) was dissolved in CH$_2$Cl$_2$ (50 mL) and given 0° C. under inert atmosphere. 3-Nitro-2-pyridinesulfenyl chloride (0.4 g, 2.0 mmol) was added and the mixture was stirred for 30 minutes at 0° C., then 30 minutes at room temperature. Concentration under reduced pressure and purification by flash-chromatography (Heptane:EtOAc 3:1 then 2:1) afforded the title compound.

{4-[(2R,3R)-3-{[2-(1,3-Benzodioxol-5-yl)-2-oxoethyl]thio}-1-(4-chlorophenyl)-4-oxoazetidin-2-yl] phenoxy}acetic Acid tert-Butyl (4-{(2R,3R)-1-(4-chlorophenyl)-3-[(3-nitropyridin-2-yl)dithio]-4-oxoazetidin-2-yl}phenoxy)acetate (Method 27) (0.70 g, 1.22 mmol) was dissolved in acetone (30 mL) at room temperature, then water (10 mL) and triphenyl phosphine (0.32 g, 1.22 mmol) was added. The mixture was stirred at room temperature for 15 minutes and then concentrated under reduced pressure to afford the crude thiol as a brown oil. This crude thiol was immediately dissolved in CH$_2$Cl$_2$ (30 mL) and 1-benzo[1,3]dioxol-5-yl-2-bromo-ethanone (0.59 g, 2.44 mmol) was added, followed by Et$_3$N (0.34 mL, 2.44 mmol). The mixture was stirred at room temperature for 18 hours, concentrated under reduced pressure and purified by flash-chromatography (Heptane:EtOAc 7:3 and then 2:1). The resulting product (0.90 g) was dissolved in 15 ml formic acid and stirred at room temperature for 3 hours. Concentration under reduced pressure and purification by flash-chromatography afforded the title compound.

$^1$H-NMR (CDCl$_2$, 200 MHz): δ 4.1 (s, 3H), 4.7 (d, 2H), 4.9 (s, 1H), 6.1 (s, 2H), 6.8-7.0 (m, 3H), 7.2-7.4 (m, 7H), 7.5 (d, 1H).

MS (CI) m/z: 524.0 (M$^-$, 100), 525.0 (30), 526.0 (40), 527.0 (10).

{4-[(2R,3R)-3-{[2-(2,3-dihydro-1,4-benzodioxin-6-yl)-2-oxoethyl]thio}-1-(4-fluorophenyl)-4-oxoazetidin-2-yl]phenoxy}acetic Acid To a solution of tert-butyl (4-{(2R,3R)-1-(4-fluorophenyl)-3-[(3-nitropyridin-2-yl)dithio]-4-oxoazetidin-2-yl]phenoxy)acetate (0.100 g, 0.179 mmol) in acetone (2 ml) and water (0.5 ml) was added triphenylphosphine (0.047 g, 0.179 mmol). After 30 minutes, the mixture was concentrated. To the residue was added dichloromethane (3 ml) followed by the addition of triethylamine (0.073 g, 0.717 mmol) and 2-bromo-1-(2,3-dihydro-1,4-benzodioxin-6-yl) ethanone (0.115 g, 0.448 mmol). After 30 minutes, full conversion of the thiol had been achieved. The mixture was concentrated and to the residue was added formic acid (2 g) and trifluoroacetic acid (0.2 g). The mixture was allowed to stir at room temperature for 3 h. The crude product obtained was purified through preparative HPLC using an eluent of 10-50% CH$_3$CN in 0.1M NH$_4$OAc buffer. Freeze drying of pure fractions afforded the desired compound. $^1$H NMR [(CD$_3$)$_2$SO), 400 MHz] δ 4.21-4.32 (m, 9H), 5.09 (d, 1H), 6.78-7.44 (m, 11H).

(R or S)-2-Bromo-1-(2,3-dihydro-benzo[1,4]dioxin-6-yl)-ethanol (R)-2-Methyl-CBS-oxazaborolidine (1M in toluene, 1.95 ml, 1.95 mmol) was added to a flask containing 20 ml dry THF under Ar2(g) at 0° C. BH3.SMe2 (2M in THF, 6.0 ml, 12.0 mmol) was added over 5 min. 2-Bromo-1-(2,3-dihydro-benzo[1,4]dioxin-6-yl)-ethanone (4.7 g) was dissolved in 30 ml dry THF, added to a dropping funnel and added to the above solution slowly (ca 4 h) at 0° C. The mixture was stirred over night. The reaction was quenched by addition of 0.4 ml MeOH. The mixture was concentrated under reduced pressure, diethyl ether (200 ml) was added and the solution was extracted with 0.5M HCl (pH=1). The aq-phase was extracted with 100 ml diethyl ether and the combined organic phases were washed with ca 2% NaHCO3 followed by brine. The organic phase was dried with MgSO4 and concentrated to yield the title compound.

$^1$H-NMR (CDCl$_3$, 400 MHz): δ 3.44-3.62 (m, 2H), 4.26 (s, 4H), 4.78-4.85 (m, 1H), 6.82-6.93 (m, 3H).

{4-[(2R,3R)-3-[(R or S)-2-(2,3-Dihydro-benzo[1,4] dioxin-6-yl)-2-hydroxy-ethylsulfanyl]-1-(4-fluorophenyl)-4-oxo-azetidin-2-yl]-phenoxy}-acetic Acid Triphenyl phosphine (0.105 g, 0.400 mmol) was added to a solution of {4-[(2R,3R)-1-(4-fluoro-phenyl)-3-(3-nitro-pyridin-2-yldisulfanyl)-4-oxo-azetidin-2-yl]-phenoxy}-acetic acid (0.180 g, 0.359 mmol) in acetone/water (4 mL/1 mL) at RT. The mixture was stirred for 15 min before the solvent was removed under reduced pressure. The residue was dissolved in DMF (5 mL). Triethylamine (0.20 mL, 1.4 mmol) and (R or S)-2-bromo-1-(2,3-dihydro-benzo[1,4]dioxin-6-yl)-ethanol (0.220 g, 0.849 mmol) were added and the solution was stirred at room temperature for 2 h. The reaction was quenched by the addition of NH4OAc (aq, 0.1 M, 3 mL) and the resulting mixture was purified by preparative HPLC using a gradient of 20-70% MeCN in a 0.1M ammonium acetate buffer as eluent. Freeze-drying of the pure fractions gave of the desired product.

$^1$H-NMR (DMSO, 400 MHz): δ 2.86 (d, 2H), 4.16-4.23 (m, 6H), 4.26 (d, 1H), 4.53-4.61 (m, 1H), 5.00 (d, 1H), 5.48 (bs, 1H), 6.72-6.84 (m, 5H), 7.10-7.19 (m, 2H), 7.20-7.32 (m, 4H).

Absorption

Absorption of the compounds of formula (I) was tested in a Caco-2 cells model (Gastroenterology 1989, 96, 736):

| Compound (I) | Caco value ($10^{-6}$ cm/sec) |
|---|---|
| N-({4-[(2R,3R)-3-{[2-(2,3-dihydro-1,4-benzodioxin-6-yl)-2-hydroxyethyl]thio}-1-(4-fluorophenyl)-4-oxoazetidin-2-yl]phenoxy}acetyl)glycyl-3-methyl-D-valine | 0.02 |
| N-({4-[(2R,3R)-3-{[(2R or S)-2-(1,3-benzodioxol-5-yl)-2-hydroxyethyl]thio}-1-(4-fluorophenyl)-4-oxoazetidin-2-yl]phenoxy}acetyl)glycyl-3-cyclohexyl-D-alanine | 0.05 |

The invention claimed is:

1. A compound of formula (I):

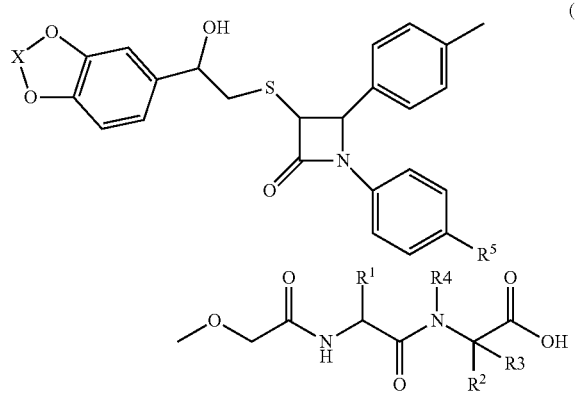

wherein:

X is —CH$_2$—, —CH$_2$CH$_2$—, or —CH$_2$CH$_2$CH$_2$—;

R$^1$ is H, C$_{1-6}$ alkyl, C$_{3-6}$cycloalkyl or aryl;

R$^2$ and R$^3$ are, independently, hydrogen, a branched or unbranched C$_{1-6}$alkyl, C$_{3-6}$cycloalkyl or aryl; wherein said C$_{1-6}$alkyl may be optionally substituted by one or more hydroxy, amino, guanidino, carbamoyl, carboxy, C$_{1-6}$alkoxy, (C$_1$-C$_4$alkyl)$_3$Si, N—(C$_{1-6}$alkyl)amino, N,N—(C$_{1-6}$alkyl)$_2$amino, C$_{1-6}$alkylS(O)$_a$ wherein a is 0-2, C$_{3-6}$cycloalkyl or aryl; and wherein any aryl group may be optionally substituted by one or two substituents selected from halo, hydroxy, cyano, C$_{1-6}$alkyl and C$_{1-6}$alkoxy;

R$^4$ is hydrogen, C$_{1-6}$ alkyl, or arylC$_{1-6}$ alkyl;

wherein R$^3$ and R$^2$ may form a ring with 3-7 carbon atoms and wherein R$^4$ and R$^2$ may form a ring with 2-6 carbon atoms; and R$^5$ is selected from hydrogen, halo, nitro, cyano, hydroxy, carboxy, carbamoyl, sulphamoyl, C$_{1-6}$alkyl, C$_{1-6}$alkoxy, C$_{1-6}$alkanoyl, C$_{1-6}$alkanoyloxy, N—(C$_{1-6}$alkyl)amino, N,N—(C$_{1-6}$alkyl)$_2$amino, C$_{1-6}$alkanoylamino, N—(C$_{1-6}$ alkyl)carbamoyl, N,N—(C$_{1-6}$alkyl)$_2$carbamoyl, C$_{1-6}$alkylS(O)$_a$ wherein a is 0 to 2, C$_{1-6}$alkoxycarbonyl, N—(C$_{1-6}$alkyl)sulphamoyl and N,N—(C$_{1-6}$ alkyl)$_2$sulphamoyl;

or a pharmaceutically acceptable salt, or a prodrug thereof.

2. A compound of formula (12):

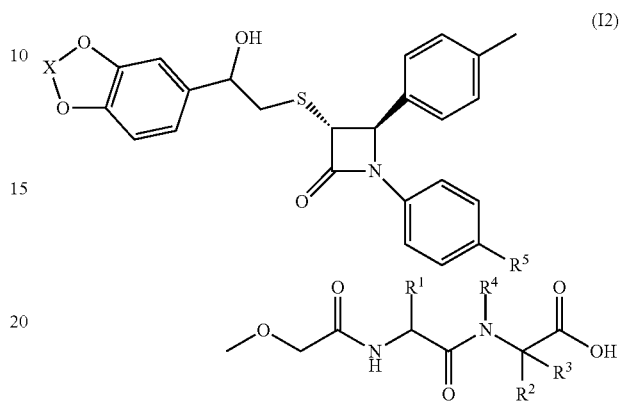

wherein:

X is —CH$_2$—, —CH$_2$CH$_2$—, or —CH$_2$CH$_2$CH$_2$—;

R$^1$ is H, C$_{1-6}$ alkyl, C$_{3-6}$cycloalkyl or aryl;

R$^2$ and R$^3$ are, independently, hydrogen, a branched or unbranched C$_{1-6}$alkyl, C$_{3-6}$cycloalkyl or aryl; wherein said C$_{1-6}$alkyl may be optionally substituted by one or more hydroxy, amino, guanidino, carbamoyl, carboxy, C$_{1-6}$alkoxy, (C$_1$-C$_4$alkyl)$_3$Si, N—(C$_{1-6}$alkyl)amino, N,N—(C$_{1-6}$alkyl)$_2$amino, C$_{1-6}$alkylS(O)$_a$ wherein a is 0-2, C$_{3-6}$cycloalkyl or aryl; and wherein any aryl group may be optionally substituted by one or two substituents selected from halo, hydroxy, cyano, C$_{1-6}$alkyl and C$_{1-6}$alkoxy;

R$^4$ is hydrogen, C$_{1-6}$ alkyl, or arylC$_{1-6}$ alkyl;

wherein R$^3$ and R$^2$ may form a ring with 3-7 carbon atoms and wherein R$^4$ and R$^2$ may form a ring with 2-6 carbon atoms; and R$^5$ is selected from hydrogen, halo, nitro, cyano, hydroxy, carboxy, carbamoyl, sulphamoyl, C$_{1-6}$ alkyl, C$_{1-6}$alkoxy, C$_{1-6}$alkanoyl, C$_{1-6}$alkanoyloxy, N—(C$_{1-6}$ alkyl)amino, N,N—(C$_{1-6}$alkyl)$_2$amino, C$_{1-6}$alkanoylamino, N—(C$_{1-6}$alkyl)carbamoyl, N,N—(C$_{1-6}$alkyl)$_2$ carbamoyl, C$_{1-6}$alkylS(O)$_a$ wherein a is 0 to 2, C$_{1-6}$alkoxycarbonyl, N—(C$_{1-6}$alkyl)sulphamoyl and N,N—(C$_{1-6}$alkyl)$_2$sulphamoyl;

or a pharmaceutically acceptable salt, or a prodrug thereof.

3. A compound according to claim 1, wherein X is —CH$_2$—.

4. A compound according to claim 1 or 2, wherein X is —CH$_2$CH$_2$—.

5. A compound according to claim 1, wherein X is —CH$_2$CH$_2$CH$_2$—.

6. A compound according to claim 1, wherein,

R$^1$ is hydrogen;

R$^2$ and R$^3$ are, independently, hydrogen or a branched or unbranched C$_{1-6}$alkyl; wherein said C$_{1-6}$alkyl is substituted by C$_{3-6}$cycloalkyl, aryl or amino; and R$^4$ is hydrogen.

7. A compound according to claim 1 wherein,

R$^1$ is hydrogen;

R$^2$ and R$^3$ are, independently, hydrogen or a branched or unbranched C$_{1-6}$alkyl; wherein said C$_{1-6}$alkyl is substituted by C$_{3-6}$cycloalkyl; and R$^4$ is hydrogen.

8. A compound according to claim 7, wherein, $R^2$ is hydrogen and $R^3$ is tent-butyl.

9. A compound according to claim 7, wherein, $R^2$ is hydrogen and $R^3$ is methyl;
wherein said methyl is substituted by cyclolohexyl.

10. A compound according to claim 1, wherein, $R^5$ is chlorine or fluorine.

11. One or more compounds selected from:

N-({4-[(2R,3R)-3-{[2-(1,3-Benzodioxol-5-yl)-2-hydroxyethyl]thio}-1-(4-fluorophenyl)-4-oxoazetidin-2-yl]phenoxy}acetyl)glycyl-3-cyclohexyl-D-alanine;

N-({4-[(2R,3R)-3-{[2-(1,3-Benzodioxol-5-yl)-2-hydroxyethyl]thio}-1-(4-fluorophenyl)-4-oxoazetidin-2-yl]phenoxy}acetyl)glycyl-3-methyl-D-valine;

N-({4-[(2R,3R)-3-{[(2R)-2-(1,3-benzodioxol-5-yl)-2-hydroxyethyl]thio}-1-(4-fluorophenyl)-4-oxoazetidin-2-yl]phenoxy}acetyl)glycyl-3-methyl-D-valine; and N-({4-[(2R,3R)-3-{[(2R)-2-(1,3-benzodioxol-5-yl)-2-hydroxyethyl]thio}-1-(4-fluorophenyl)-4-oxoazetidin-2-yl]phenoxy}acetyl)glycyl-3-cyclohexyl-D-alanine.

12. A compound of the formula (XVI):

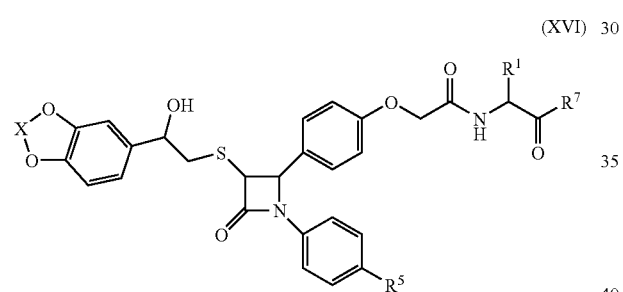

(XVI)

wherein:

X is —$CH_2$—, —$CH_2CH_2$—, or —$CH_2CH_2CH_2$—;

$R^1$ is hydrogen, $C_{1-6}$ alkyl, $C_{3-6}$cycloalkyl or aryl;

$R^5$ is selected from halo, nitro, cyano, hydroxy, carboxy, carbamoyl, sulphamoyl, $C_{1-6}$alkyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl; and $R^7$ is an hydroxy group or a $C_{1-4}$ alkoxy group.

13. A method of treating or preventing hyperlipidemic conditions comprising the administration of an effective amount of a compound according to claim 1 to a mammal in need thereof.

14. A method of treating or preventing atherosclerosis comprising the administration of an effective amount of a compound according to claim 1 to a mammal in need thereof.

15. A pharmaceutical formulation comprising a compound according to claim 1 in admixture with a pharmaceutically acceptable adjuvant, diluent and/or carrier.

16. A process for preparing a compound of formula (I)

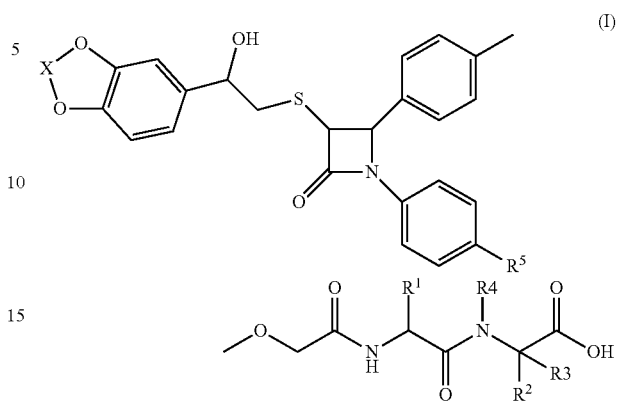

(I)

wherein:

X is —$CH_2$—, —$CH_2CH_2$—, or —$CH_2CH_2CH_2$—;

$R^1$ is H, $C_{1-6}$ alkyl, $C_{3-6}$cycloalkyl or aryl;

$R^2$ and $R^3$ are, independently, hydrogen, a branched or unbranched $C_{1-6}$alkyl, $C_{3-6}$cycloalkyl or aryl; wherein said $C_{1-6}$alkyl may be optionally substituted by one or more hydroxy, amino, guanidino, carbamoyl, carboxy, $C_{1-6}$alkoxy, ($C_1$-$C_4$alkyl)$_3$Si, N—($C_{1-6}$alkyl)amino, N,N—($C_{1-6}$alkyl)$_2$amino, $C_{1-6}$alkylS(O)$_a$ wherein a is 0-2, $C_{3-6}$cycloalkyl or aryl; and wherein any aryl group may be optionally substituted by one or two substituents selected from halo, hydroxy, cyano, $C_{1-6}$alkyl, and $C_{1-6}$alkoxy;

$R^4$ is hydrogen, $C_{1-6}$ alkyl, or aryl$C_{1-6}$ alkyl;

wherein $R^3$ and $R^2$ may form a ring with 3-7 carbon atoms and wherein $R^4$ and $R^2$ may form a ring with 2-6 carbon atoms; and $R^5$ is selected from hydrogen, halo, nitro, cyano, hydroxy, carboxy, carbamoyl, sulphamoyl, $C_{1-6}$alkyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$ alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$ alkyl)$_2$sulphamoyl;

or a pharmaceutically acceptable salt, or a prodrug thereof which process (wherein variable groups are, unless otherwise specified, as defined in formula (I)) comprises any of the steps:

Process 1) reacting a compound of formula (II2):

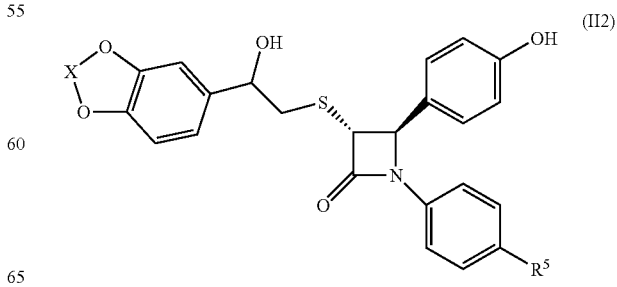

(II2)

with a compound of formula (III):

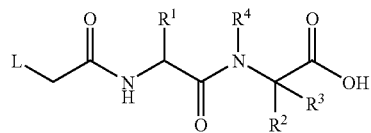
(III)

wherein L is a displaceable group; or

Process 2) reacting an acid of formula (IV2):

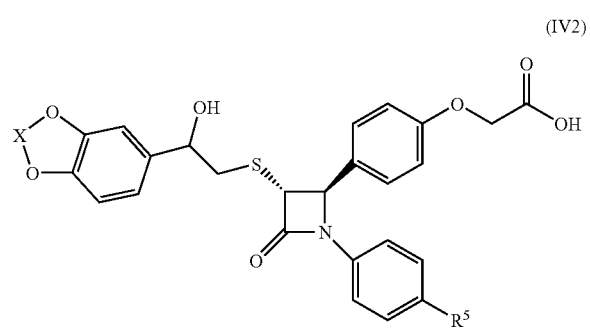
(IV2)

or an activated derivative thereof; with an amine of formula (V):

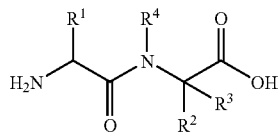
(V)

or

Process 3): reacting an acid of formula (VI2):

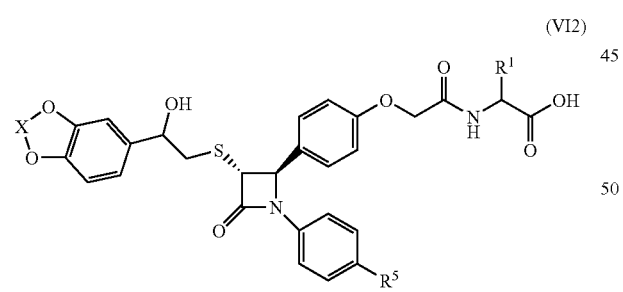
(VI2)

or an activated derivative thereof, with an amine of formula (VII):

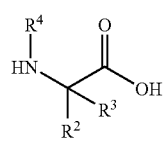
(VII)

or

Process 4): reducing a compound of formula (VIII2):

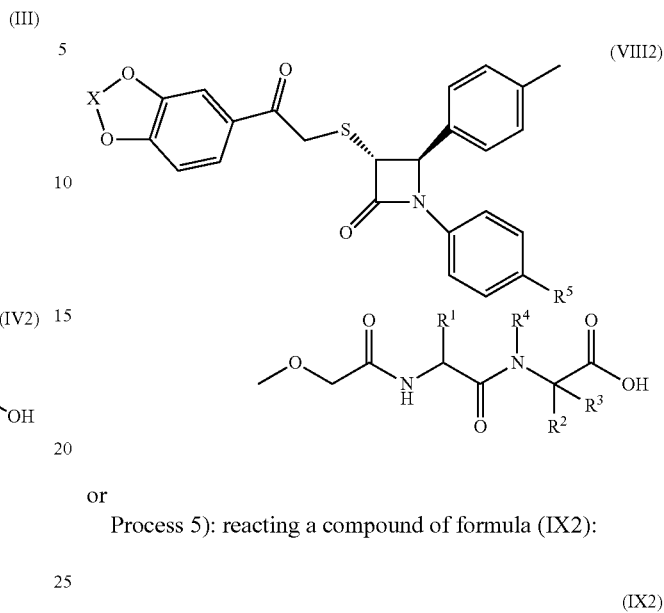
(VIII2)

or

Process 5): reacting a compound of formula (IX2):

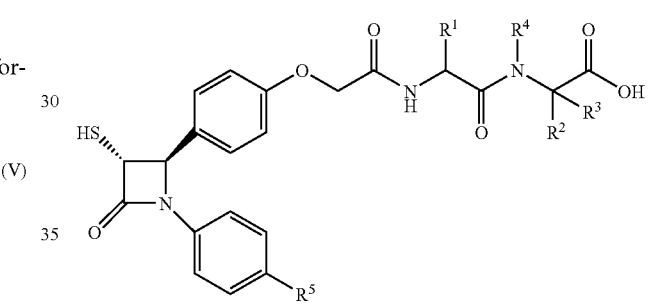
(IX2)

with a compound of formula (X):

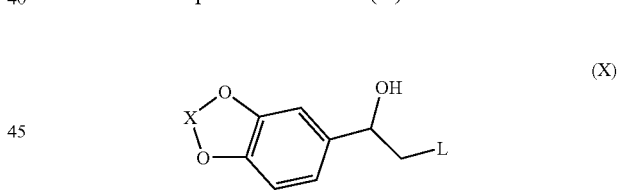
(X)

wherein L is a displaceable group; or

Process 6): reacting a compound of formula (XI2):

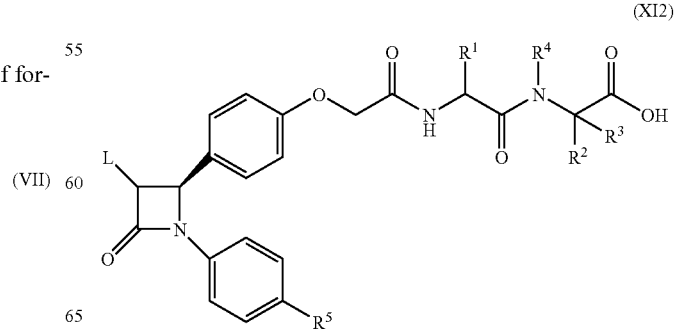
(XI2)

wherein L is a displaceable group; with a compound of formula (XII):

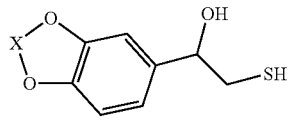

(XII)

or

Process 7): De-esterifying a compound of formula (XIII2)

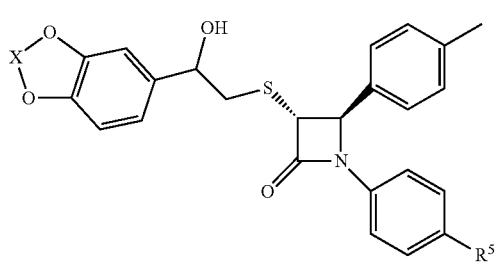

(XIII2)

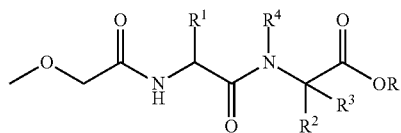

wherein the group C(O)OR is an ester group.

17. A compound according to claim 2, wherein X is —$CH_2$—.

18. A compound according to claim 2, wherein X is —$CH_2CH_2$—.

19. A compound according to claim 2, wherein X is —$CH_2CH_2CH_2$—.

20. A compound according to claim 2, wherein,
$R^1$ is hydrogen;
$R^2$ and $R^3$ are, independently, hydrogen or a branched or unbranched $C_{1-6}$alkyl; wherein said $C_{1-6}$alkyl is substituted by $C_{3-6}$cycloalkyl, aryl or amino; and
$R^4$ is hydrogen.

21. A compound according to claim 2 wherein,
$R^1$ is hydrogen;
$R^2$ and $R^3$ are, independently, hydrogen or a branched or unbranched $C_{1-6}$alkyl; wherein said $C_{1-6}$alkyl is substituted by $C_{3-6}$cycloalkyl; and
$R^4$ is hydrogen.

22. A compound according to claim 21, wherein, $R^2$ is hydrogen and $R^3$ is tent-butyl.

23. A compound according to claim 21, wherein, $R^2$ is hydrogen and $R^3$ is methyl; wherein said methyl is substituted by cyclolohexyl.

24. A compound according to claim 2, wherein, $R^5$ is chlorine or fluorine.

25. A method of treating or preventing hyperlipidemic conditions comprising the administration of an effective amount of a compound according to claim 2 to a mammal in need thereof.

26. A method of treating or preventing atherosclerosis comprising the administration of an effective amount of a compound according to claim 2 to a mammal in need thereof.

27. A pharmaceutical formulation comprising a compound according to claim 2 in admixture with a pharmaceutically acceptable adjuvant, diluent and/or carrier.

28. A method of treating or preventing hyperlipidemic conditions comprising the administration of an effective amount of a compound according to claim 12 to a mammal in need thereof.

29. A method of treating or preventing atherosclerosis comprising the administration of an effective amount of a compound according to claim 12 to a mammal in need thereof.

30. A pharmaceutical formulation comprising a compound according to claim 12 in admixture with a pharmaceutically acceptable adjuvant, diluent and/or carrier.

31. A pharmaceutical formulation comprising a compound according to claim 12 in admixture with a pharmaceutically acceptable adjuvant, diluent and/or carrier.

* * * * *

UNITED STATES PATENT AND TRADEMARK OFFICE
CERTIFICATE OF CORRECTION

| | | |
|---|---|---|
| PATENT NO. | : 7,906,502 B2 | Page 1 of 1 |
| APPLICATION NO. | : 11/993463 | |
| DATED | : March 15, 2011 | |
| INVENTOR(S) | : Alenfalk et al. | |

It is certified that error appears in the above-identified patent and that said Letters Patent is hereby corrected as shown below:

IN THE CLAIMS:

Please replace claim 8 as follows (col. 87, claim 8, line 2):

--8. A compound according to claim 7, wherein $R^2$ is hydrogen and $R^3$ is tert-butyl.--

Please replace claim 22 as follows (col. 92, claim 22, line 2):

--22. A compound according to claim 21, wherein, $R^2$ is hydrogen and $R^3$ is tert-butyl.--

Signed and Sealed this
Thirty-first Day of May, 2011

David J. Kappos
*Director of the United States Patent and Trademark Office*